(12) United States Patent
Wu

(10) Patent No.: US 9,562,029 B2
(45) Date of Patent: *Feb. 7, 2017

(54) C-GLYCOSIDE DERIVATIVES

(75) Inventor: Frank Wu, Shandong Province (CN)

(73) Assignee: XUANZHU PHARMA CO., LTD., Jinan (CN)

( * ) Notice: Subject to any disclaimer, the term of this patent is extended or adjusted under 35 U.S.C. 154(b) by 80 days.

This patent is subject to a terminal disclaimer.

(21) Appl. No.: 14/129,316

(22) PCT Filed: Jun. 25, 2012

(86) PCT No.: PCT/CN2012/000868
§ 371 (c)(1),
(2), (4) Date: Jan. 13, 2014

(87) PCT Pub. No.: WO2013/000275
PCT Pub. Date: Jan. 3, 2013

(65) Prior Publication Data
US 2014/0128331 A1  May 8, 2014

(30) Foreign Application Priority Data

Jun. 25, 2011 (CN) .......................... 2011 1 0188186
Dec. 22, 2011 (CN) .......................... 2011 1 0435397

(51) Int. Cl.
| | |
|---|---|
| C07D 309/10 | (2006.01) |
| C07D 307/94 | (2006.01) |
| C07D 311/96 | (2006.01) |
| C07D 307/77 | (2006.01) |
| C07D 407/12 | (2006.01) |
| A61K 31/351 | (2006.01) |

(52) U.S. Cl.
CPC ........... *C07D 309/10* (2013.01); *C07D 307/77* (2013.01); *C07D 307/94* (2013.01); *C07D 311/96* (2013.01); *C07D 407/12* (2013.01)

(58) Field of Classification Search
CPC ... C07D 309/10; C07D 407/12; C07D 307/77; C07D 307/94; C07D 311/96
See application file for complete search history.

(56) References Cited

U.S. PATENT DOCUMENTS

| | | | |
|---|---|---|---|
| 5,558,287 | A | 9/1996 | Darsey et al. |
| 6,414,126 | B1 | 7/2002 | Ellsworth et al. |
| 6,515,117 | B2 | 2/2003 | Ellsworth et al. |
| 7,566,699 | B2 | 7/2009 | Fushimi et al. |
| 7,579,449 | B2 | 8/2009 | Eckhardt et al. |
| 7,973,012 | B2 | 7/2011 | Kakinuma et al. |
| 2004/0082779 | A1 | 4/2004 | Vos et al. |
| 2005/0209166 | A1 | 9/2005 | Eckhardt et al. |
| 2006/0247179 | A1 | 11/2006 | Fushimi et al. |
| 2006/0258749 | A1 | 11/2006 | Eckhardt et al. |
| 2007/0104976 | A1 | 5/2007 | Iwakuma et al. |
| 2007/0238866 | A1 | 10/2007 | Deshpande et al. |
| 2008/0058379 | A1 | 3/2008 | Eckhardt et al. |
| 2009/0118201 | A1 | 5/2009 | Chen et al. |
| 2010/0022460 | A1 | 1/2010 | Kakinuma et al. |
| 2010/0171418 | A1 | 7/2010 | Kinoshita et al. |
| 2013/0022587 | A1 | 1/2013 | Nagata et al. |
| 2015/0191502 | A1 | 7/2015 | Wu |
| 2016/0194264 | A1 | 7/2016 | Wu |

FOREIGN PATENT DOCUMENTS

| | | |
|---|---|---|
| CN | 1407990 | 4/2003 |
| CN | 1784415 | 6/2006 |
| CN | 1930141 | 3/2007 |
| CN | 101490028 | 7/2009 |
| CN | 101790311 | 7/2010 |
| EP | 0725031 | 8/1996 |
| EP | 1696708 | 8/2006 |
| JP | 2000149320 | 5/2000 |
| JP | 2003511458 | 3/2003 |
| JP | 2004196788 | 7/2004 |
| JP | 2006516257 | 6/2006 |
| JP | 2007522143 | 8/2007 |

(Continued)

OTHER PUBLICATIONS

"Non-Final Office Action" dated Jul. 29, 2015 in U.S. Appl. No. 14/146,838, 23 pages.

Mansfield, et al., "Single-enantiomer drugs: elegant science, disappointing effects", Clin. Pharmacokinet., vol. 43, No. 5, 2004, pp. 287-290.

International Application No. PCT/CN2012/000868, "International Search Report", Oct. 4, 2012.

Lansdell, Mark I. et al., "Design and synthesis of fluorescent SGLT2 inhibitors," Bioorganic & Medicinal Chemistry Letters 18 (2008), 4944-4947.

(Continued)

*Primary Examiner* — Jonathan S Lau
(74) *Attorney, Agent, or Firm* — Kilpatrick Townsend & Stockton LLP

(57) ABSTRACT

The present invention involves a compound represented by general formula (I), a derivative thereof and a use thereof:

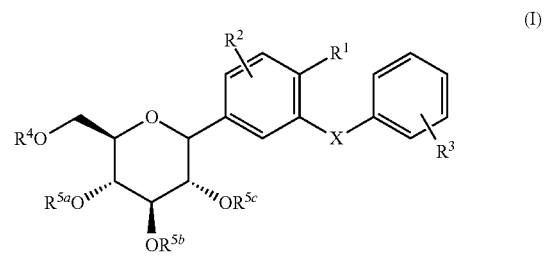

(I)

wherein $R^1$, $R^2$, $R^3$, $R^4$, $R^{5a}$, $R^{5b}$, $R^{5c}$ and X are defined as in the description.

11 Claims, No Drawings

(56) References Cited

FOREIGN PATENT DOCUMENTS

| | | |
|---|---|---|
| JP | 2008540489 | 11/2008 |
| JP | 2009531291 | 9/2009 |
| KR | 1020110065978 | 6/2011 |
| TW | 200846441 | 12/2008 |
| WO | 03035650 | 5/2003 |
| WO | 2005092877 | 10/2005 |
| WO | 2010147430 | 12/2010 |
| WO | 2011115064 | 9/2011 |
| WO | 2012025857 | 3/2012 |
| WO | 2013000275 | 1/2013 |

OTHER PUBLICATIONS

U.S. Appl. No. 14/146,838, Notice of Allowance, mailed Feb. 11, 2016, 17 pages.

U.S. Appl. No. 14/129,316, "Non-FInal Office Action", Nov. 3, 2015, 13 pages.

Guo, "Pd (II)-catalyzed ortho arylation of 6-arylpurines with aryl iodides via purine-directed C—H activation: A new strategy for modification of 6-arylpurine derivatives", Organic letters 13.8 (2011): 2008-2011.

Kawano et al., "Preparation of furo[2,3-h]isoquinoline derivatives as viral entry inhibitors against HIV", XP002730919, retrieved from STN Database accession No. 2003:335106 & WO 03/035650 A1 (Takeda Chemical Industries, Ltd., Japan) May 1, 2003 (May 1, 2003).

Ph Buu-Hoi et al., XP002730917, retrieved from STN Database accession No. 1961:22768, "3-Bromo-4-hydroxybiphenyl", Bulletin De La Societe Chimique De France, vol. 2, 1960, pp. 335-337.

Yang, "Building predictive models for protein tyrosine phosphatase 1B inhibitors based on discriminating structural features by reassembling medicinal chemistry building blocks", Journal of medicinal chemistry 47.24 (2004): 5984-5994.

European Patent Application No. 12 80 5011, "Supplementary European Search Report", Oct. 10, 2014, 3 pages.

Japanese Patent Application No. 2014-517397, "Office Action", May 5, 2015, 3 pages; concise explanation of relevance in English is attached.

European Patent Application No. 14 00 0018, "European Search Report", May 6, 2014, 5 pages.

Japanese Patent Application No. 2014-043695, "Office Action", Dec. 22, 2015, 4 pages; concise explanation of relevance in English is attached.

C-GLYCOSIDE DERIVATIVES

PRIOR RELATED APPLICATIONS

This application is a National Phase application of International Application No. PCT/CN2012/000868 filed Jun. 25, 2012, which claims priority to Chinese Patent Application No. 201110188186.4 filed Jun. 25, 2011, and Chinese Patent Application No. 201110435397.3, filed Dec. 22, 2011, each of which is incorporated herein by reference in its entirety.

TECHNICAL FIELD

The present invention belongs to the field of pharmaceutical technology, more specifically relates to a C-glycoside derivative represented by general formula (I), a pharmaceutically acceptable salt thereof, an easily hydrolyzable ester thereof, a stereoisomer thereof and an intermediate thereof, a process for preparing these compounds and intermediates thereof, a pharmaceutical formulation and a pharmaceutical composition containing these compounds, and the use of the present C-glycoside derivative as a sodium glucose cotransporter (SGLT) inhibitor for treating and/or preventing the diabetes such as insulin-dependent diabetes mellitus (Type I diabetes mellitus), non-insulin-dependent diabetes mellitus (Type II diabetes mellitus) and the like, besides various diabetes-associated diseases including insulin resistance disease and obesity.

BACKGROUND ART

About 100,000,000 people have the Type II diabetes mellitus all over the world, which is characterized in hyperglycemia caused by excessive hepatic glucose production and peripheral insulin resistance. The hyperglycemia is considered to be a major risk factor for forming the diabetic complication, and be possibly directly relevant to insulin secretion impairment in the later stage of Type II diabetes mellitus. Therefore, it can be expected that the normalization of blood glucose in the patients having the Type II diabetes mellitus can improve the effect of insulin. The currently known anti-diabetic drugs such as sulfonylureas, thiazolidinediones, dimethyl biguanides, and insulins have potential side effects, and therefore there is a need to develop a new and safe anti-diabetic drug that can be orally administrated effectively.

In kidney, glucose can filter freely through renal glomerulus (about 180 g/d) but nearly transport actively at proximal convoluted tubule to be reabsorbed. Among others, two sodium-glucose transporters, i.e. SGLT1 and SGLT2, have an important effect on the glucose reabsorption, in particular SGLT2. SGLT2 specifically expresses the transmembrane protein only at the S1 section of proximal tubule. One of its major physiological functions is to absorb the glucose in the blood flowing through the renal tubule, which comprises 90% of the reabsorption. SGLT2 transports at a ratio of 1:1 sodium-glucose. The SGLT-2 inhibitor can inhibit the absorption of blood glucose in the renal tubule so that a great amount of glucose excretes through the urine. SGLT1 mainly expresses in the distal convoluted tubule, which comprises 10% of the reabsorption. SGLT1 transports at a ratio of 2:1 sodium-glucose. In addition, SGLT1 is also found in the intestinal tract and other tissues. These transporters exert their functions via Na+/ATPase pump and transport to the blood via the glucose transporter-2 (GLUT2). This indicates that the most potential drug target is the SGLT2 transporter, because its absolute re-absorption for glucose in one hand and its merely expression in kidney in the other hand. In the study on the urine glucose from the nephrosis of the familial form, the feasibility of this route has been verified. The urine glucose from the nephrosis of the familial form is mainly manifested as non-quantitative urine glucose (about 10-120 g/d), but the patient has a good general condition and has no chronic negative effect adverse for the health to be found. This benign urine glucose is mainly caused by the genic mutation of the SGLT-2 transporter, which indicates that the selective pharmacological inhibition to SGLT-2 will possibly not produce an adverse effect except for the induction of urine glucose. However, the inhibition SGLT-1 will cause the glucose-galactose malabsorption syndrome, which may result in the dehydration.

By action on SGLT-2 transporter to inhibit the reabsorption of the kidney glucose to treat the high blood glucose, a new route for treating the diabetes mellitus is provided. Although this route cannot directly act on the pathophysiology of Type II diabetes mellitus, however the reduction of blood glucose by increasing the excretion of glucose in kidney can cause the deficiency in the net energy to promote losing the body weight and indirectly improve the obesity conditions. It is found in the study that these drugs can be used in combination of the existing drug for reducing the blood glucose or the insulin, and have a lower risk of the low blood glucose and a potential effect of losing the weight. The safety and effectiveness in the chronic clinical experiment will eventually determine whether the SGLT-2 inhibitor can have a place in the pharmaceutical treatment of the Type II diabetes mellitus.

Among others, the patent literatures such as WO 0127128 and US 2005209166 disclose a series of compounds as SGLT-2 inhibitor.

SUMMARY OF THE INVENTION

The present invention provides the following technical solutions:
A compound represented by general formula (I), a pharmaceutically acceptable salt thereof, an easily hydrolyzable ester thereof or a stereoisomer thereof:

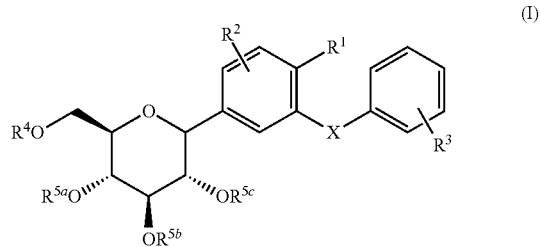

wherein,
$R^1$ and $R^2$ each independently represent hydrogen, —OH, —OR$^6$, alkyl, —CF$_3$, —OCHF$_2$, —OCF$_3$, halogen, —CN, C$_{2-6}$alkynyl, C$_{2-6}$alkenyl, cycloalkyl, C$_{2-4}$alkenyl-C$_{1-4}$alkyl, C$_{2-4}$alkynyl-C$_{1-4}$alkyl, C$_{2-4}$alkenyl-C$_{1-4}$alkoxy, C$_{2-4}$alkynyl-C$_{1-4}$alkoxy, C$_{3-7}$cycloalkyl-C$_{1-4}$alkyl, —NR$^7$R$^{7a}$, carbonyl, —COOR$^{6a}$, —COOH, —COR$^{7b}$, —CH(OH)R$^{7c}$, —CH(OR$^{6g}$)R$^{7d}$, —CONR$^7$R$^{7a}$, —NHCOR$^{6b}$, —NHSO$_2$R$^{6c}$, —NHSO$_2$aryl, aryl, —SR$^{6d}$, —SOR$^{6e}$, —SO$_2$R$^{6f}$, —SO$_2$aryl, or
$R^1$ and $R^2$ together with carbon atoms attached thereto form a ring or a 3-14 membered heterocyclic ring containing 1-4 heteroatoms selected from N, O, S, SO and/or SO$_2$;

$R^3$ represents $OR^8$, a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$;

$R^4$, $R^{5a}$, $R^{5b}$ and $R^{5c}$ respectively represent hydrogen, $(C_{1-18}$-alkyl)carbonyl, $(C_{1-18}$-alkyl)oxycarbonyl, arylcarbonyl, or aryl-$(C_{1-3}$alkyl)carbonyl;

$R^8$ represents a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$;

$R^6$, $R^{6a}$, $R^{6b}$, $R^{6c}$, $R^{6d}$, $R^{6e}$ and $R^{6f}$ respectively represent alkyl or cycloalkyl, or alkyl or cycloalkyl in which one or more carbon atoms are replaced with one or more heteroatoms selected from N, O, S, SO and/or $SO_2$;

$R^7$, $R^{7a}$, $R^{7b}$, $R^{7c}$ and $R^{7d}$ respectively represent hydrogen, alkyl, aryl, alkylaryl or cycloalkyl, or $R^7$ and $R^{7a}$ together with the nitrogen attached thereto form a 3-14 membered heterocyclyl containing 1-4 heteroatoms selected from N, O, S, SO and/or $SO_2$;

X represents a chemical bond, NH, O, S, SO, $SO_2$ or an alkylene, said alkylene can be further substituted by one or more substituents, which comprise halogen, hydroxyl, $C_{1-4}$alkyl, cycloalkyl, $C_{1-4}$alkoxy, and $C_{1-4}$alkyl that is substituted by halogen;

wherein the alkyl, the cycloalkyl, the aryl, the heterocyclyl, the spiro-ring group, the bridged-ring group, and the fused-ring group can be further substituted by one or more substituents, which comprise halogen, hydroxyl, amino, carboxyl, alkyl, alkoxy, aminosulfonyl, carbamoyl, $C_{1-4}$alkoxy that is substituted by halogen, and $C_{1-4}$alkyl that is substituted by halogen, hydroxyl, amino, and/or carboxyl; preferably wherein, $R^1$ represents hydrogen, —OH, —$OR^6$, alkyl, —$CF_3$, —$OCHF_2$, —$OCF_3$, halogen or —CN;

$R^2$ represents hydrogen;

$R^3$ represents $OR^8$, a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$;

$R^4$, $R^{5a}$, $R^{5b}$ and $R^{5c}$ respectively represent hydrogen, $(C_{1-18}$-alkyl)carbonyl, $(C_{1-18}$-alkyl)oxycarbonyl, arylcarbonyl, or aryl-$(C_{1-3}$alkyl)carbonyl;

$R^8$ represents a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$;

$R^6$, $R^{6a}$, $R^{6b}$, $R^{6c}$, $R^{6d}$, $R^{6e}$ and $R^{6f}$ respectively represent alkyl or cycloalkyl, or alkyl or cycloalkyl in which one or more carbon atoms are replaced with one or more heteroatoms selected from N, O, S, SO and/or $SO_2$;

$R^7$, $R^{7a}$, $R^{7b}$, $R^{7c}$ and $R^{7d}$ respectively represent hydrogen, alkyl, aryl, alkylaryl or cycloalkyl, or $R^7$ and $R^{7a}$ together with the nitrogen attached thereto form a 3-14 membered heterocyclyl containing 1-4 heteroatoms selected from N, O, S, SO and/or $SO_2$;

X represents a chemical bond or an alkylene, said alkylene can be further substituted by one or more substituents, which comprise halogen, hydroxyl, $C_{1-4}$alkyl, $C_{1-4}$alkoxy, $C_{1-4}$alkyl that is substituted by halogen;

wherein the alkyl, the cycloalkyl, the aryl, the heterocyclyl, the spiro-ring group, the bridged-ring group, and the fused-ring group can be further substituted by one or more substituents, which comprise halogen, hydroxyl, amino, carboxyl, alkyl, alkoxy, aminosulfonyl, carbamoyl, $C_{1-4}$alkoxy that is substituted by halogen, and $C_{1-4}$alkyl that is substituted by halogen, hydroxyl, amino, and/or carboxyl; preferably wherein, $R^1$ represents hydrogen, —OH, —$OR^6$, alkyl, —$CF_3$, —$OCHF_2$, —$OCF_3$, halogen or —CN;

$R^2$ represents hydrogen;

$R^3$ represents $OR^8$, a 7-12 membered spiro-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$;

$R^8$ represents a 7-12 membered spiro-ring group, a 6-12 membered fused-ring group, or a 7-12 membered spiro-ring group or a 6-12 membered fused-ring group in which one or more carbon atoms are replaced with one or more heteroatoms selected from N, O, S, SO and/or $SO_2$;

$R^4$, $R^{5a}$, $R^{5b}$ and $R^{5c}$ respectively represent hydrogen;

X is methylene;

wherein the spiro-ring group, the fused-ring group and the heterocyclyl can be further substituted by one or more substituents, which comprise halogen, hydroxyl, amino, carboxyl, alkyl, alkoxy, aminosulfonyl, carbamoyl, $C_{1-4}$alkoxy that is substituted by halogen, and $C_{1-4}$alkyl that is substituted by halogen, hydroxyl, amino, and/or carboxyl; preferably wherein, $R^1$ represents halogen or —CN;

$R^2$ represents hydrogen;

$R^3$ represents $OR^8$, a 7-12 membered spiro-ring group or a 7-12 membered spiro-ring group containing 1-2 heteroatoms selected from N, O, S, SO and/or $SO_2$;

$R^8$ represents a 7-12 membered spiro-ring group, a 6-12 membered fused-ring group, or a 7-12 membered spiro-ring group or a 6-12 membered fused-ring group in which one or more carbon atoms are replaced with one or more heteroatoms selected from N, O, S, SO and/or $SO_2$;

$R^4$, $R^{5a}$, $R^{5b}$ and $R^{5c}$ respectively represent hydrogen;

X is methylene;

wherein the spiro-ring group, the fused-ring group and the heterocyclyl can be further substituted by one or more substituents, which comprise halogen, hydroxyl, amino, carboxyl, $C_{1-6}$alkyl, $C_{1-6}$alkoxy, aminosulfonyl, carbamoyl; further preferably wherein, $R^1$ represents halogen or —CN;

$R^2$ represents hydrogen;

$R^3$ represents $OR^8$, a 7-10 membered spiro-ring group or a 7-10 membered spiro-ring group containing 1-2 heteroatoms selected from N, O, S, SO and/or $SO_2$;

$R^8$ represents a 7-10 membered spiro-ring group, a 6-10 membered fused-ring group, or a 7-10 membered spiro-ring group or a 6-10 membered fused-ring group in which one or more carbon atoms are replaced with one or more heteroatoms selected from N, O, S, SO and/or $SO_2$;

$R^4$, $R^{5a}$, $R^{5b}$ and $R^{5c}$ respectively represent hydrogen;
X is methylene;
further preferably wherein,
$R^1$ represents halogen;
$R^2$ represents hydrogen;
$R^3$ represents $OR^8$, a 7-10 membered spiro-ring group;
$R^8$ represents a 7-10 membered spiro-ring group, a 6-10 membered fused-ring group, or a 7-10 membered spiro-ring group or a 6-10 membered fused-ring group in which one or more carbon atoms are replaced with one or more heteroatoms selected from N, O, S, SO and/or $SO_2$;
$R^4$, $R^{5a}$, $R^{5b}$, and $R^{5c}$ respectively represent hydrogen;
X is methylene.

Another technical solution of the present invention is as follows:

A compound represented by general formula (I), a pharmaceutically acceptable salt thereof, an easily hydrolyzable ester thereof or a stereoisomer thereof:

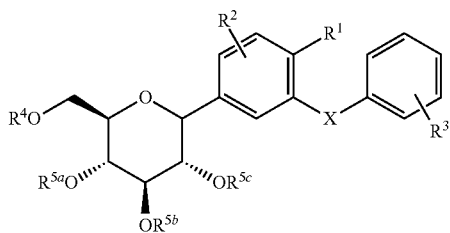

(I)

wherein,
$R^1$ and $R^2$ each independently represent hydrogen, —OH, —$OR^6$, alkyl, —$CF_3$, —$OCHF_2$, —$OCF_3$, halogen, —CN, $C_{2-6}$alkynyl, $C_{2-6}$ alkenyl, cycloalkyl, $C_{2-4}$alkenyl-$C_{1-4}$alkyl, $C_{2-4}$alkynyl-$C_{1-4}$alkyl, $C_{2-4}$alkenyl-$C_{1-4}$alkoxy, $C_{2-4}$alkynyl-$C_{1-4}$ alkoxy, $C_{3-7}$cycloalkyl-$C_{1-4}$alkyl, —$NR^7R^{7a}$, carbonyl, —$COOR^{6a}$, —COOH, —$CH(OH)R^{7a}$, —$CH(OR^{6g})R^{7d}$, —$CONR^7R^{7a}$, —$NHCOR^{6b}$, —$NHSO_2R^{6c}$, —$NHSO_2$aryl, aryl, —$SR^{6d}$, —$SOR^{6e}$, —$SO_2R^{6f}$, —$SO_2$aryl, or
$R^1$ and $R^2$ together with carbon atoms attached thereto form a ring or a 3-14 membered heterocyclic ring containing 1-4 heteroatoms selected from N, O, S, SO and/or $SO_2$,
$R^6$, $R^{6a}$, $R^{6b}$, $R^{6c}$, $R^{6d}$, $R^{6e}$ and $R^{6f}$ respectively represent alkyl or cycloalkyl, or alkyl or cycloalkyl in which one or more carbon atoms are replaced with one or more heteroatoms selected from N, O, S, SO and/or $SO_2$;
$R^7$, $R^{7a}$, $R^{7b}$, $R^{7c}$ and $R^{7d}$ respectively represent hydrogen, alkyl, aryl, alkylaryl or cycloalkyl, or $R^7$ and $R^{7a}$ together with the nitrogen attached thereto form a 3-14 membered heterocyclyl containing 1-4 heteroatoms selected from N, O, S, SO and/or $SO_2$;
further preferably
$R^1$ represents halogen;
$R^2$ represents hydrogen;
$R^3$ represents $OR^8$, a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$; preferably $R^3$ represents $OR^8$, a 7-12 membered spiro-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$; further preferably $R^3$ represents $OR^8$, a 7-12 membered spiro-ring group or a 7-12 membered spiro-ring group containing 1-2 heteroatoms selected from N, O, S, SO and/or $SO_2$; more further preferably $R^3$ represents $OR^8$, a 7-10 membered spiro-ring group or a 7-10 membered spiro-ring group containing 1-2 heteroatoms selected from N, O, S, SO and/or $SO_2$; more further preferably $R^3$ represents:

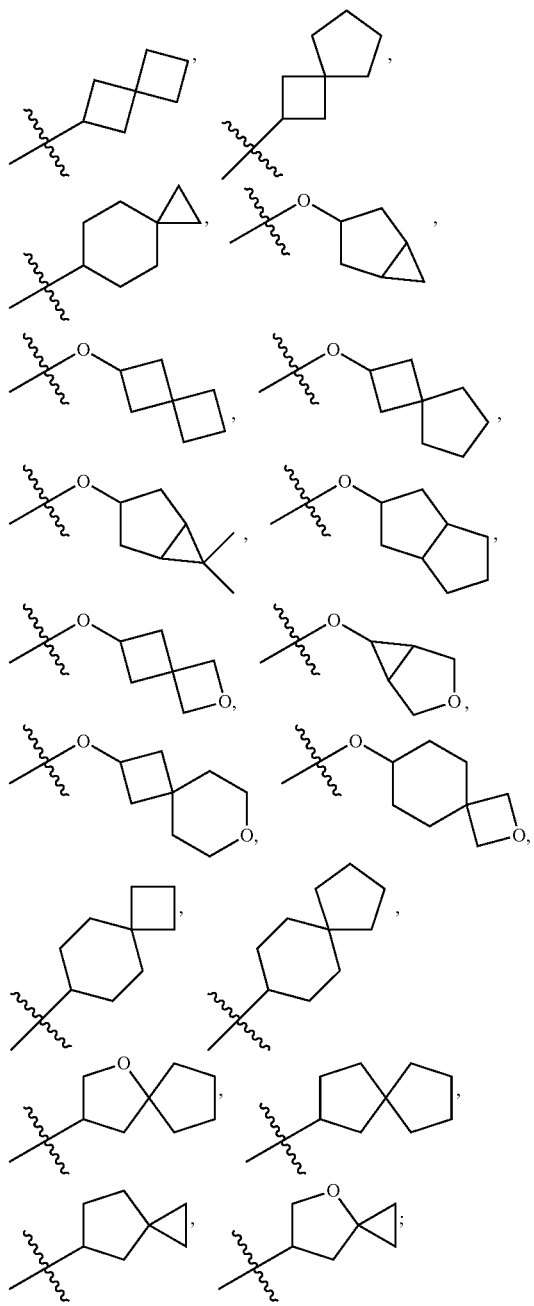

$R^4$, $R^{5a}$, $R^{5b}$ and $R^{5c}$ respectively represent hydrogen, ($C_{1-18}$-alkyl)carbonyl, ($C_{1-18}$-alkyl)oxycarbonyl, arylcarbonyl, or aryl-($C_{1-3}$alkyl)carbonyl; preferably $R^4$, $R^{5a}$, $R^{5b}$ and $R^{5c}$ respectively represent hydrogen, ($C_{1-6}$-alkyl)carbonyl, ($C_{1-6}$-alkyl)oxycarbonyl; preferably $R^4$, $R^{5a}$, $R^{5b}$ and $R^{5c}$ respectively represent hydrogen, ($C_{1-3}$-alkyl)carbonyl; further preferably $R^4$, $R^{5a}$, $R^{5b}$ and $R^{5c}$ respectively represent hydrogen;

$R^8$ represents a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or $SO_2$; preferably $R^8$ represents a 7-12 membered spiro-ring group, a 6-12 membered fused-ring group, or a 7-12 membered spiro-ring group or a 6-12 membered fused-ring group in which one or more carbon atoms are replaced with one or more heteroatoms selected from N, O, S, SO and/or $SO_2$; further preferably $R^8$ represents a 7-12 membered spiro-ring group, a 6-12 membered fused-ring group, or a 7-12 membered spiro-ring group or a 6-12 membered fused-ring group in which 1-2 carbon atoms are replaced with 1-2 heteroatoms selected from N, O, S, SO and/or $SO_2$; further preferably $R^8$ represents a 7-10 membered spiro-ring group, a 6-10 membered fused-ring group, or a 7-10 membered spiro-ring group or a 6-10 membered fused-ring group in which 1-2 carbon atoms are replaced with 1-2 heteroatoms selected from N, O, S, SO and/or $SO_2$;

X represents a chemical bond, NH, O, S, SO, $SO_2$ or an alkylene, said alkylene can be further substituted by one or more substituents, which comprise halogen, hydroxyl, $C_{1-4}$alkyl, cycloalkyl, $C_{1-4}$alkoxy, $C_{1-4}$alkyl that is substituted by halogen; preferably X represents a chemical bond or an alkylene, said alkylene can be further substituted by one or more substituents, which comprise halogen, hydroxyl, $C_{1-4}$alkyl, $C_{1-4}$alkoxy, $C_{1-4}$alkyl that is substituted by halogen; further preferably X is methylene;

wherein the alkyl, the cycloalkyl, the aryl, the heterocyclyl, the spiro-ring group, the bridged-ring group, and the fused-ring group, as mentioned above, can be further substituted by one or more substituents, which comprise halogen, hydroxyl, amino, carboxyl, alkyl, alkoxy, aminosulfonyl, carbamoyl, $C_{1-4}$alkoxy that is substituted by halogen, and $C_{1-4}$alkyl that is substituted by halogen, hydroxyl, amino and/or carboxyl; preferably can be further substituted by 1-3 substituents, which comprise halogen, hydroxyl, amino, carboxyl, alkyl, alkoxy, aminosulfonyl, carbamoyl, $C_{1-4}$alkoxy that is substituted by halogen, and $C_{1-4}$alkyl that is substituted by halogen, hydroxyl, amino and/or carboxyl; further preferably can be further substituted by 1-2 substituents, which comprise halogen, hydroxyl, amino, carboxyl, $C_{1-4}$alkyl, $C_{1-4}$alkoxy, aminosulfonyl, carbamoyl, $C_{1-4}$alkoxy that is substituted by halogen, and $C_{1-4}$alkyl that is substituted by halogen, hydroxyl, amino and/or carboxyl; further preferably can be further substituted by one substituent, which comprises halogen, hydroxyl, amino, carboxyl, $C_{1-4}$alkyl, $C_{1-4}$alkoxy, aminosulfonyl, carbamoyl, $C_{1-4}$alkoxy that is substituted by halogen, and $C_{1-4}$alkyl that is substituted by halogen, hydroxyl, amino and/or carboxyl.

Particularly preferable compounds are as follows:

| Nos. | Chemical Structures |
| --- | --- |
| 1 | 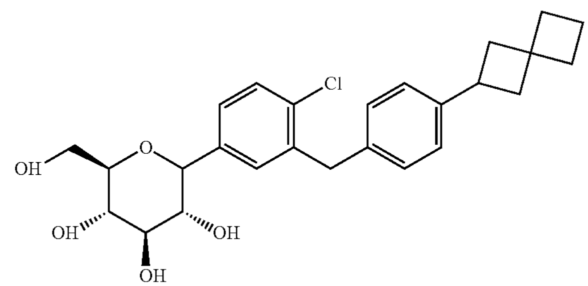 [SMILES: OC[C@H]1OC(c2ccc(Cl)c(Cc3ccc(C4CC5(CCC5)C4)cc3)c2)[C@H](O)[C@@H](O)[C@@H]1O] |
| 2 | 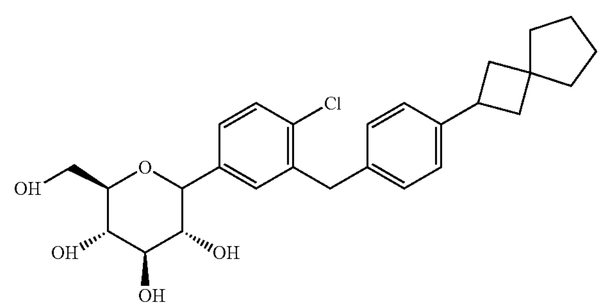 [SMILES: OC[C@H]1OC(c2ccc(Cl)c(Cc3ccc(C4CC5(CCCC5)C4)cc3)c2)[C@H](O)[C@@H](O)[C@@H]1O] |
| 4 | 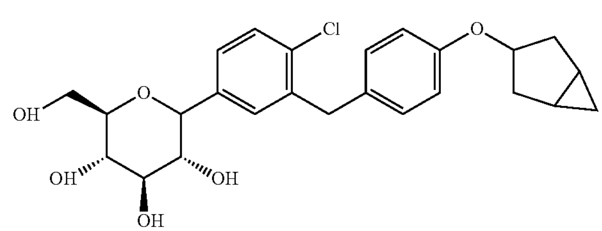 [SMILES: OC[C@H]1OC(c2ccc(Cl)c(Cc3ccc(OC4CC5CC5C4)cc3)c2)[C@H](O)[C@@H](O)[C@@H]1O] |

-continued

| Nos. | Chemical Structures |
|---|---|
| 5 | 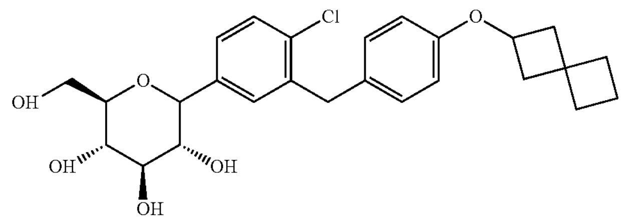 [SMILES: OC[C@H]1OC(c2ccc(Cl)c(Cc3ccc(OC4CC5(CCC5)C4)cc3)c2)[C@H](O)[C@@H](O)[C@@H]1O] |
| 6 | 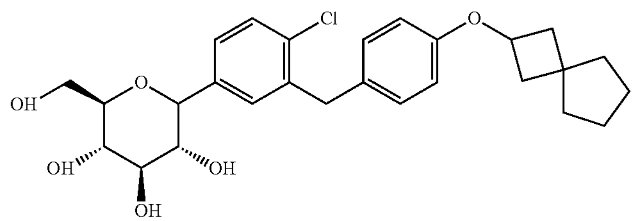 [SMILES: OC[C@H]1OC(c2ccc(Cl)c(Cc3ccc(OC4CC5(CCCC5)C4)cc3)c2)[C@H](O)[C@@H](O)[C@@H]1O] |
| 7 | 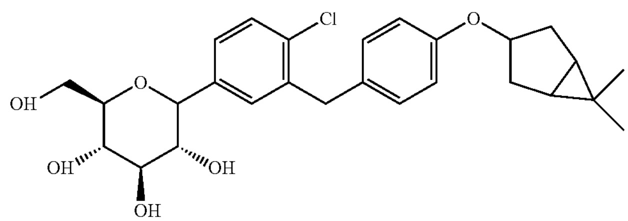 [SMILES: CC1(C)C2CC(Oc3ccc(Cc4cc(C5O[C@H](CO)[C@@H](O)[C@H](O)[C@H]5O)ccc4Cl)cc3)CC21] |
| 8 | 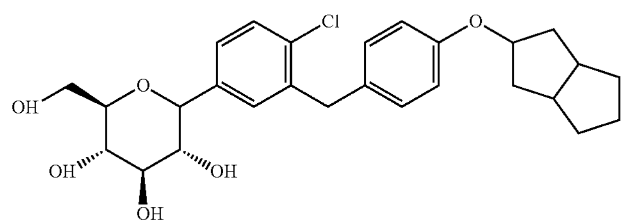 [SMILES: OC[C@H]1OC(c2ccc(Cl)c(Cc3ccc(OC4CC5CCCC5C4)cc3)c2)[C@H](O)[C@@H](O)[C@@H]1O] |
| 9 | 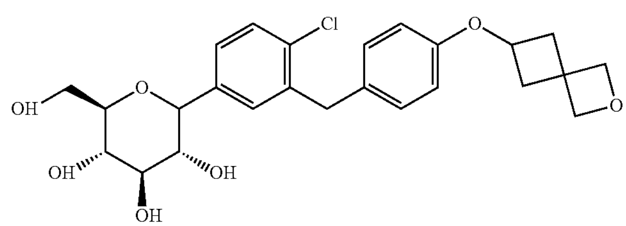 [SMILES: OC[C@H]1OC(c2ccc(Cl)c(Cc3ccc(OC4CC5(COC5)C4)cc3)c2)[C@H](O)[C@@H](O)[C@@H]1O] |
| 10 | 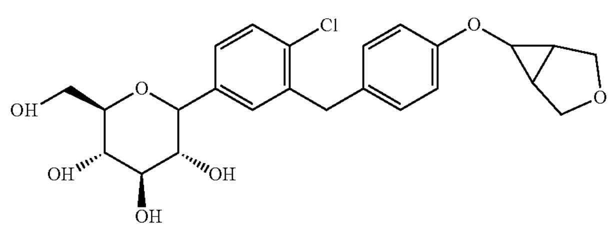 [SMILES: OC[C@H]1OC(c2ccc(Cl)c(Cc3ccc(OC4C5COCC54)cc3)c2)[C@H](O)[C@@H](O)[C@@H]1O] |
| 11 | 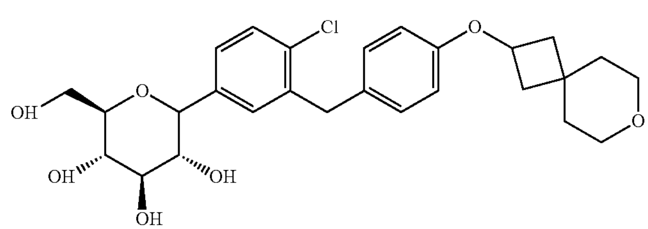 [SMILES: OC[C@H]1OC(c2ccc(Cl)c(Cc3ccc(OC4CC5(CCOCC5)C4)cc3)c2)[C@H](O)[C@@H](O)[C@@H]1O] |

-continued
| Nos. | Chemical Structures |
|---|---|
| 12 | 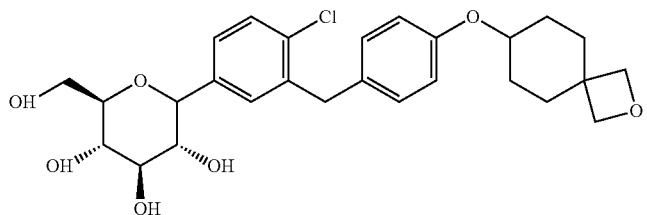 [SMILES: OC[C@H]1OC(c2ccc(Cl)c(Cc3ccc(OC4CCC5(CC4)COC5)cc3)c2)[C@H](O)[C@@H](O)[C@@H]1O] |
| 13 | 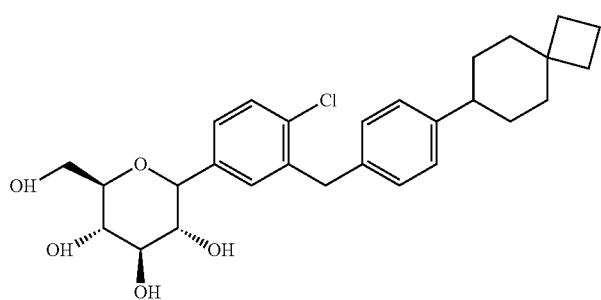 |
| 14 | 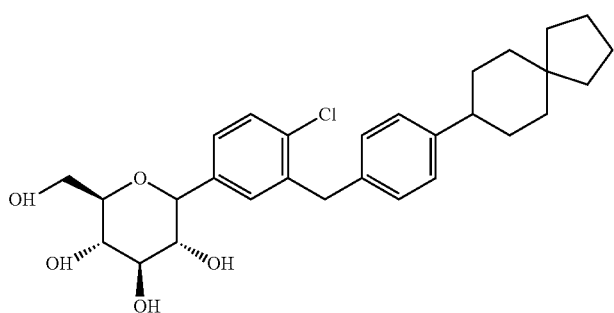 |
| 15 | 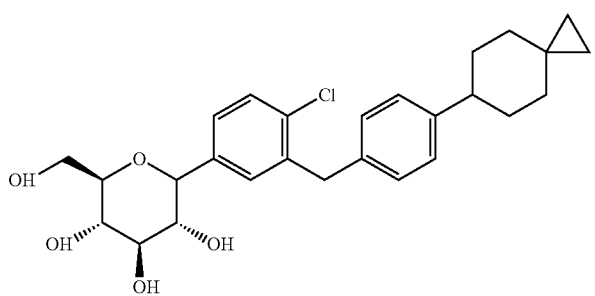 [SMILES: OC[C@H]1OC(c2ccc(Cl)c(Cc3ccc(C4CCC5(CC4)CC5)cc3)c2)[C@H](O)[C@@H](O)[C@@H]1O] |
| 16 | 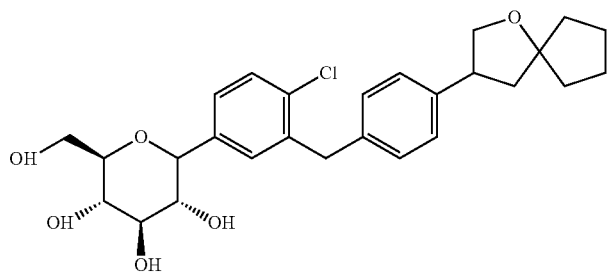 [SMILES: OC[C@H]1OC(c2ccc(Cl)c(Cc3ccc(C4COC5(CCCC5)C4)cc3)c2)[C@H](O)[C@@H](O)[C@@H]1O] |

-continued
| Nos. | Chemical Structures |
|---|---|
| 17 | 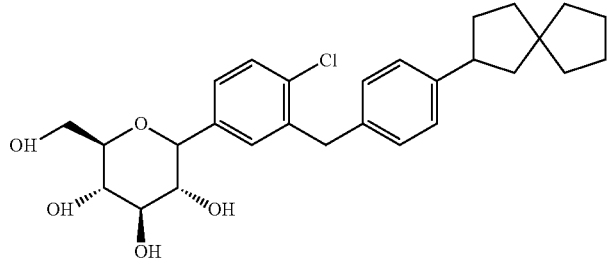 [SMILES: OC[C@H]1OC(c2ccc(Cl)c(Cc3ccc(C4CCC5(CCCC5)C4)cc3)c2)[C@H](O)[C@@H](O)[C@@H]1O] |
| 18 | 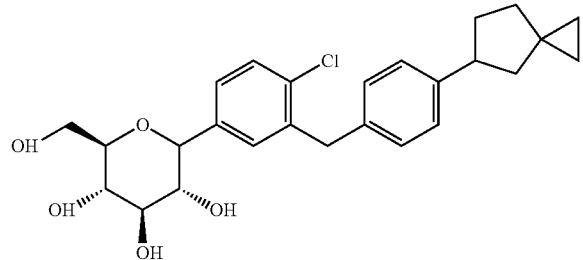 [SMILES: OC[C@H]1OC(c2ccc(Cl)c(Cc3ccc(C4CCC5(CC5)C4)cc3)c2)[C@H](O)[C@@H](O)[C@@H]1O] |
| 19 | 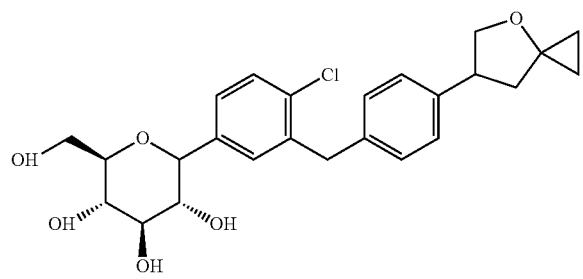 [SMILES: OC[C@H]1OC(c2ccc(Cl)c(Cc3ccc(C4COC5(CC5)C4)cc3)c2)[C@H](O)[C@@H](O)[C@@H]1O] |
| 38 | 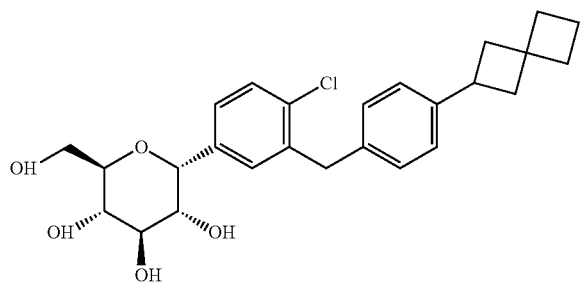 [SMILES: OC[C@H]1O[C@H](c2ccc(Cl)c(Cc3ccc(C4CC5(CCC5)C4)cc3)c2)[C@H](O)[C@@H](O)[C@@H]1O] |
| 39 | 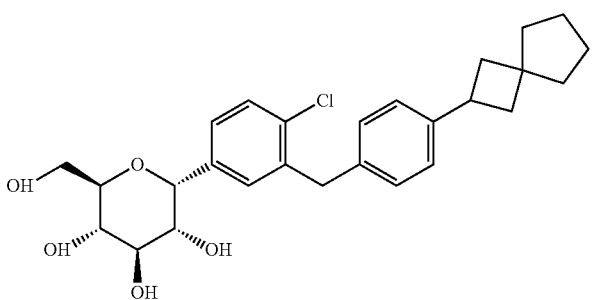 [SMILES: OC[C@H]1O[C@H](c2ccc(Cl)c(Cc3ccc(C4CC5(CCCC5)C4)cc3)c2)[C@H](O)[C@@H](O)[C@@H]1O] |

-continued

| Nos. | Chemical Structures |
|---|---|
| 40 | 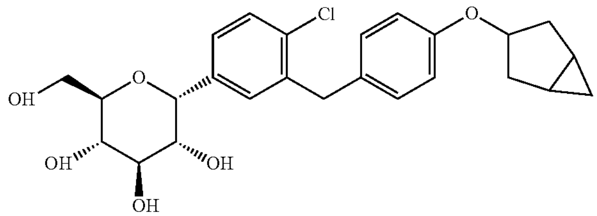 [SMILES: OC[C@H]1O[C@H](c2ccc(Cl)c(Cc3ccc(OC4CC5CC5C4)cc3)c2)[C@H](O)[C@@H](O)[C@@H]1O] |
| 41 | 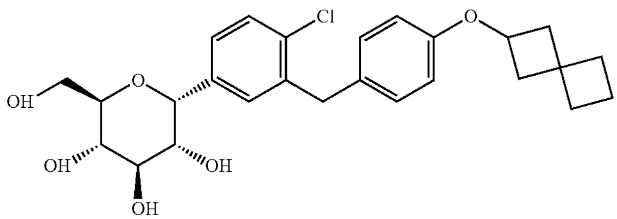 |
| 42 | 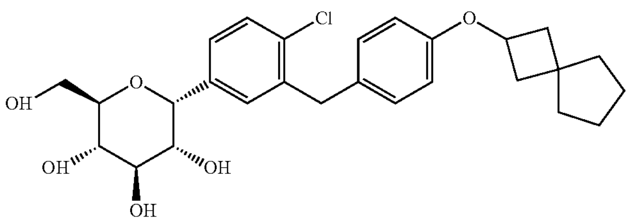 |
| 43 | 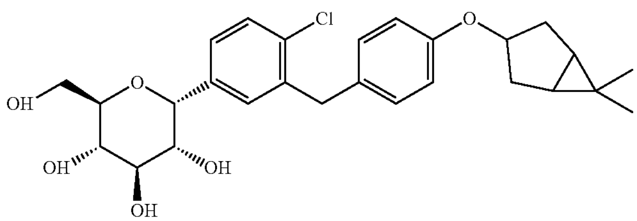 [SMILES: CC1(C)C2CC(Oc3ccc(Cc4cc([C@H]5O[C@H](CO)[C@@H](O)[C@H](O)[C@H]5O)ccc4Cl)cc3)CC21] |
| 44 | 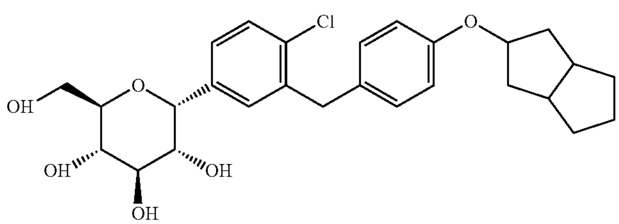 [SMILES: OC[C@H]1O[C@H](c2ccc(Cl)c(Cc3ccc(OC4CC5CCCC5C4)cc3)c2)[C@H](O)[C@@H](O)[C@@H]1O] |
| 45 | 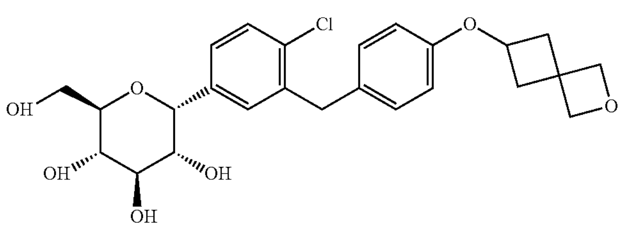 |
| 46 | 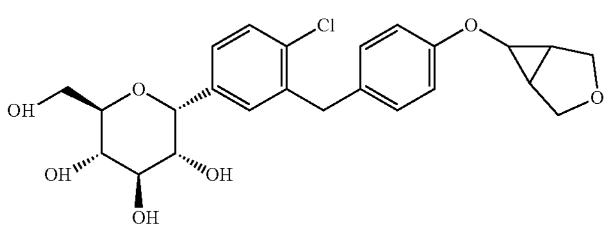 [SMILES: OC[C@H]1O[C@H](c2ccc(Cl)c(Cc3ccc(OC4C5COCC54)cc3)c2)[C@H](O)[C@@H](O)[C@@H]1O] |

-continued
| Nos. | Chemical Structures |
|---|---|
| 20 | 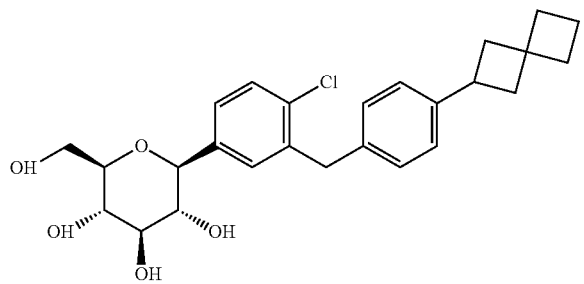 [SMILES: OC[C@H]1O[C@@H](c2ccc(Cl)c(Cc3ccc(C4CC5(CCC5)C4)cc3)c2)[C@H](O)[C@@H](O)[C@@H]1O] |
| 21 | 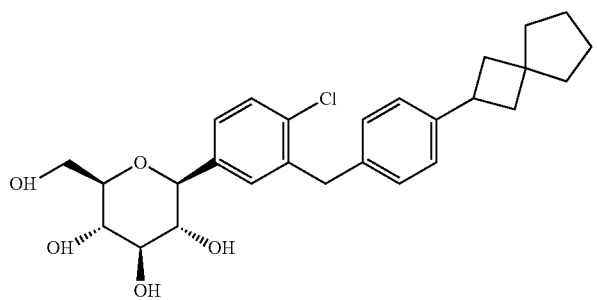 [SMILES: OC[C@H]1O[C@@H](c2ccc(Cl)c(Cc3ccc(C4CC5(CCCC5)C4)cc3)c2)[C@H](O)[C@@H](O)[C@@H]1O] |
| 22 | 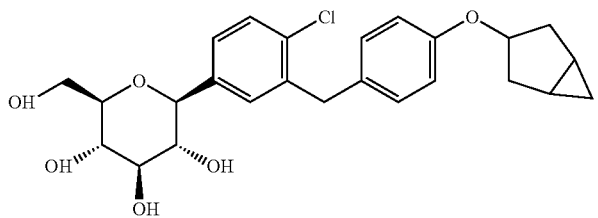 [SMILES: OC[C@H]1O[C@@H](c2ccc(Cl)c(Cc3ccc(OC4CC5CC5C4)cc3)c2)[C@H](O)[C@@H](O)[C@@H]1O] |
| 23 | 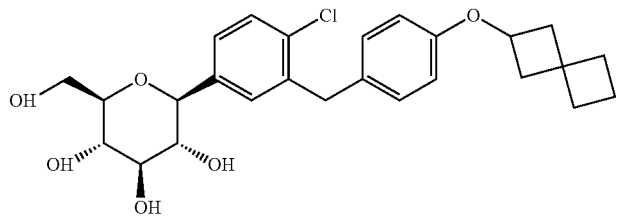 [SMILES: OC[C@H]1O[C@@H](c2ccc(Cl)c(Cc3ccc(OC4CC5(CCC5)C4)cc3)c2)[C@H](O)[C@@H](O)[C@@H]1O] |
| 24 | 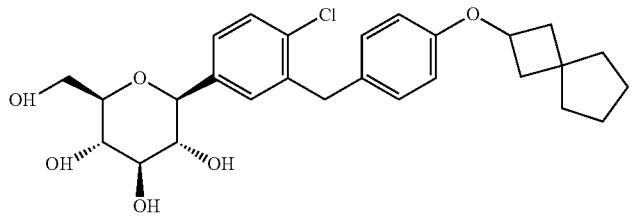 [SMILES: OC[C@H]1O[C@@H](c2ccc(Cl)c(Cc3ccc(OC4CC5(CCCC5)C4)cc3)c2)[C@H](O)[C@@H](O)[C@@H]1O] |
| 25 | 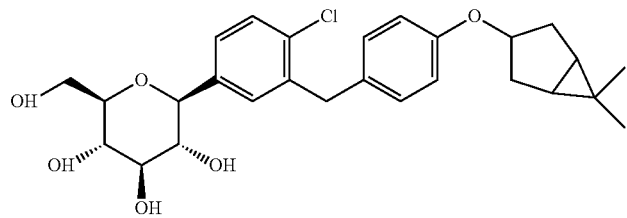 [SMILES: CC1(C)C2CC(Oc3ccc(Cc4cc([C@@H]5O[C@H](CO)[C@@H](O)[C@H](O)[C@H]5O)ccc4Cl)cc3)CC21] |

-continued
| Nos. | Chemical Structures |
|---|---|
| 26 | 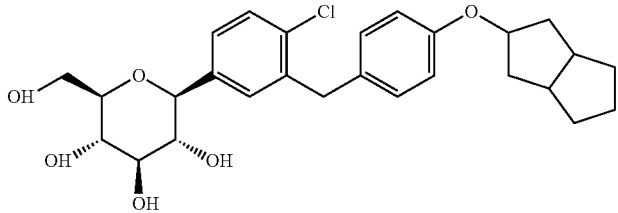 [SMILES: OC[C@H]1O[C@@H](c2ccc(Cl)c(Cc3ccc(OC4CC5CCCC5C4)cc3)c2)[C@H](O)[C@@H](O)[C@@H]1O] |
| 27 | 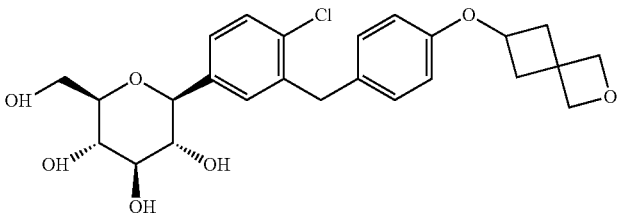 [SMILES: OC[C@H]1O[C@@H](c2ccc(Cl)c(Cc3ccc(OC4CC5(COC5)C4)cc3)c2)[C@H](O)[C@@H](O)[C@@H]1O] |
| 28 | 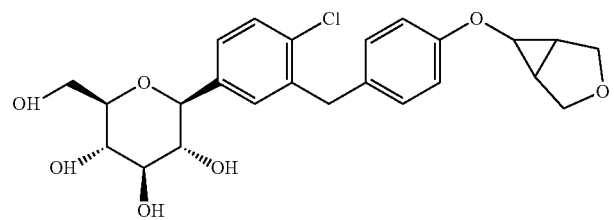 [SMILES: OC[C@H]1O[C@@H](c2ccc(Cl)c(Cc3ccc(OC4C5COCC54)cc3)c2)[C@H](O)[C@@H](O)[C@@H]1O] |
| 29 | 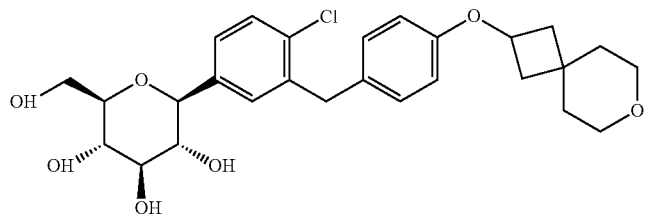 [SMILES: OC[C@H]1O[C@@H](c2ccc(Cl)c(Cc3ccc(OC4CC5(CCOCC5)C4)cc3)c2)[C@H](O)[C@@H](O)[C@@H]1O] |
| 30 | 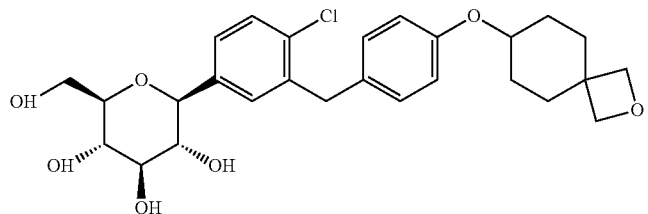 [SMILES: OC[C@H]1O[C@@H](c2ccc(Cl)c(Cc3ccc(OC4CCC5(CC4)COC5)cc3)c2)[C@H](O)[C@@H](O)[C@@H]1O] |
| 31 | 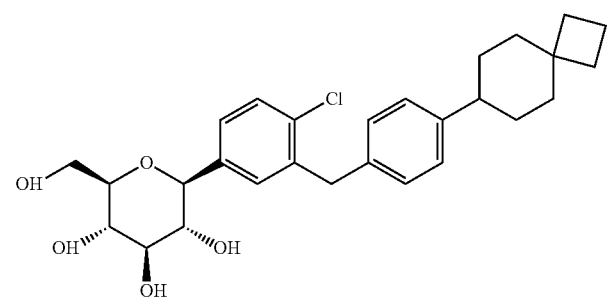 [SMILES: OC[C@H]1O[C@@H](c2ccc(Cl)c(Cc3ccc(C4CCC5(CCC5)CC4)cc3)c2)[C@H](O)[C@@H](O)[C@@H]1O] |

-continued
| Nos. | Chemical Structures |
|---|---|
| 32 | 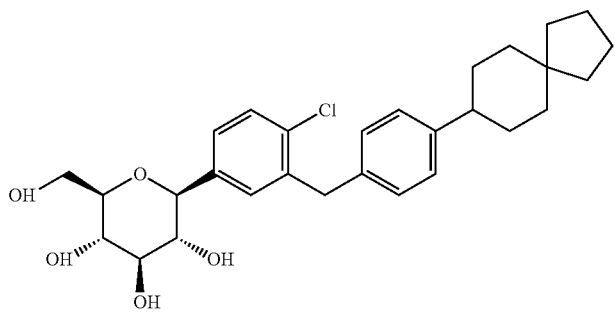 [SMILES: OC[C@H]1O[C@@H](c2ccc(Cl)c(Cc3ccc(C4CCC5(CCCC5)CC4)cc3)c2)[C@H](O)[C@@H](O)[C@@H]1O] |
| 33 | 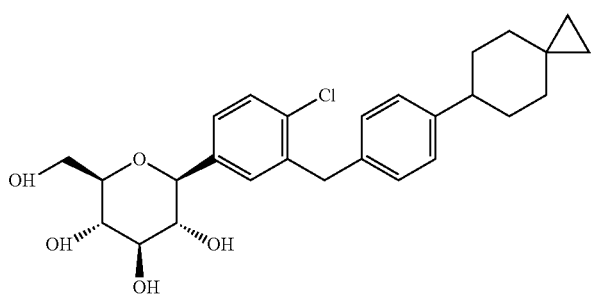 [SMILES: OC[C@H]1O[C@@H](c2ccc(Cl)c(Cc3ccc(C4CCC5(CC4)CC5)cc3)c2)[C@H](O)[C@@H](O)[C@@H]1O] |
| 34 | 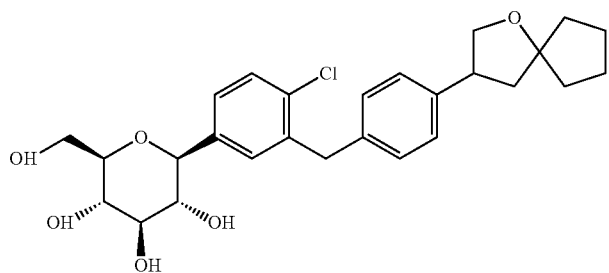 [SMILES: OC[C@H]1O[C@@H](c2ccc(Cl)c(Cc3ccc(C4COC5(CCCC5)C4)cc3)c2)[C@H](O)[C@@H](O)[C@@H]1O] |
| 35 | 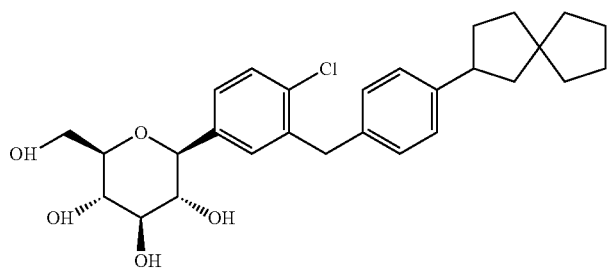 [SMILES: OC[C@H]1O[C@@H](c2ccc(Cl)c(Cc3ccc(C4CCC5(CCCC5)C4)cc3)c2)[C@H](O)[C@@H](O)[C@@H]1O] |
| 36 | 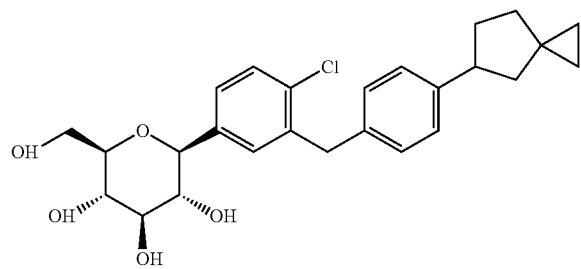 [SMILES: OC[C@H]1O[C@@H](c2ccc(Cl)c(Cc3ccc(C4CCC5(CC5)C4)cc3)c2)[C@H](O)[C@@H](O)[C@@H]1O] |

-continued
| Nos. | Chemical Structures |
|---|---|
| 37 | 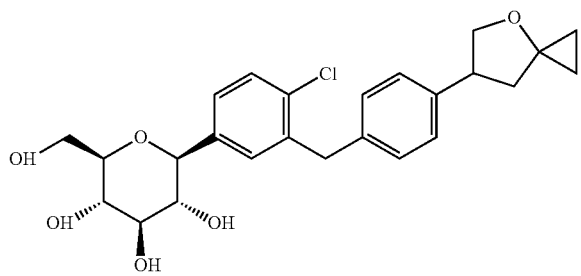 [SMILES: OC[C@H]1O[C@@H](c2ccc(Cl)c(Cc3ccc(C4COC5(CC5)C4)cc3)c2)[C@H](O)[C@@H](O)[C@@H]1O] |
| 47 | 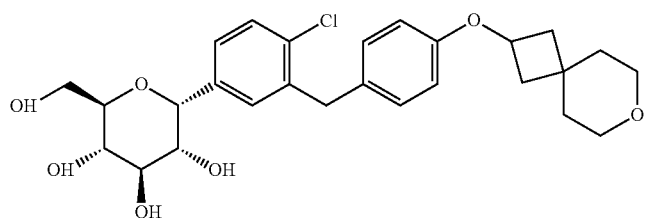 |
| 48 | 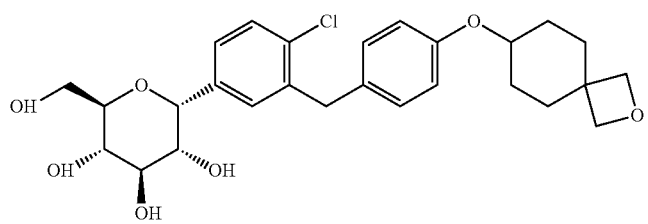 |
| 49 | 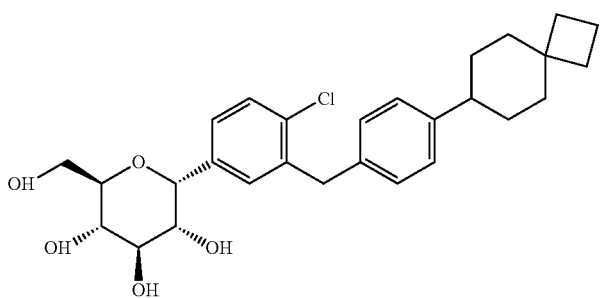 [SMILES: OC[C@H]1O[C@H](c2ccc(Cl)c(Cc3ccc(C4CCC5(CCC5)CC4)cc3)c2)[C@H](O)[C@@H](O)[C@@H]1O] |
| 50 | 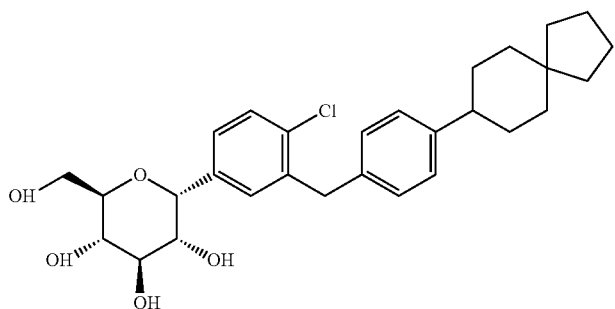 [SMILES: OC[C@H]1O[C@H](c2ccc(Cl)c(Cc3ccc(C4CCC5(CCCC5)CC4)cc3)c2)[C@H](O)[C@@H](O)[C@@H]1O] |

-continued

| Nos. | Chemical Structures |
|------|---------------------|
| 51 | 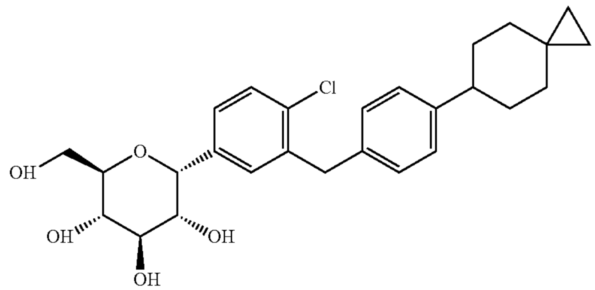 [SMILES: OC[C@H]1O[C@H](c2ccc(Cl)c(Cc3ccc(C4CCC5(CC4)CC5)cc3)c2)[C@H](O)[C@@H](O)[C@@H]1O] |
| 52 | 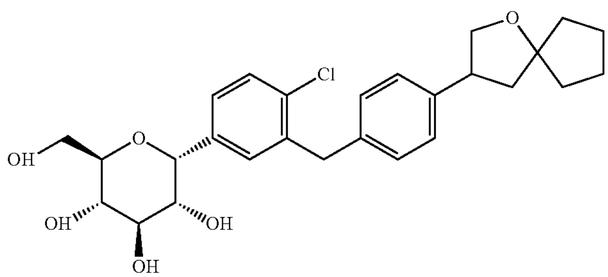 |
| 53 | 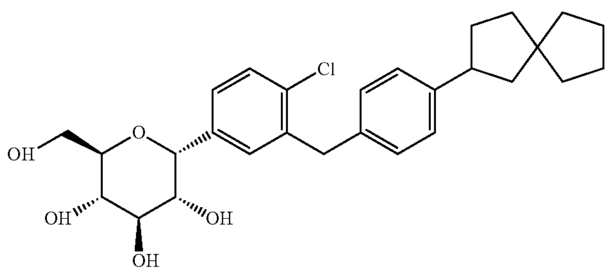 [SMILES: OC[C@H]1O[C@H](c2ccc(Cl)c(Cc3ccc(C4CCC5(CCCC5)C4)cc3)c2)[C@H](O)[C@@H](O)[C@@H]1O] |
| 54 | 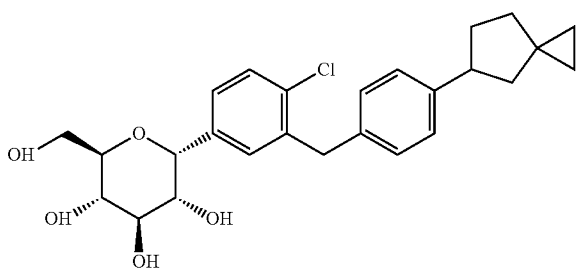 [SMILES: OC[C@H]1O[C@H](c2ccc(Cl)c(Cc3ccc(C4CCC5(CC5)C4)cc3)c2)[C@H](O)[C@@H](O)[C@@H]1O] |
| 55 | 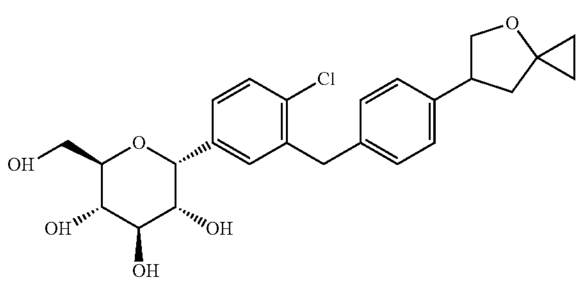 [SMILES: OC[C@H]1O[C@H](c2ccc(Cl)c(Cc3ccc(C4COC5(CC5)C4)cc3)c2)[C@H](O)[C@@H](O)[C@@H]1O] |

DETAILED DESCRIPTION OF THE INVENTION

As used herein, "halogen" includes fluoro, chloro, bromo and iodo, preferably fluoro and chloro.

As used herein, "alkyl" refers to a straight-chain or branched chain alkyl derived from an alkane having 1-18 carbon atoms by removing one hydrogen atom, e.g. methyl, ethyl, n-propyl, iso-propyl, n-butyl, iso-butyl, sec-butyl, tert-butyl, n-pentyl, iso-pentyl, 2-methylbutyl, 3-methylbutyl, 1,1-dimethylpropyl, 1,2-dimethylpropyl, neo-pentyl, 1-ethylpropyl, n-hexyl, iso-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. $C_{1-6}$alkyl is preferable, $C_{1-4}$alkyl and $C_{1-3}$alkyl are more preferable. The term "$C_{1-18}$alkyl", "$C_{1-6}$alkyl", "$C_{1-4}$alkyl", and "$C_{1-3}$alkyl" refers to the specific examples containing 1-18, 1-6, 1-4, 1-3 carbon atoms in the above examples.

As used herein, "alkylene" refers to the above alkyl but being derived by removing two hydrogen atoms, including —(CH$_2$)$_t$— (t is an integer of 1-18), e.g. methylene, ethylene, propylene and the like.

As used herein, "$C_{2-6}$alkenyl" refers to a straight-chain or branched chain alkenyl having 2-6 carbon atoms and containing a double bond, e.g. ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,3-pentadienyl, 1,4-pentadienyl, 1,4-hexadienyl and the like. $C_{2-4}$alkenyl is preferable. The term "$C_{2-4}$alkenyl" refers to the specific examples containing 2-4 carbon atoms in the above examples.

As used herein, "$C_{2-6}$alkynyl" refers to a straight-chain or branched chain alkynyl having 2-6 carbon atoms and containing a triple bond, e.g., ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, 1-ethyl-1-methyl-2-propynyl and the like. $C_{2-4}$alkynyl is preferable. The term "$C_{2-4}$alkynyl" refers to the specific examples containing 2-4 carbon atoms in the above examples.

As used herein, "$C_{1-4}$alkoxy" refers to a group in which the $C_{1-4}$alkyl is attached to another structure via an oxygen atom, e.g. methoxy, ethoxy, propoxy, isopropoxy, butoxy, isobutoxy, tert-butoxy, sec-butoxy and the like.

As used herein, "$C_{1-6}$alkylcarbonyl" refers to a group in which the $C_{1-6}$alkyl is attached to another structure via a carbonyl, e.g. methylcarbonyl, ethylcarbonyl, propylcarbonyl, isopropylcarbonyl, butylcarbonyl, isobutylcarbonyl, tert-butylcarbonyl, sec-butylcarbonyl, pentylcarbonyl, neo-pentylcarbonyl, hexylcarbonyl and the like.

As used herein, "$C_{1-6}$alkoxycarbonyl" refers to a group in which the $C_{1-6}$ alkoxy is attached to another structure via a carbonyl, e.g. methoxycarbonyl, ethoxycarbonyl, propoxycarbonyl, iso-propoxycarbonyl, butoxycarbonyl, iso-butoxycarbonyl, tert-butoxycarbonyl, sec-butoxycarbonyl, pentoxycarbonyl, neo-pentoxycarbonyl, hexyloxycarbonyl and the like.

As used herein, "cycloalkyl" refers to a cycloalkyl derived from a cycloalkane having 3-14 carbon atoms by removing one hydrogen atom, and includes 3-8 membered monocyclic cycloalkyl, 6-14 membered fused-ring cycloalkyl, 7-12 membered bridged-ring group and 7-12 membered saturated spiro-ring. $C_{3-8}$cycloalkyl, $C_{3-6}$cycloalkyl and $C_{5-6}$cycloalkyl are preferable. The term "$C_{3-8}$ cycloalkyl", "$C_{3-6}$cycloalkyl" and "$C_{5-6}$cycloalkyl" respectively refer to the specific examples containing 3-8, 3-6 and 5-6 carbon atoms in the above examples.

The 3-8 membered monocyclic cycloalkyl includes 3-8 membered saturated monocyclic cycloalkyl and 3-8 membered partially saturated monocyclic cycloalkyl. The 3-8 membered saturated monocyclic cycloalkyl refers to a carbocyclic ring in which the monocyclic ring is completely saturated, and its example includes but is not limited to cyclopropyl, cyclobutyl, cyclopentyl, cyclohexyl, cycloheptyl, cyclooctyl, methylcyclopropyl, dimethylcyclopropyl, methylcyclobutyl, dimethylcyclobutyl, methylcyclopentyl, dimethylcyclopentyl, methylcyclohexyl, dimethylcyclohexyl and the like. The 3-8 membered partially saturated monocyclic cycloalkyl refers to a carbocyclic ring in which the monocyclic ring is partially saturated, and its example includes but is not limited to cyclopropenyl, cyclobutenyl, cyclopentenyl, cyclohexenyl, 1,4-cyclohexadienyl, cycloheptenyl, 1,4-cycloheptandienyl, cyclooctenyl, 1,5-cyclooctadienyl and the like.

The fused-ring group refers to 6-14 membered cyclic group formed by two or more cyclic structures sharing two adjacent carbon atoms with each other, and includes 6-14 membered saturated fused-ring group and 6-14 membered partially saturated fused-ring group. 6-12 membered fused-ring group and 6-10 membered fused-ring group are preferable. 6-14 membered saturated fused-ring cycloalkyl refers to a carbocyclic ring in which the fused-ring group is completely saturated, and its example includes but is not limited to bicyclo[3.1.0]hexyl, bicyclo[4.1.0]heptyl, bicyclo[2.2.0]hexyl, bicyclo[3.2.0]heptyl, bicyclo[3.3.0]octyl, bicyclo[4.2.0]octyl, bicyclo[4.3.0]nonyl, octahydropentalenyl, octahydro-1H-indenyl, decahydronaphthalenyl, tetradecahydrophenanthrenyl, 4-azabicyclo[5.3.0]decyl and the like. 6-14 membered partially saturated fused-ring cycloalkyl refers to a carbocyclic ring in which at least one ring is partially saturated, and its example includes but is not limited to bicyclo[3.1.0]hex-2-enyl, bicyclo[4.1.0]hept-3-enyl, bicyclo[3.2.0]hept-3-enyl, bicyclo[4.2.0]oct-3-enyl, 1,2,3,3a-tetrahydropentalenyl, 2,3,3a,4,7,7a-hexahydro-1H-indenyl, 1,2,3,4,4a,5,6,8a-octahydronaphthyl, 1,2,4a,5,6,8a-hexahydronaphthyl, 1,2,3,4,5,6,7,8,9,10-decahydrophenanthryl, bicyclo[4.3.0]non-5-enyl and the like.

As used herein, "bridged-ring group" refers to a cyclic group having 5-12 carbon atoms formed by two rings sharing two non-adjacent atoms with each other. The 5-12 membered bridged-ring group includes 5-12 membered saturated bridged-ring group and 5-12 membered partially saturated bridged-ring group. 5-12 membered saturated bridged-ring group, preferably 6-10 membered saturated bridged-ring group, includes but is not limited to bicyclo[2.1.1]hexyl, bicyclo[2.2.1]heptyl, bicyclo[2.2.2]octyl, bicyclo[3.2.1]octyl, bicyclo[3.3.1]nonyl and the like. 7-12 membered partially saturated bridged-ring group refers to a cyclic group in which at least one ring is not saturated. 6-10 membered partially saturated bridged-ring group is preferable. Its specific example includes but is not limited to bicyclo[2.2.1]hept-5-enyl, bicyclo[3.2.1]oct-6-enyl, bicyclo[2.2.1]heptadienyl and the like.

As used herein, "spiro-ring group" refers to a 5-12 membered polycyclic group formed by at least two rings sharing the same atom with each other. 5-12 membered saturated spiro-ring group refers to a cyclic group in which all rings are saturated, and its specific example includes but is not limited to a group formed from the cyclic structure such as

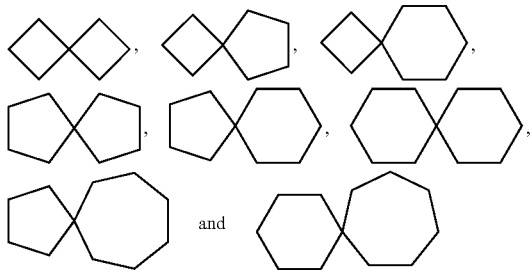

by replacing any replaceable hydrogen atom. 5-12 membered partially saturated spiro-ring group refers to a cyclic group in which at least one ring in the spiro-ring group is unsaturated, and its specific example includes but is not limited to a group formed from the cyclic structure such as

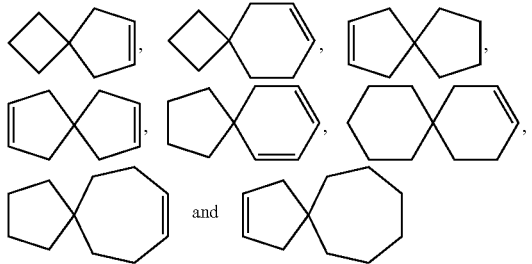

by replacing any replaceable hydrogen atom. 7-10 membered spiro-ring group is preferable. "7-10 membered saturated spiro-ring group" and "7-10 membered unsaturated spiro-ring group" are included.

As used herein, "$C_{3-8}$ cycloalkyloxy" refers to a group in which the $C_{3-8}$cycloalkyl is attached to another structure via an oxygen atom, e.g. cyclopropyloxy, cyclobutyloxy, 1-methylcyclobutyloxy, cyclopentyloxy, cyclohexyloxy, cycloheptyloxy, cyclooctyloxy and the like.

As used herein, "aryl" refers to 6-14 membered cyclic aromatic group, including 6-8 membered monocyclic aryl and 8-14 membered polycyclic aryl. 6-8 membered monocyclic aryl refers to an aryl in which the ring is completely unsaturated, e.g. phenyl, cycloocta-tetraenyl and the like. 8-14 membered polycyclic aryl refers to a cyclic group, which is formed by two or more cyclic structures sharing two adjacent carbon atoms with each other, and in which at least one ring is a completely unsaturated aromatic ring, including 8-14 membered completely unsaturated polycyclic aryl, e.g. naphthyl, anthracenyl, phenanthrenyl and the like, also including 8-14 membered partially saturated polycyclic aryl, e.g. benzene-fused 3-8 membered saturated monocyclic cycloalkyl, benzene-fused 3-8 membered partially saturated monocyclic cycloalkyl. Its specific example is for example 2,3-dihydro-1H-indenyl, 1H-indenyl, 1,2,3,4-tetrahydronaphthyl, 1,4-dihydronaphthyl and the like.

As used herein, "heteroaryl" includes one or more heteroatoms as its ring atom besides the carbon atom(s). Said "heteroatom" includes but is not limited to O, N and S. The heteroaryl can be bonded via the carbon atom or the heteroatom. It includes a monocyclic heteroaryl having 1-4 heteroatoms selected from N, S and O and a saturated or unsaturated polycyclic heteroaryl having 1-4 heteroatoms selected from N, S and O. The monocyclic heteroaryl includes but is not limited to pyrrolyl, imidazolyl, pyrazolyl, 1,2,3-triazolyl, 1,2,4-triazolyl, pyridyl, furyl, thienyl, oxazolyl, isoxazolyl, thiazolyl, isothiazolyl, 1,2,3-thiadiazolyl, 1,2,4-thiadiazolyl, 1,3,4-thiadiazolyl, 1,2,3-oxadiazolyl, 1,2,4-oxadiazolyl, 1,2,5-oxadiazolyl, 1,2,3-triazinyl, 1,2,4-triazinyl, tetrazolyl, oxatriazolyl, 2H-1,2-oxazinyl, 4H-1,2-oxazinyl, 6H-1,2-oxazinyl, 2H-1,3-oxazinyl, 4H-1,3-oxazinyl, 6H-1,3-oxazinyl, 2H-1,4-oxazinyl, 4H-1,4-oxazinyl, isoxazinyl, pyridazinyl, pyrimidinyl, pyrazinyl and the like; the polycyclic heteroaryl includes but is not limited to benzofuryl, isobenzofuryl, benzothienyl, indolyl, isoindolyl, quinolinyl, isoquinolinyl, indolizinyl, indazolyl, phthalazinyl, quinoxalinyl, quinazolinyl, benzodiazinyl, benzisoxazolyl, benzoxazinyl, benzimidazolyl, pyridopyridyl, pyrazolo[3,4-b]pyridyl, purinyl, acridinyl, xanthenyl and the like. The term "5-7 membered heteroaryl" refers to the specific examples having a ring atom number of 5-7 in the above "heteroaryl".

As used herein, "heterocyclyl" refers to a 3-14 membered cyclic group having at least one heteroatom. The "heteroatom" refers to N, O, S and the like. It includes 3-8 membered monocyclic heterocyclyl and 6-14 membered polycyclic heterocyclyl, which are saturated, partially saturated, unsaturated and contain 1-4 heteroatoms selected from N, S, O and/or $SO_2$. It also includes the above heteroaryl and its dihydro- and tetrahydro-analogues. It further includes the fused-ring, the spiro-ring and the bridged-ring, which are saturated, partially saturated, unsaturated and contain 1-4 heteroatoms selected from N, S, O and/or $SO_2$. 5-10 membered heterocyclyl is preferable, and 5-7 membered heterocyclyl is more preferable.

The monocyclic heterocyclyl refers to a monocyclic heterocyclyl containing 3-8 ring atoms (containing at least one heteroatom), including 3-8 membered unsaturated monocyclic heterocyclyl, 3-8 membered partially saturated monocyclic heterocyclyl, and 3-8 membered saturated monocyclic heterocyclyl, preferably 5-7 membered unsaturated monocyclic heterocyclyl, 5-7 membered partially saturated monocyclic heterocyclyl, and 5-7 membered saturated monocyclic heterocyclyl. The 3-8 membered unsaturated monocyclic heterocyclyl refers to an aromatic cyclic group containing at least one heteroatom, and its specific example includes but is not limited to furyl, thienyl, pyrrolyl, thiazolyl, thiodiazolyl, oxazolyl, oxdiazolyl, imidazolyl, pyrazolyl, pyridinyl, pyrimidinyl, 1,4-dioxinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,2,4,5-tetrazinyl, oxepinyl, thiepinyl, azepinyl, 1,3-diazepinyl, azocinyl and the like. The 3-8 membered partially saturated monocyclic heterocyclyl refers to a cyclic group containing a double bond and at least one heteroatom, and its specific example includes but is not limited to 2,5-dihydrothienyl, 4,5-dihydropyrazolyl, 3,4-dihydro-2H-pyranyl, 5,6-dihydro-4H-1,3-oxazinyl and the like. The 3-8 membered saturated monocyclic heterocyclyl refers to a cyclic group containing at least one heteroatom and in which all of bonds are saturated, and its specific example includes but is not limited to aziridinyl, azetidinyl, thietanyl, tetrahydrofuryl, tetrahydropyrrolyl, imidazolidinyl, pyrazolidinyl, tetrahydrofuryl, 1,4-dioxanyl, 1,3-dioxanyl, 1,3-dithianyl, morpholinyl, piperazinyl and the like.

The fused-ring, spiro-ring or bridged-ring containing 1-4 heteroatoms selected from N, S, O and/or $SO_2$ refers to a fused-heterocyclic ring, spiro-heterocyclic ring or bridged-heterocyclic ring formed by replacing one non-shared carbon atom in the fused-ring, spiro-ring or bridged-ring with a heteroatom selected from N, S, O and/or $SO_2$.

The fused heterocyclyl refers to a fused-ring structure, which contains 6-14 ring atoms (contains at least one heteroatom) and is formed by two or more cyclic structures sharing two adjacent atoms with each other, and including 6-14 membered unsaturated fused heterocyclyl, 6-14 membered partially saturated fused heterocyclyl, 6-10 membered saturated fused heterocyclyl. The 6-14 membered unsaturated fused heterocyclyl refers to a fused-ring structure, in which all of the rings are unsaturated, e.g. a structure formed by fusing benzene with 3-8 membered unsaturated monocyclic heterocyclyl, a structure formed by fusing 3-8 membered unsaturated monocyclic heterocyclyl with 3-8 membered unsaturated monocyclic heterocyclyl and the like, and its specific example includes but is not limited to benzofuranyl, isobenzofuranyl, benzothienyl, indolyl, benzoxazolyl, benzoimidazolyl, indazolyl, benzotriazolyl, quinolinyl, isoquinolinyl, acridinyl, phenanthridinyl, benzopyridazinyl, phthalazinyl, quinazolinyl, quinoxalinyl, phenazinyl, pteridinyl, purinyl, naphthyridinyl, and a group formed from the cyclic structure such as

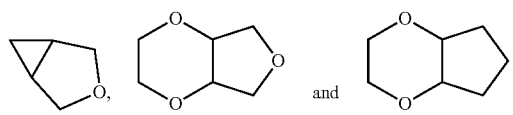

by replacing any replaceable hydrogen atom. The 6-14 membered partially saturated fused heterocyclyl refers to a fused-ring structure containing at least one partially saturated ring, e.g. a structure formed by fusing benzene with 3-8 membered partially saturated monocyclic heterocyclyl, a structure formed by fusing 3-8 membered partially saturated monocyclic heterocyclyl with 3-8 membered partially saturated monocyclic heterocyclyl and the like, and its specific example includes but is not limited to 1,3-dihydrobenzofuryl, benzo[d][1.3]dioxacyclopentenyl, isoindolinyl, chromanyl, and a group formed from the cyclic structure such as 1,2,3,4-tetrapyrrolo[3,4-c]pyrrole,

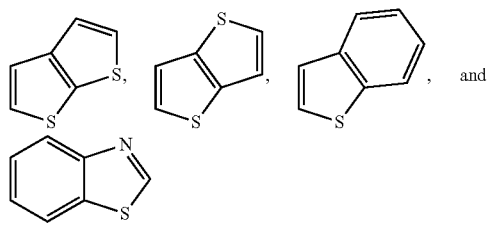

by replacing any replaceable hydrogen atom. The 6-10 membered saturated fused heterocyclyl refers to a fused-ring structure, in which all of the rings are saturated, e.g. a structure formed by fusing 3-8 membered saturated monocyclic heterocyclyl with 3-8 membered saturated monocyclic heterocyclyl, and its specific example includes but is not limited to cyclobutane-fused tetrahydropyrrolyl, cyclopentane-fused tetrahydropyrrolyl, azetidine-fused imidazolidinyl, and a group formed from the cyclic structure such as

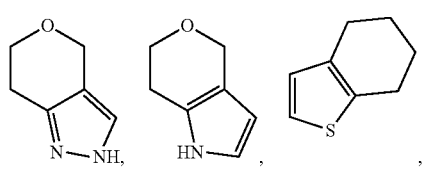

by replacing any replaceable hydrogen atom.

The bridged-heterocyclyl refers to a bridged-ring structure, which contains 5-12 ring atoms (containing at least one heteroatom) and is formed by two or more cyclic structures sharing two non-adjacent atoms with each other. The "5-12 membered bridged-heterocyclyl" includes 5-12 membered saturated bridged-heterocyclyl, 5-12 membered partially saturated bridged-heterocyclyl. The 5-12 membered saturated bridged-heterocyclyl refers to a cyclic group, in which all of the rings are saturated, preferably 7-8 membered saturated bridged-heterocyclyl, and its specific example includes but is not limited to a group formed from the cyclic structure such as

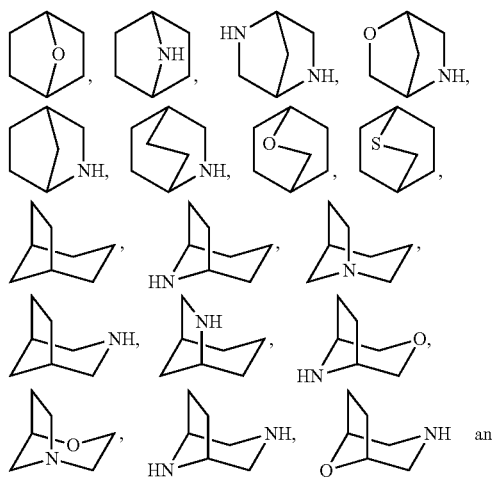

by replacing any replaceable hydrogen atom.

The 5-12 membered partially saturated bridged-heterocyclyl refers to a cyclic group, in which at least one ring is unsaturated, preferably 7-8 membered partially saturated bridged-heterocyclyl, and its specific example includes but is not limited to a group formed from the cyclic structure such as

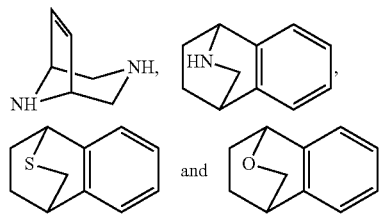

by replacing any replaceable hydrogen atom.

The spiro-heterocyclyl refers to a Spiro-ring structure which contains 5-12 ring atoms (contains at least one heteroatom) and is formed by two or more cyclic structures sharing the same atom with each other. The 5-12 membered spiro-heterocyclyl includes 5-12 membered saturated spiro-heterocyclyl and 5-12 membered partially saturated spiro-heterocyclyl.

The 5-12 membered saturated spiro-heterocyclyl refers to a cyclic group in which all of the rings are saturated, and its specific example includes but is not limited to a group formed from the cyclic structure such as

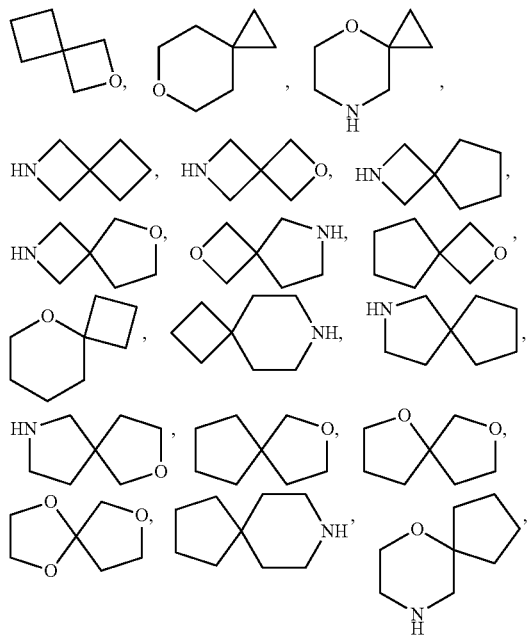

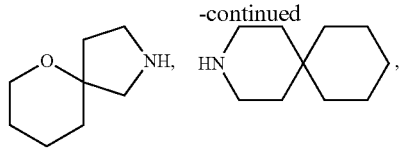

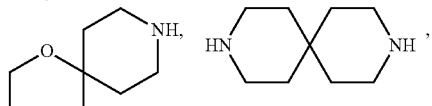

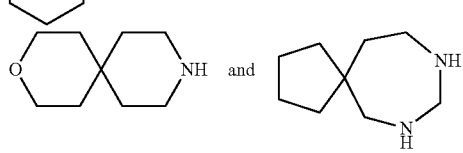

by replacing any replaceable hydrogen atom.

The 5-12 membered partially saturated spiro-heterocyclyl refers to a cyclic group, in which at least one ring is unsaturated, and its specific example includes but is not limited to a group formed from the cyclic structure such as

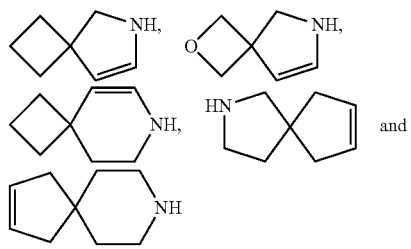

by replacing any replaceable hydrogen atom.

The term "3-12 membered heterocyclyl" refers to the specific examples having a ring atom number of 3-12 in the above "heterocyclyl". The term "5-12 membered heterocyclyl" refers to the specific examples having a ring atom number of 5-12 in the above "heterocyclyl". The term "5-7 membered heterocyclyl" refers to the specific examples having a ring atom number of 5-7 in the above "heterocyclyl".

As used herein, "one or more" (when expressing the number), includes but is not limited to 1-4, 1-3, 1-2 and the like.

As used herein, "1-3" (when expressing the number) refers to 1, 2 or 3.

As used herein, "3-8 membered" refers to 3, 4, 5, 6, 7, 8 membered, preferably 5-8 membered, further preferably 5-7 membered, more further preferably 5-6 membered. The "5-8 membered" refers to 5, 6, 7, 8 membered, the "5-7 membered" refers to 5, 6, 7 membered.

As used herein, "7-12 membered spiro-ring" refers to a polycyclic structure containing 7-12 carbon atoms and at least formed by two rings sharing the same atom. 7-10 membered spiro-ring group is further preferable.

As used herein, "7-12 membered spiro-ring group" refers to a cyclic group in which all of the rings are saturated, preferably 7-10 membered spiro-ring group, and its specific example includes but is not limited to a group formed from the cyclic structure such as

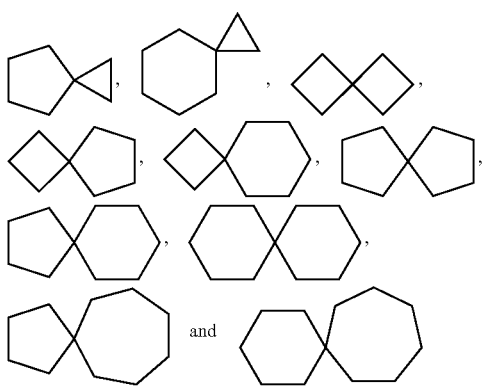

by replacing any replaceable hydrogen atom.

As used herein, "7-10 membered spiro-ring group containing 1-2 heteroatoms selected from N, O, S, SO and/or $SO_2$," refers to a 7-10 membered spiro-heterocyclyl formed by replacing 1 or 2 carbon atoms in the above spiro-ring group with 1 or 2 heteroatoms selected from N, O, S, SO and/or $SO_2$, and its specific examples includes but is not limited to a group formed from the cyclic structure such as

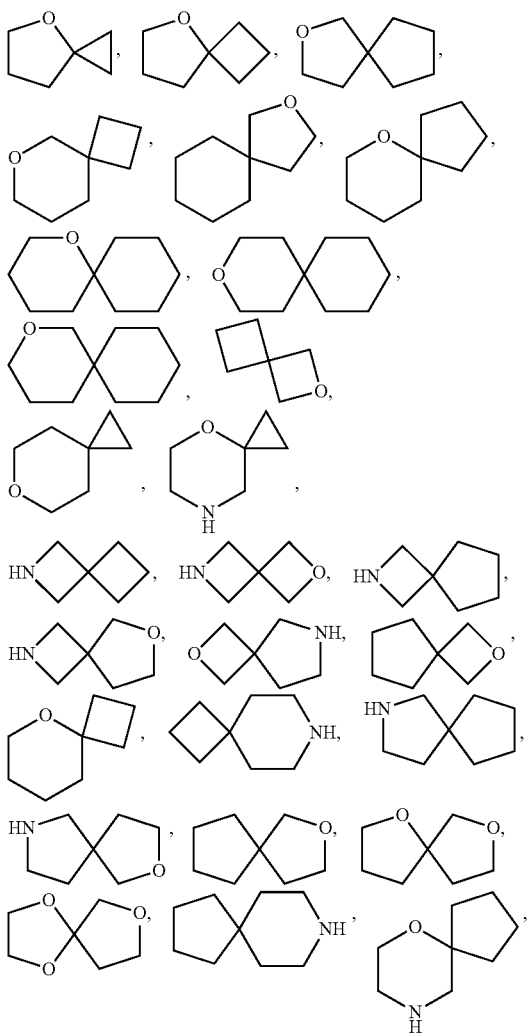

by replacing any replaceable hydrogen atom.

The term "7-10 membered spiro-ring" refers to the specific examples having a ring atom number of 7-10 in the above "5-12 membered spiro-ring".

The present invention further involves a process for preparing the compound represented by general formula (I).

The process for preparing the compound represented by general formula (I) comprises a compound represented by general formula (IV), a pharmaceutically acceptable salt thereof, an easily hydrolyzable ester thereof or a stereoisomer thereof, and a compound represented by general formula (V), a pharmaceutically acceptable salt thereof, an easily hydrolyzable ester thereof or a stereoisomer thereof are subjected to a nucleophilic reaction,

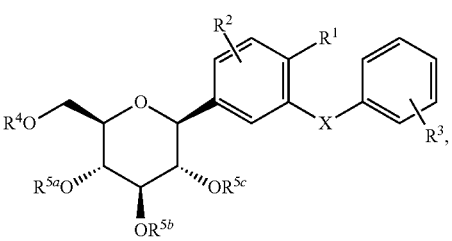
(I)

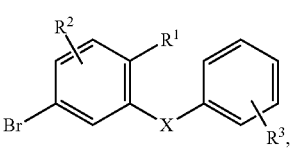
(IV)

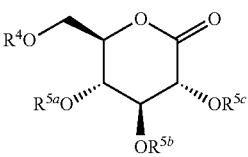
(V)

wherein, $R^1$, $R^2$, $R^3$, $R^4$, $R^{5a}$, $R^{5b}$ and $R^{5c}$ and X are defined as above.

The above compounds of the present invention can be synthesized according to the method illustrated in the following scheme and/or other technology known to a person skilled in the art, including but not limited to the following method.

When X is methylene, the reaction scheme is as follows:

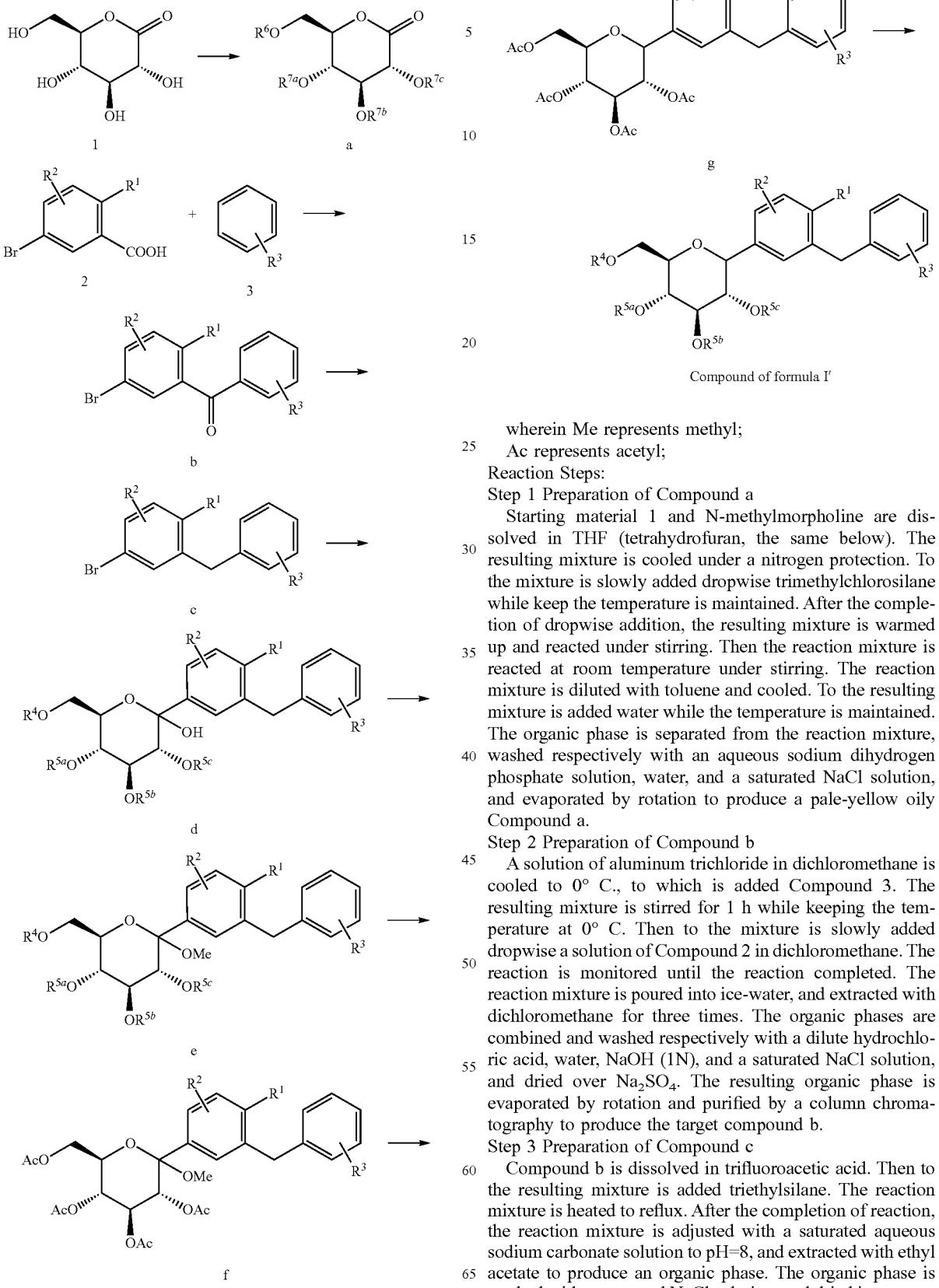

Compound of formula I' wherein Me represents methyl;
Ac represents acetyl;
Reaction Steps:
Step 1 Preparation of Compound a Starting material 1 and N-methylmorpholine are dissolved in THF (tetrahydrofuran, the same below). The resulting mixture is cooled under a nitrogen protection. To the mixture is slowly added dropwise trimethylchlorosilane while keep the temperature is maintained. After the completion of dropwise addition, the resulting mixture is warmed up and reacted under stirring. Then the reaction mixture is reacted at room temperature under stirring. The reaction mixture is diluted with toluene and cooled. To the resulting mixture is added water while the temperature is maintained. The organic phase is separated from the reaction mixture, washed respectively with an aqueous sodium dihydrogen phosphate solution, water, and a saturated NaCl solution, and evaporated by rotation to produce a pale-yellow oily Compound a.

Step 2 Preparation of Compound b

A solution of aluminum trichloride in dichloromethane is cooled to 0° C., to which is added Compound 3. The resulting mixture is stirred for 1 h while keeping the temperature at 0° C. Then to the mixture is slowly added dropwise a solution of Compound 2 in dichloromethane. The reaction is monitored until the reaction completed. The reaction mixture is poured into ice-water, and extracted with dichloromethane for three times. The organic phases are combined and washed respectively with a dilute hydrochloric acid, water, NaOH (1N), and a saturated NaCl solution, and dried over $Na_2SO_4$. The resulting organic phase is evaporated by rotation and purified by a column chromatography to produce the target compound b.

Step 3 Preparation of Compound c

Compound b is dissolved in trifluoroacetic acid. Then to the resulting mixture is added triethylsilane. The reaction mixture is heated to reflux. After the completion of reaction, the reaction mixture is adjusted with a saturated aqueous sodium carbonate solution to pH=8, and extracted with ethyl acetate to produce an organic phase. The organic phase is washed with a saturated NaCl solution, and dried in vacuum to produce a crude Compound c.

Step 4 Preparation of Compound d

Compound c is dissolved in anhydrous THF. The resulting mixture is cooled to −78° C. under a nitrogen protection. To the mixture is added dropwise n-BuLi (n-butyl lithium, the same below), and then added dropwise a solution of Compound c in n-hexane. The mixture is reacted under stirring. Then the reaction mixture is quenched with an aqueous saturated ammonium chloride solution. The aqueous layer is extracted with ethyl acetate. The combined organic phase is washed with water and a saturated NaCl solution, and evaporated by rotation to produce an oily Compound d.

Step 5 Preparation of Compound e

Compound d is dissolved in absolute anhydrous methanol. To the resulting mixture is added a solution of methanesulfonic acid in anhydrous methanol under cooling. The resulting mixture is slowly warmed up to room temperature and stirred. After the completion of reaction, the mixture is adjusted with a saturated NaHCO₃ solution, and extracted with ethyl acetate. The combined organic phase was washed with water and a saturated NaCl solution, dried, and evaporated by rotation to produce Compound e.

Step 6 Preparation of Compound f

Compound e, diisopropylethylamine and DMAP (4-dimethylaminopyridine, the same below) are dissolved in THF. The resulting mixture is cooled to 0° C. To the mixture is slowly added acetic anhydride under stirring. The reaction mixture is adjusted with a saturated aqueous sodium bicarbonate solution, and extracted with ethyl acetate. The combined organic phase was washed with water and a saturated NaCl solution, dried, concentrated by rotary evaporation, and purified by a column chromatography to produce Compound f.

Step 7 Preparation of Compound g

To a solution of Compound f in acetonitrile under cooling are added triethylsilane and boron trifluoride-diethyl etherate. The reaction is monitored until the reaction completed. The reaction mixture is quenched with a saturated sodium bicarbonate solution, and extracted with ethyl acetate. The combined organic phase was washed with water and a saturated NaCl solution, dried, concentrated by rotary evaporation, recrystallized (n-hexane and ethyl acetate) to produce Compound g.

Step 8 Preparation of Compound of Formula (I')

Compound g is added to a mixed solution of tetrahydrofuran and methanol. To the resulting mixture is added an aqueous lithium hydroxide monohydrate solution at 0° C. The reaction mixture is slowly warmed up to room temperature under stirring. The reaction was monitored until the reaction completed. The reaction mixture was concentrated, and extracted with dichloromethane. The combined organic phase was washed with water and a saturated NaCl solution, dried, and concentrated to produce Compound of formula (I').

In the above reaction scheme, $R^1$, $R^2$, $R^3$, $R^4$, $R^{5a}$, $R^{5b}$ and $R^{5c}$ are defined as hereinbefore.

For convenience, the well known abbreviations are used to stand for the corresponding chemical compounds, and include but are not limited to:

THF: tetrahydrofuran;
DMAP: 4-dimethylaminopyridine;
DIPEA: N,N-diisopropylethylamine;
n-BuLi: n-butyl lithium;
TMS: trimethylsilane.

The present invention further involves the Intermediates used in the process for preparing the compound represented by general formula (I), i.e. the compounds represented by general formulae (II), (III), and (IV), a pharmaceutically acceptable salt thereof, an easily hydrolyzable ester thereof or a stereoisomer thereof, wherein, $R^1$, $R^2$, $R^3$, $R^4$, $R^{5a}$, $R^{5b}$ and $R^{5c}$ and X are defined as hereinbefore.

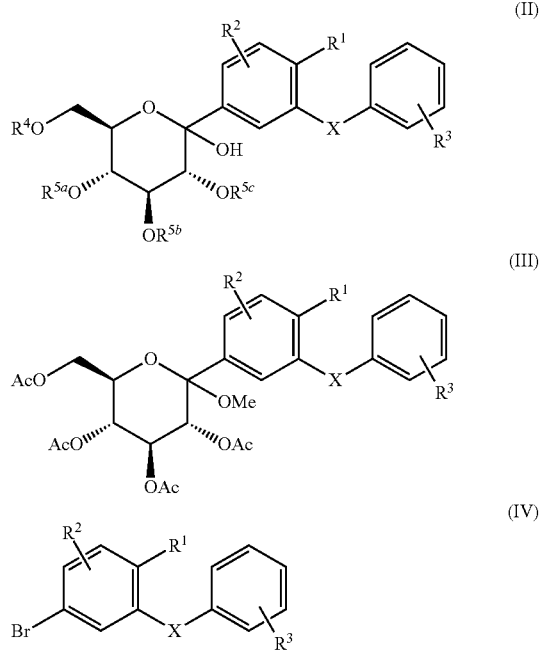

The pharmaceutically acceptable salt of any above compound of the present invention comprises alkali metal salts, such as Na salt, K salt, Li salt and the like; alkaline-earth metal salts, such as Ca salt, Mg salt and the like; other metal salts, such as Al salt, Fe salt, Zn salt, Cu salt, Ni salt, Co salt and the like; inorganic base salts, such as ammonium salt; organic base salts, such as tert-octylamine salt, dibenzylamine salt, morpholine salt, glucosamine salt, alkyl phenylglycinate salt, ethylene diamine salt, N-methylglucosamine salt, guanidine salt, diethylamine salt, triethylamine salt, dicyclohexyl amine salt, N,N'-dibenzylethylene diamine salt, chloroprocaine salt, procaine salt, diethanol amine salt, N-benzyl-phenylethyl amine salt, piperazine salt, tetramethyl amine salt, tris(hydroxymethyl)aminomethane salt and the like; halogen acid salt, such as hydrofluoric acid salt, hydrochloride, hydrobromide, hydriodate and the like; inorganic acid salts, such as nitrate, perchlorate, sulfate, phosphate and the like; lower alkanesulfonate, such as mesylate, trifluoromesylate, ethanesulfonate and the like; arylsulfonate, such as benzenesulfonate, para-benzenesulfonate and the like; organic acid salts, such as acetate, malate, fumarate, succinate, citrate, tartrate, oxalate, maleate and the like; amino acid salts, such as glycine salt, trimethyl glycine salt, arginine salt, ornithine salt, glutamate salt, asprtate salt and the like.

The "easily hydrolysable ester" of any above compound of the present invention refers to a pharmaceutically acceptable ester that can be hydrolyzed in the human body to produce the parent compound. It is obvious for a person skilled in the art that, the easily hydrolysable ester of the present compound can be formed at the free carboxyl or hydroxyl of the compound and can be prepared according to the conventional method.

The "stereoisomer" of any above compound of the present invention includes all of epimers, diastereoisomers and tautomers. A bond expressed in a wedge shape indicates that the bond extends out of the paper surface, while a bond expressed in a hatched line indicates that the bond returns into the paper surface.

The present invention also involves a stereoisomer of the compound represented by general formula (I). The present compound contains one or more asymmetric centers, and therefore can be present as a racemate or a recemic mixture, a single enantiomer, a mixture of diastereoisomers and a single diastereoisomer. The present compound has an asymmetric center, which will each independently produce two optical isomers. Any mixture of all possible optical isomers and diastereoisomers as well as the pure compound or the partially pure compound are well in the scope of the present invention. The present invention involves all stereoisomers of these compounds.

The present compound of general formula (I) has two or more chiral centers. The substance resulting from the synthesis is a racemate. The desired enantiomeric pure compound can be obtained by a chiral resolution, e.g. a chromatography having a chiral stationary phase (such as a high-pressure preparative liquid phase and a supercritical fluid chromatography). The chiral filler includes but is not limited to Chiralcel OJ-H, Chiralpak AD-H, Chiralpak IA, and Chiralpak AS-H.

The present invention further involves a pharmaceutical composition containing any above compound, a pharmaceutically acceptable salt thereof, an easily hydrolyzable ester thereof or a stereoisomer thereof and other pharmaceutically acceptable active ingredients.

The present invention further involves a clinically or pharmaceutically acceptable dosage form, which comprises any above compound, a pharmaceutically acceptable salt thereof, an easily hydrolyzable ester thereof or a stereoisomer thereof, can be formulated by a conventional means well known in the art, and can be administered orally, parenterally, rectally or pulmonarily to a patient in need thereof. For the oral administration, it can be prepared into a conventional solid formulation, such as tablet, capsule, pill, granule and the like; or into an oral liquid formulation, such as oral solution, oral suspension, syrup and the like. Upon preparing into an oral formulation, suitable filler, binder, disintegrant, lubricant and the like can be added. For the parenteral administration, it can be prepared into an injectable preparation, including an injection solution, a sterile injection powder and a concentrated injection solution. For preparing the injectable preparation, an additive can be optionally added, depending on the nature of drug. For the rectal administration, it can be prepared into a suppository and the like. For the pulmonary administration, it can be prepared into an inhalant, a spraying agent and the like. Per unit of the formulation contains a physiologically effective amount, for example 0.01 g-10 g, such as 0.01 g, 0.05 g, 0.1 g, 0.125 g, 0.2 g, 0.25 g, 0.3 g, 0.4 g, 0.5 g, 0.6 g, 0.75 g, 1 g, 1.25 g, 1.5 g, 1.75 g, 2 g, 2.5 g, 3 g, 4 g, 5 g, 10 g and the like of the compound represented by general formula (I).

The present invention also involves the use of the present compound in manufacture of a medicament for treating and/or preventing the diabetes mellitus. The C-glycoside derivative of the present invention can be useful in treating various diabetes-associated diseases such as the insulin resistance disease and the obesity, besides the diabetes mellitus such as insulin-dependent diabetes mellitus (Type I diabetes mellitus), noninsulin-dependent diabetes mellitus (Type II diabetes mellitus) and the like; as well as in preventing these diseases.

The present compound has the following characteristics:
(1) The present compound has remarkable effects on inhibiting the sodium glucose co-transporter 2 (SGLT-2) and reducing the blood glucose, and can be safely used to treat and/or prevent the diabetes mellitus and the various diabetes-associated diseases in the mammals (including human).
(2) The present compound has a good physical-chemical property, a low toxicity and a low side-effect.
(3) The present compound can be produced by a simple preparation process, which has a high purity and a good stability, and therefore is apt to be scaled up industrially.

Hereinafter, the beneficial effects of the present compounds will be illustrated by in vitro/in vivo assays for the pharmacological activities. However, it should be noted that the beneficial effects of the present compounds are not limited to the effects as illustrated below.

Assay: In Vitro/In Vivo Assays for the Pharmacological Activities of the Present Compounds 1. In Vitro Evaluation Assay In the in vitro evaluation method according to the present invention, the human SGLT2 and SGLT1 sequences were transfected to Chinese hamster ovary cells to express stably. By measuring inhibition of the sodium dependent adsorption of [$^{14}$C]-labeled R-methyl-D-glucopyranoside (AMG) into the cells, the half-inhibition concentration $IC_{50}$ was determined. Assay samples: The present compounds, lab-made, their chemical names and structural formulae are described hereinbefore.

Buffer A (KRH-Na+): 120 mM NaCl, 4.7 mM KCl, 1.2 mM $MgCl_2$, 2.2 mM $CaCl_2$, 10 mM HEPES (PH 7.4 with 1 mM Tris).

Buffer A–(KRH-NMG): 120 mM NMG, 4.7 mM KCl, 1.2 mM $MgCl_2$, 2.2 mM $CaCl_2$, 10 mM HEPES (PH 7.4 with 1 mM Tris).

Buffer D: 120 mM NaCl, 4.7 mM KCl, 1.2 mM $MgCl_2$, 2.2 mM $CaCl_2$, 10 mM HEPES, 0.5 mM phlorizin (PH 7.4 with 1 mM Tris).

Assay method: Human SGLT2 and SGLT1 sequences were stably expressed in the CHO cells. The cell culture was conducted in a 96-well plate for 12 hr. The plate was washed with KRH-Na+(Buffer A) or KRH-NMG (Buffer A–) buffering solution for three times, 200 μL/well. Then the plate was washed with a buffering solution containing Buffer A or Buffer A– plus [$^{14}$C]-AMG (10 μCi/mL), 100 μL/well. The cell culture was conducted at 37° C. for 1 h. Then, 100 μL, of ice pre-cooled buffering solution (Buffer D) was added to terminate the assay. The plate was washed for 5 times. Then 100 mM NaOH solution was added, 20 μL/well, and the centrifugation at 600 rpm was conducted for 5 mins. Then Microscint 40 solution was added, 80 μl/well, and the centrifugation at 600 rpm was conducted for 5 mins. Finally, the radioactivity of [$^{14}$C]-AMG was detected with Micro-Beta Trilux (purchased from PerkinElmer Co. Ltd.) according to the scintillation counting method, and the half-inhibition concentration $IC_{50}$ was calculated.

The above assays were entrusted to Shanghai ChemPartner Co. Ltd.

Assay Results and Conclusions:

TABLE 1

The inhibition effects of the present compounds
The evaluation results for the inhibition effects of the present compounds are as follows:

| Nos. | SGLT1 $IC_{50}$(nm) | SGLT2 $IC_{50}$(nm) | Selectivity |
| --- | --- | --- | --- |
| Compound 4 | 2397.7 | 3.63 | 660 |
| Compound 10 | 1885.3 | 3.16 | 596 |
| Compound 13 | 29085.9 | 3.99 | 73 |

It can be seen from the above table that the present compounds have a good inhibition effect on SGLT2 as well as a good selectivity.

2. In Vivo Evaluation Assay
Rat In Vivo Pharmacokinetic Assay for the Present Compounds Assay animals: 6-8 weeks aged male SD rats (purchased from Vital River Laboratories), 6 rats per compound, weighing 220-250 g.

Assay Samples:

The present compounds, lab-made, their chemical names and structural formulae are described hereinbefore.

BI-10773, lab-made, its structural formula is shown below:

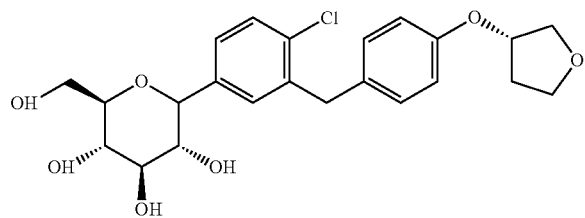 [SMILES: OC[C@H]1OC(c2ccc(Cl)c(Cc3ccc(O[C@H]4CCOC4)cc3)c2)[C@H](O)[C@@H](O)[C@@H]1O]

Dissolved in an appropriate solvent (5% DMSO+95% (6% HP-β-CD solution)).
Assay Method:
Administration: See Table 2

TABLE 2

Administration of compounds in the rat PK (pharmacokinetic) assay

| Animal amount | Sex | Route | Dosage (mg/kg) | Volume (ml/kg) | Concentration (mg/mL) |
|---|---|---|---|---|---|
| 3 | Male | IV | 2 | 2 | 1 |
| 3 |  | PO | 5 | 5 | 1 |

Blood collection: each of about 100 μL, whole blood were collected at 0 h, 0.083 h, 0.25 h, 0.5 h, 1 h, 2 h, 4 h, 6 h, 8 h and 24 h. The collected blood samples were centrifuged at 4° C. at 8000 rpm in a low temperature high-speed centrifuge (5415R, Eppendorf) for 6 mins to separate the blood plasm. The separated plasm was preserved at −80 CC in a refrigerator.

Plasm Sample Analysis:

20 μL of the plasm was carefully taken out, to which was added 200 μL acetonitrile solution (containing internal standard KBP-1204 50 ng/ml). The plasm was subjected to a vortex at 1500 rpm for 3 mins, and then centrifuged at 12000 rpm for 5 mins. The supernatant was taken and was analyzed with LC-MS/MS (API4000, Aplplied Biosystems).

Equation Absolute bioavailability $F\% = [AUC]INF(PO)*Dose(IV)/[AUC]INF(IV)*Dose(PO)$

TABLE 3

Rat PK (pharmacokinetic) evaluation results (IV) for the compounds

| PK parameters (units) | Compound 4 | Compound 10 | Compound 13 | BI-10773 |
|---|---|---|---|---|
| T½ (h) | 6.81 ± 0.74 | 0.88 ± 0.21 | 3.75 ± 0.60 | 0.70 ± 0.07 |
| $AUC_{last}$ (h * ng/ml) | 12398.14 ± 731.98 | 971.80 ± 163.58 | 6949.75 ± 100.09 | 1093.35 ± 137.68 |
| $AUC_{inf}$ (h * ng/ml) | 13516.25 ± 451.24 | 983.81 ± 166.90 | 7010.28 ± 148.14 | 1104.73 ± 141.71 |

TABLE 4

Rat PK (pharmacokinetic) evaluation results (PO) for the compounds

| PK parameters (units) | Compound 4 | Compound 10 | Compound 13 | BI-10773 |
|---|---|---|---|---|
| T½ (h) | 7.33 ± 0.96 | 1.77 ± 0.47 | 3.36 ± 0.46 | 1.33 ± 0.33 |
| $AUC_{last}$ (h * ng/ml) | 26272.99 ± 1791.10 | 429.52 ± 165.50 | 6223.52 ± 1351.38 | 425.91 ± 116.07 |
| $AUC_{inf}$ (h * ng/ml) | 29472.22 ± 2722.24 | 463.50 ± 160.32 | 6289.32 ± 1363.25 | 456.52 ± 114.26 |
| F % | 87.22 ± 8.06 | 18.85 ± 6.52 | 35.89 ± 7.78 | 16.53 ± 4.14 |

T½ represents the half-life $AUC_{last}$ represents the area under curve on administration from time = 0→t $AUC_{inf}$ represents the area under curve on administration from time = 0→∞

F % represents the absolute bioavailability

Conclusion: it can be seen from the above assay result that Compound 4, after SD rat's intragastric administration, had a relative high absolute bioavailability of 87.22%; while BI-10773, after the intragastric administration, had a relative poor absolute bioavailability of 16.53%.

Urine Glucose Assay in Normal Rats

SPF-grade male Sprague-Dawley rats, 6-weeks aged, were used in this urine glucose assay. After the rats were fasted for 15 h, the rats were divided randomly into a blank control group, a model group, a positive drug group and a test drug group according to their body weights. The rats were put into metabolic cages where water was available but food was unavailable. The urines in this 24 hours were collected. Then, the drugs were orally administered (10 mg/Kg) and then the glucose was fed (5 g/kg) to the animals. Then the animals were put into metabolic cages. The rats were supplemented with food one hour after the drug administration and the glucose feeding, and then could freely contact the diets. The urines in this 24 hours were collected and recorded. The collected urines were centrifuged at 3000 rpm for 15 mins. The residues were removed. The supernatants were taken and the urine glucose contents therein were measured.

The urine glucose contents were standardized based on the body weight of 200 g. The data were expressed in average±standard deviation. The resulting values were analyzed with one-way ANOVA, and the comparisons between groups were conducted with one-way ANOVA and Dunnett test, where $p<0.05$ was considered to have a statistical significance.

TABLE 5

The urine glucose assay result for the compounds:

| No. | Urine volume (ml) | Urine glucose mass (mg/200 g) |
|---|---|---|
| Compound 4 | 18.50 | 1197.79 |
| Compound 10 | 16.25 | 972.99 |
| BI-10773 | 16.63 | 866.67 |

In summary, the present compounds showed a relative good hypoglycemic effect.

EXAMPLES

The following examples are intended to illustrate the invention and are not to be construed as being limitations thereon. All of the technical solutions that can be accomplished based on the above disclosure fall in the scope of the present invention.

In the examples, the used starting materials were commercially available, for example, from Alfa Aesar China (Tianjin) Co., Ltd., Sinopharm Chemical Reagent Co., Ltd., Tianjin Fuyu Fine Chemical Co., Ltd., Shanghai Bangchen Chemical Co. Ltd., Tianjin Guangcheng Chemical Reagent Co., Ltd., Tianjin Guangfu Fine Chemical Co., Ltd., Tianjin Kemiou Chemical Reagent Co., Ltd.

Example 1

Preparation of Intermediates S-1 and S-2

Preparation of (3R,4S,5R,6R)-3,4,5-tris(trimethylsilyloxy)-6-((trimethylsilyloxy)methyl)tetrahydro-2H-pyran-2-one Intermediate S-1

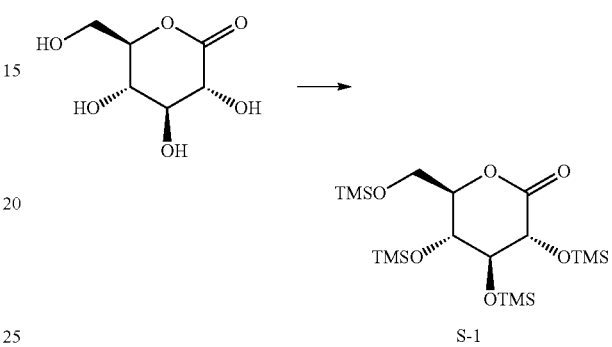

(3R,4S,5S,6R)-3,4,5-trihydroxy-6-(hydroxymethyl)tetrahydro-2H-pyran-2-one (239 g, 1.34 mol) and N-methylmorpholine (1.18 L, 10.73 mol) were dissolved in THF (2.4 L). The mixture was cooled to −5° C. under a nitrogen protection. To the mixture was slowly added dropwise trimethylchlorosilane (1022 mL, 8.05 mol), while the temperature was kept at not higher than 5° C. during the dropwise addition. After the dropwise addition, the mixture was warmed up to 35° C. and stirred for 5 h. Then the mixture was stirred at room temperature for 15 h. The mixture was diluted by addition of toluene, and cooled to 0-5° C. Then to the mixture was added water while the temperature was kept at not higher than 10° C. An organic phase was separated from the reaction mixture, washed with an aqueous sodium dihydrogen phosphate solution, water and a saturated NaCl solution respectively, and evaporated by rotation to produce 593.2 g of a pale-yellow oily (3R,4S,5R,6R)-3,4,5-tris(trimethylsilyloxy)-6-((trimethylsilyloxy)methyl)tetrahydro-2H-pyran-2-one (Intermediate S-1).

The Preparation of 2-chloro-5-bromo-benzoyl chloride

Intermediate S-2

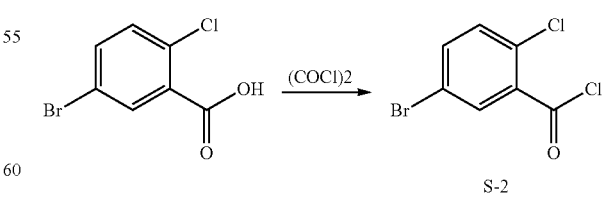

5-bromo-2-chlorobenzoic acid (10 g, 42.64 mmol) was dissolved in 20 mL dichloroethane. To the mixture was added dropwise oxalyl chloride (5 g, 40 mmol) within 30 minutes. After the dropwise addition, the mixture was stirred for 30 minutes. Then the solvent was removed by rotary evaporation as much as possible to produce a crude product of Intermediate S-2, which was directly used in the next reaction without any treatment.

Example 2

Preparation of Compound 1

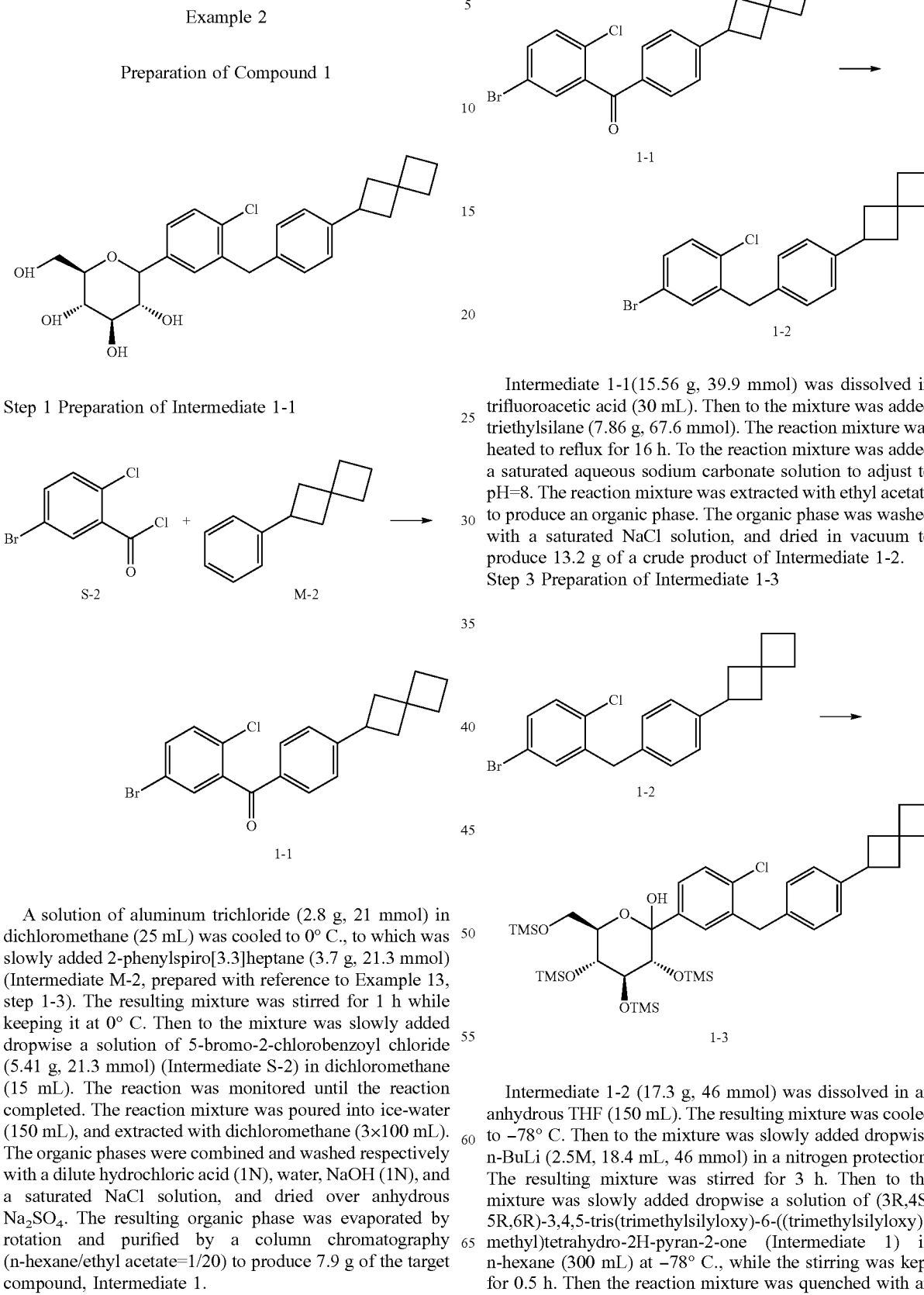

Step 1 Preparation of Intermediate 1-1

A solution of aluminum trichloride (2.8 g, 21 mmol) in dichloromethane (25 mL) was cooled to 0° C., to which was slowly added 2-phenylspiro[3.3]heptane (3.7 g, 21.3 mmol) (Intermediate M-2, prepared with reference to Example 13, step 1-3). The resulting mixture was stirred for 1 h while keeping it at 0° C. Then to the mixture was slowly added dropwise a solution of 5-bromo-2-chlorobenzoyl chloride (5.41 g, 21.3 mmol) (Intermediate S-2) in dichloromethane (15 mL). The reaction was monitored until the reaction completed. The reaction mixture was poured into ice-water (150 mL), and extracted with dichloromethane (3×100 mL). The organic phases were combined and washed respectively with a dilute hydrochloric acid (1N), water, NaOH (1N), and a saturated NaCl solution, and dried over anhydrous Na$_2$SO$_4$. The resulting organic phase was evaporated by rotation and purified by a column chromatography (n-hexane/ethyl acetate=1/20) to produce 7.9 g of the target compound, Intermediate 1.

Step 2 Preparation of Intermediate 1-2

Intermediate 1-1(15.56 g, 39.9 mmol) was dissolved in trifluoroacetic acid (30 mL). Then to the mixture was added triethylsilane (7.86 g, 67.6 mmol). The reaction mixture was heated to reflux for 16 h. To the reaction mixture was added a saturated aqueous sodium carbonate solution to adjust to pH=8. The reaction mixture was extracted with ethyl acetate to produce an organic phase. The organic phase was washed with a saturated NaCl solution, and dried in vacuum to produce 13.2 g of a crude product of Intermediate 1-2.

Step 3 Preparation of Intermediate 1-3

Intermediate 1-2 (17.3 g, 46 mmol) was dissolved in an anhydrous THF (150 mL). The resulting mixture was cooled to −78° C. Then to the mixture was slowly added dropwise n-BuLi (2.5M, 18.4 mL, 46 mmol) in a nitrogen protection. The resulting mixture was stirred for 3 h. Then to the mixture was slowly added dropwise a solution of (3R,4S, 5R,6R)-3,4,5-tris(trimethylsilyloxy)-6-((trimethylsilyloxy) methyl)tetrahydro-2H-pyran-2-one (Intermediate 1) in n-hexane (300 mL) at −78° C., while the stirring was kept for 0.5 h. Then the reaction mixture was quenched with an aqueous saturated ammonium chloride solution (100 mL). The resulting aqueous layer was extracted with ethyl acetate (3×100 mL). The combined organic phase was washed with water and a saturated NaCl solution, and evaporated by rotation to produce 18.79 g of an oily Intermediate 1-3.

Step 4 Preparation of Intermediate 1-4

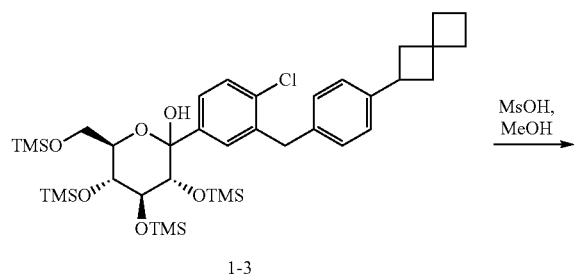

1-3

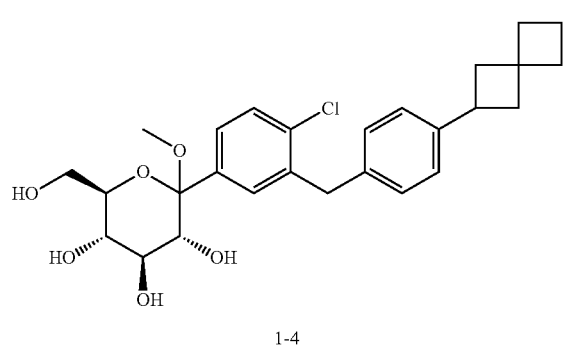

1-4

Intermediate 1-3 (4.75 g, 10 mmol) was dissolved in absolute anhydrous methanol (10 mL). The resulting mixture was cooled to 0° C. To the mixture was added a solution of methanesulfonic acid (MsOH) (0.4 mL) in anhydrous methanol (10 mL). The mixture was slowly warmed up to room temperature and stirred for 16 h. The mixture was adjusted with an aqueous saturated NaHCO₃ solution to adjust to pH=8, and extracted with ethyl acetate. The combined organic phase was washed with water and a saturated NaCl solution, dried, and evaporated by rotation to produce 4.89 g of Intermediate 1-4.

Step 5 Preparation of Intermediate 1-5

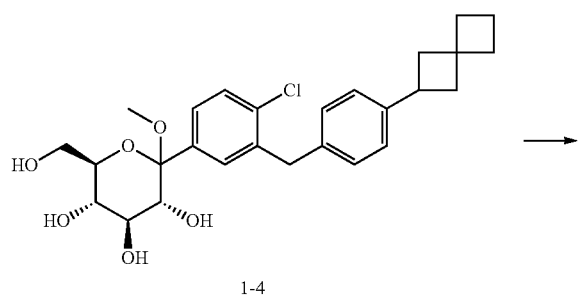

1-4

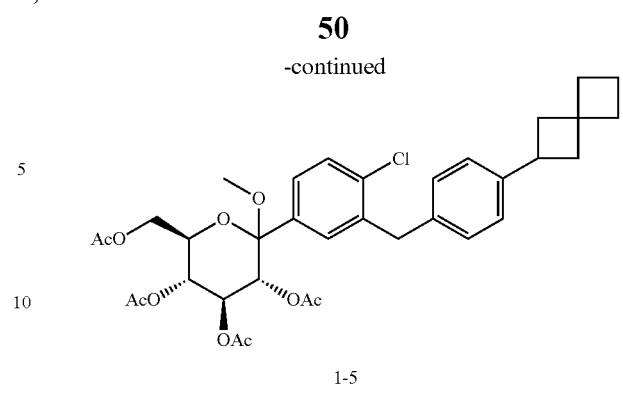

1-5

Intermediate 1-4 (4.45 g, 9.1 mmol), diisopropylethylamine (DIPEA) (9.4 g, 72.8 mmol) and DMAP (10 mg) were dissolved in THF (100 mL). The resulting mixture was cooled to 0° C. To the mixture was slowly added acetic anhydride (Ac₂O) (7.43 g, 72.8 mmol). The resulting mixture was stirred for 0.5 h. The reaction mixture was adjusted with a saturated aqueous sodium bicarbonate solution to pH=8 and extracted with ethyl acetate (3×60 mL). The combined organic phase was washed with water (70 mL) and a saturated NaCl solution (70 mL), dried, concentrated by rotary evaporation, and purified by a column chromatography to produce 5.1 g of Intermediate 1-5.

Step 6 Preparation of Intermediate 1-6

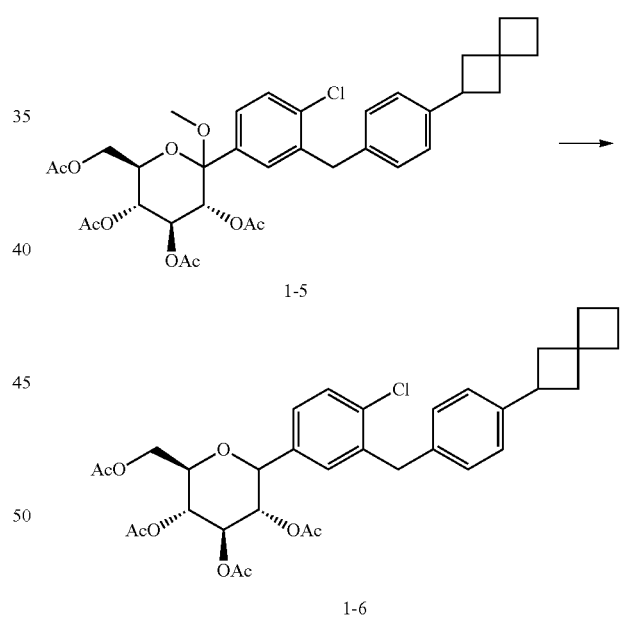

1-5

1-6

A solution of Intermediate 1-5 (10.5 g, 16.0 mmol) in acetonitrile (50 mL) was cooled to 10° C., to which were added triisopropylsilane (5.1 g, 32 mmol) and boron trifluoride-diethyl etherate (6.8 g, 48 mmol). The reaction was monitored until the reaction completed. The reaction mixture was quenched with a saturated sodium bicarbonate solution, and extracted with ethyl acetate (3×100 mL). The combined organic phase was washed with water and a saturated NaCl solution, dried, concentrated by rotary evaporation, and recrystallized (n-hexane/ethyl acetate=1/15, V/V) to produce 8.56 g of Intermediate 1-6.

Step 7 Preparation of Compound 1

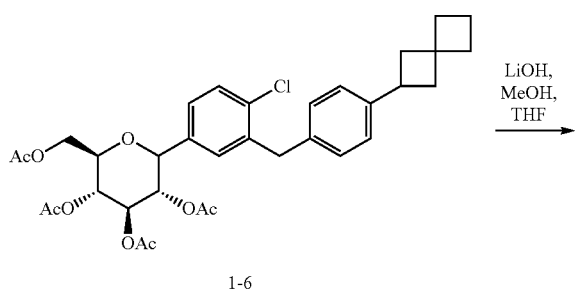

Example 4

Preparation of Compound 4

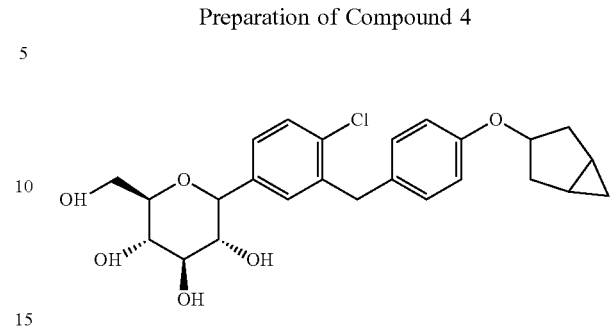

Intermediate 1-6 (6.29 g, 10.0 mmol) was dissolved in a mixed solution of tetrahydrofuran (100 mL) and methanol (100 mL). To the mixture was added a solution of lithium hydroxide monohydrate (4.4 g, 104 mmol) in water (50 mL) at 0° C. The reaction mixture was warmed up slowly to room temperature and stirred for 14 h. The reaction was monitored until the reaction completed. The reaction mixture was concentrated, and extracted with dichloromethane. The combined organic phase was washed with water and a saturated NaCl solution, dried, and concentrated to produce 3.90 g of Compound 1. Formula: $C_{26}H_{31}ClO_5$; Mw: 458.19; LC-MS $(M+H)^+$: 459

Step 1 Preparation of Intermediate 4-1

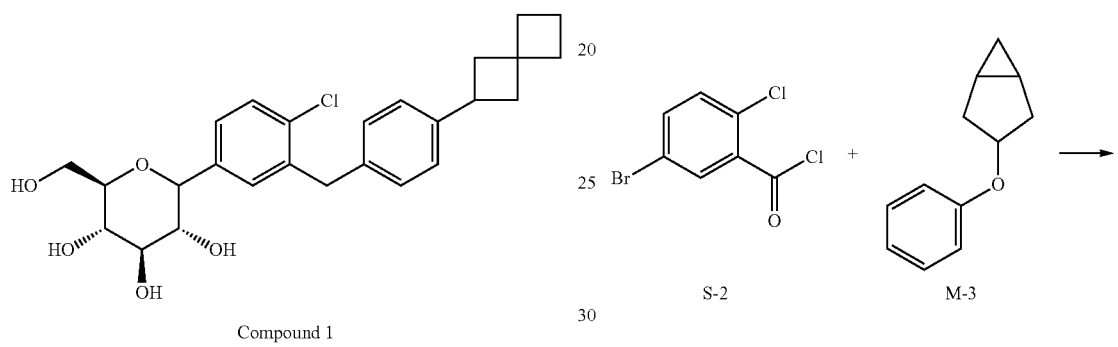

Example 3

Preparation of Compound 2

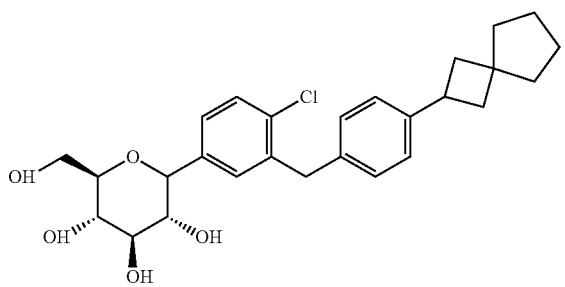 [SMILES: OC[C@H]1OC(c2ccc(Cl)c(Cc3ccc(C4CC5(CCCC5)C4)cc3)c2)[C@H](O)[C@@H](O)[C@@H]1O]

Compound 2 was prepared with reference of Example 1.
Formula: $C_{27}H_{33}ClO_5$; Mw: 472.20; LC-MS$(M+H)^+$: 473

A solution of aluminum trichloride (2.8 g, 21 mmol) in dichloromethane (25 mL) was cooled to 0° C., to which was slowly added Intermediate M-3 (3.7 g, 21.3 mmol) (prepared with reference to Example 13, step 1-3). The resulting mixture was stirred for 1 h while keeping it at 0° C. Then to the mixture was slowly added dropwise a solution of 2-chloro-5-bromo-benzoyl chloride (5.41 g, 21.3 mmol) (Intermediate S-2) in dichloromethane (15 mL). The reaction was monitored until the reaction completed. The reaction mixture was poured into ice-water (150 mL), and extracted with dichloromethane (3×100 mL). The organic phases were combined and washed respectively with a dilute hydrochloric acid (1N), water, NaOH (1N), and a saturated NaCl solution, and dried over anhydrous $Na_2SO_4$. The resulting organic phase was evaporated by rotation and purified by a column chromatography (n-hexane/ethyl acetate=1/20) to produce 8.00 g of the target Intermediate 4-1.

Step 2 Preparation of Intermediate 4-2

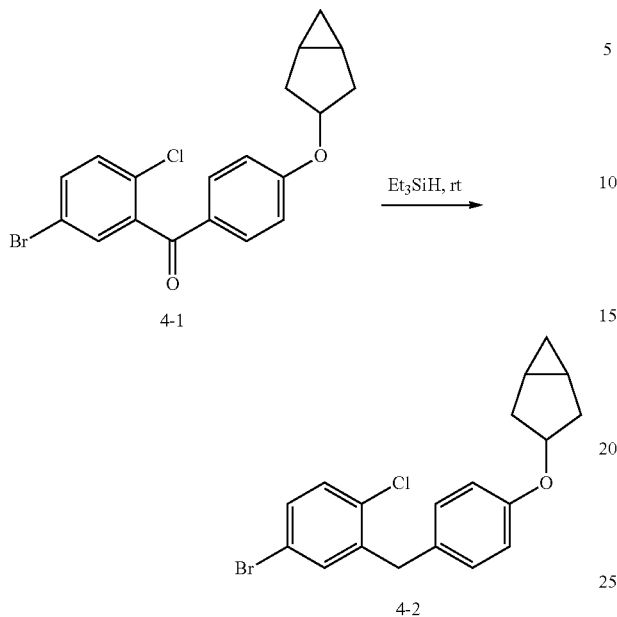

Intermediate 4-1 (15.64 g, 39.9 mmol) was dissolved in trifluoroacetic acid (30 mL). Then to the mixture was added triethylsilane (7.86 g, 67.6 mmol). The reaction mixture was heated to reflux for 16 h. To the reaction mixture was added a saturated aqueous sodium carbonate solution to adjust to pH=8. The reaction mixture was extracted with ethyl acetate to produce an organic phase. The organic phase was washed with a saturated NaCl solution, and dried in vacuum to produce 12.8 g of a crude product of Intermediate 4-2.

Step 3 Preparation of Intermediate 4-3

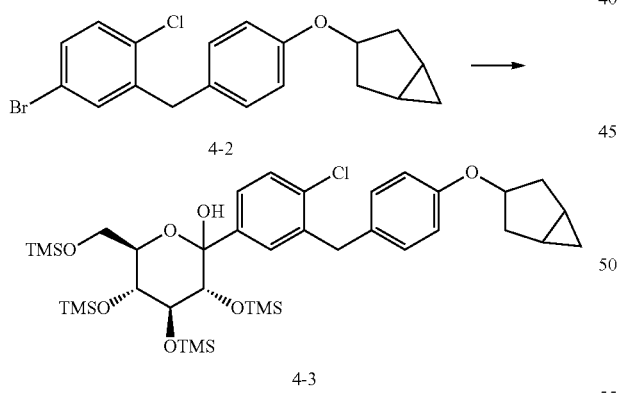

Intermediate 4-2 (2 g, 5.3 mmol) was dissolved anhydrous THF (10 mL). The resulting mixture was cooled to −78° C. Then to the mixture was slowly added dropwise n-BuLi (2.5M, 3 mL, 7.5 mmol) in a nitrogen protection. The resulting mixture was stirred for 3 h. Then to the mixture was slowly added dropwise a solution of (3R,4S,5R,6R)-3,4,5-tris(trimethylsilyloxy)-6-((trimethylsilyloxy)methyl)tetrahydro-2H-pyran-2-one (Intermediate 1) (2.7 g, 5.8 mmol) in n-hexane (20 mL) at −78° C., while the stirring was kept for 0.5 h. Then the reaction mixture was quenched with a saturated ammonium chloride solution (100 mL). The aqueous layer was extracted with ethyl acetate (3×200 mL). The combined organic phase was washed with water and a saturated NaCl solution, and evaporated by rotation to produce 3.2 g of Intermediate 4-3 as oil.

Step 4 Preparation of Intermediate 4-4

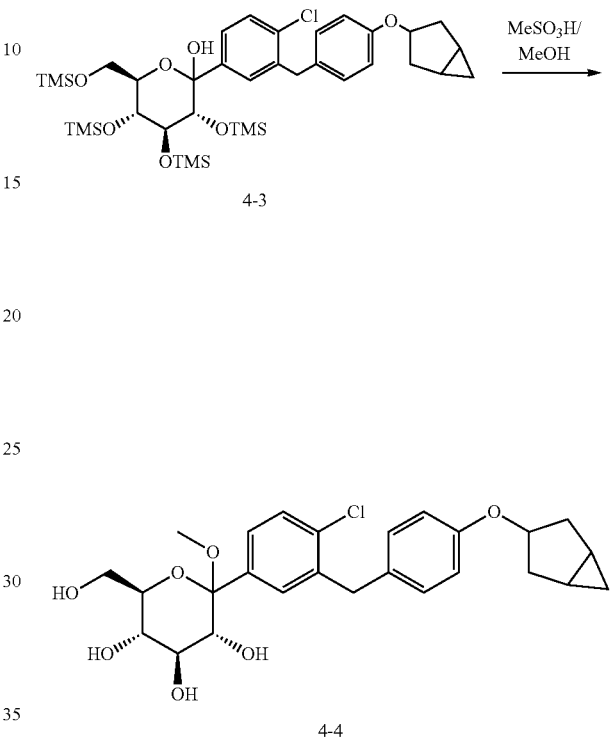

Intermediate 4-3 (3.2 g, 0.4 mmol) was dissolved in absolute anhydrous methanol (10 mL). The resulting mixture was cooled to 0° C. To the mixture was added a solution of methanesulfonic acid (1 mL) in anhydrous methanol (10 mL). The resulting mixture was slowly warmed up to room temperature and stirred for 16 h. The mixture was adjusted with an aqueous saturated NaHCO₃ solution to pH=8, and extracted with ethyl acetate. The combined organic phase was washed with water and a saturated NaCl solution, dried, and evaporated by rotation to produce 2.0 g of Intermediate 4-4.

Step 5 Preparation of Intermediate 4-5

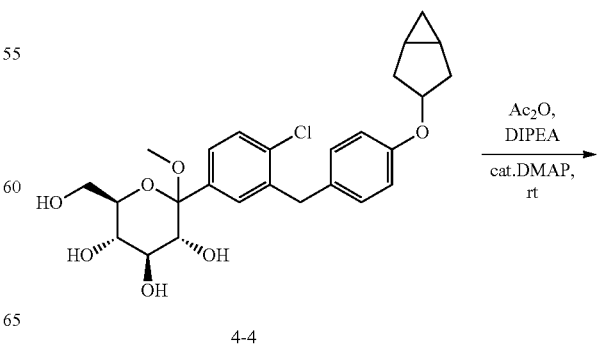

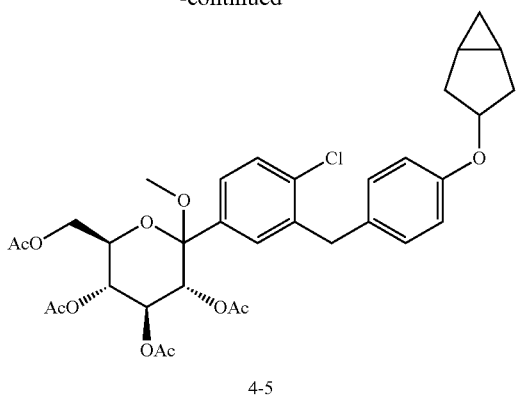

4-5

Intermediate 4-4 (2 g, 4.9 mmol), diisopropylethylamine (6.4 g, 49 mmol) and DMAP (10 mg) were dissolved in THF (100 mL). The resulting mixture was cooled to 0° C. To the mixture was slowly added acetic anhydride (4.9 g, 49 mmol). The mixture was stirred for 0.5 h. The reaction mixture was adjusted with a saturated aqueous sodium bicarbonate solution to pH=8, and extracted with ethyl acetate (5×60 mL). The combined organic phase was washed with water (100 mL) and a saturated NaCl solution (100 mL), dried, concentrated by rotary evaporation, and purified by a column chromatography to produce 1.8 g of Intermediate 4-5.

Step 6 Preparation of Intermediate 4-6

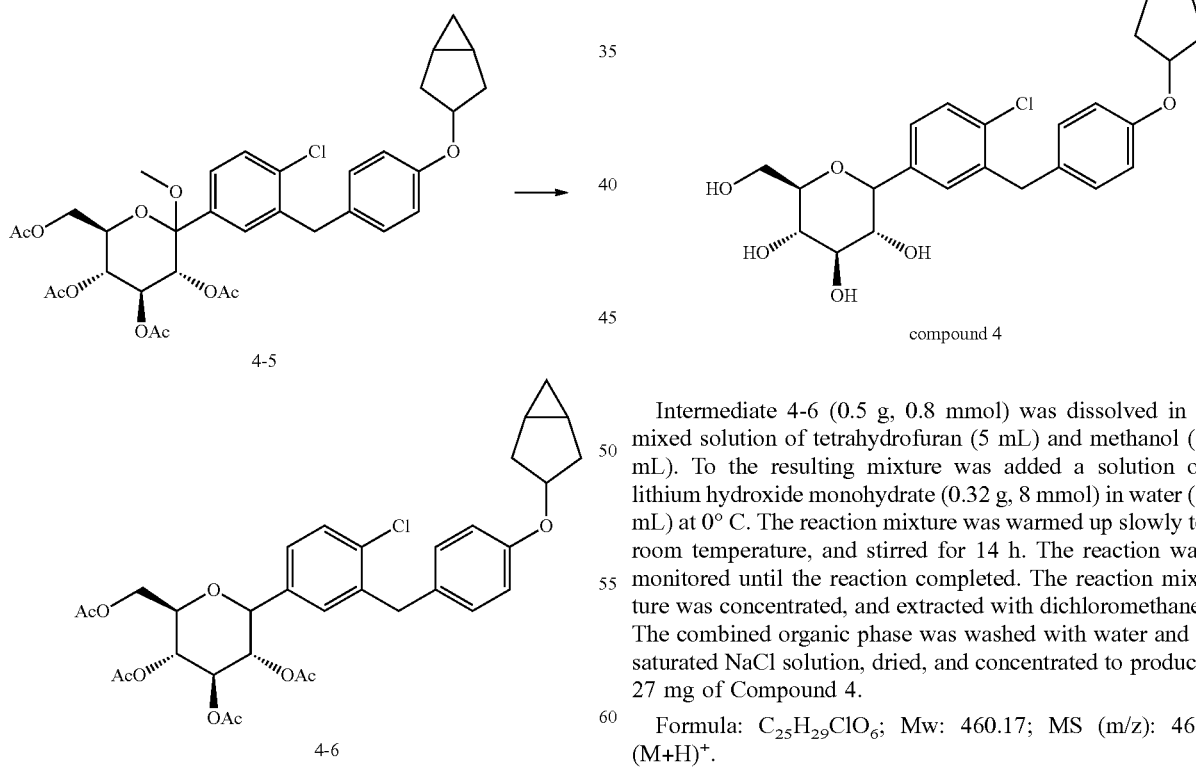

A solution of Intermediate 4-5 (1.8 g, 2.7 mmol) in acetonitrile (10 mL) was cooled to 10° C., to which was added triisopropylsilane (1.1 g, 7 mmol) and boron trifluoride-diethyl etherate (1.3 g, 9 mmol). The reaction was monitored until the reaction completed. The reaction mixture was quenched with a saturated sodium bicarbonate solution, and extracted with ethyl acetate (3×100 mL). The combined organic phase was washed with water and a saturated NaCl solution, dried, concentrated by rotary evaporation, and recrystallized (n-hexane/ethyl acetate=1/15, V/V) to produce 0.5 g of Intermediate 4-6.

Step 7 Preparation of Compound 4

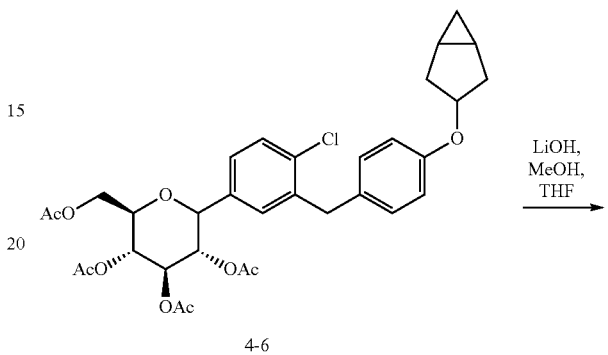

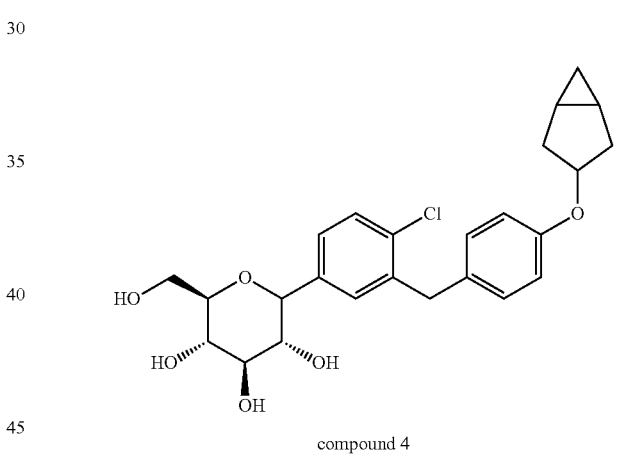

compound 4

Intermediate 4-6 (0.5 g, 0.8 mmol) was dissolved in a mixed solution of tetrahydrofuran (5 mL) and methanol (5 mL). To the resulting mixture was added a solution of lithium hydroxide monohydrate (0.32 g, 8 mmol) in water (5 mL) at 0° C. The reaction mixture was warmed up slowly to room temperature, and stirred for 14 h. The reaction was monitored until the reaction completed. The reaction mixture was concentrated, and extracted with dichloromethane. The combined organic phase was washed with water and a saturated NaCl solution, dried, and concentrated to produce 27 mg of Compound 4.

Formula: $C_{25}H_{29}ClO_6$; Mw: 460.17; MS (m/z): 461 (M+H)$^+$.

$^1$H-NMR: (MeOD, 400 MHz) δ: 7.33-7.26 (m, 3H), 7.08-7.05 (m, 2H), 6.76-6.74 (m, 2H), 4.43 (quint, 1H), 4.10-3.86 (m, 3H), 3.86 (d, 1H), 3.71-3.66 (m, 1H), 3.45-3.31 (m, 4H), 2.34-2.29 (m, 2H), 1.87-1.83 (m, 2H), 1.36-1.34 (m, 2H), 0.42 (dd, 1H), 0.10 (dd, 1H).

Example 5

Preparation of Compound 5

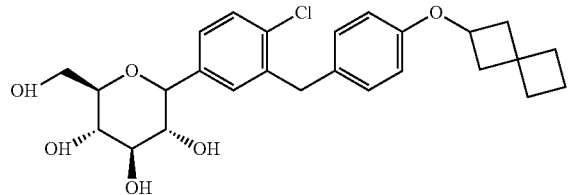 [SMILES: OC[C@H]1OC(c2ccc(Cl)c(Cc3ccc(OC4CC5(CCC5)C4)cc3)c2)[C@H](O)[C@@H](O)[C@@H]1O]

Compound 5 was prepared with reference of Example 4.
Formula: $C_{26}H_{31}ClO_6$; Mw: 474.18; LC-MS(M+H)$^+$: 475

Example 6

Preparation of Compound 6

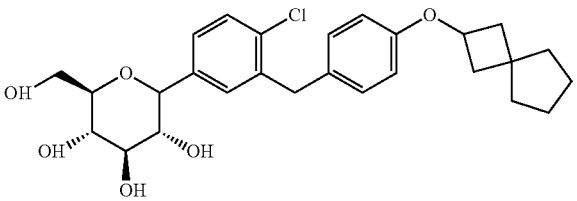 [SMILES: OC[C@H]1OC(c2ccc(Cl)c(Cc3ccc(OC4CC5(CCCC5)C4)cc3)c2)[C@H](O)[C@@H](O)[C@@H]1O]

Compound 6 was prepared with reference of Example 4.
Formula: $C_{27}H_{33}ClO_6$; Mw: 488.20; LC-MS(M+H)$^+$: 489

Example 7

Preparation of Compound 7

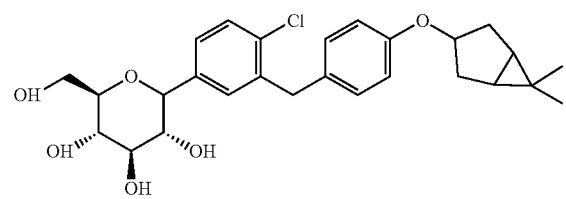 [SMILES: CC1(C)C2CC(Oc3ccc(Cc4cc(C5O[C@H](CO)[C@@H](O)[C@H](O)[C@H]5O)ccc4Cl)cc3)CC21]

Compound 7 was prepared with reference of Example 4.
Formula: $C_{27}H_{33}ClO_6$; Mw: 488.20; LC-MS(M+H)$^+$: 489

Example 8

Preparation of Compound 8

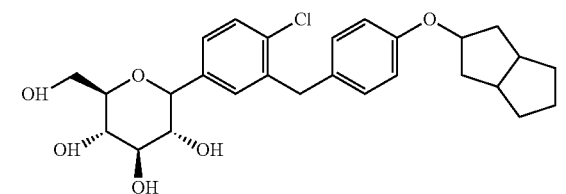 [SMILES: OC[C@H]1OC(c2ccc(Cl)c(Cc3ccc(OC4CC5CCCC5C4)cc3)c2)[C@H](O)[C@@H](O)[C@@H]1O]

Compound 8 was prepared with reference of Example 4.
Formula: $C_{27}H_{33}ClO_6$; Mw: 488.20; LC-MS(M+H)$^+$: 489

Example 9

Preparation of Compound 9

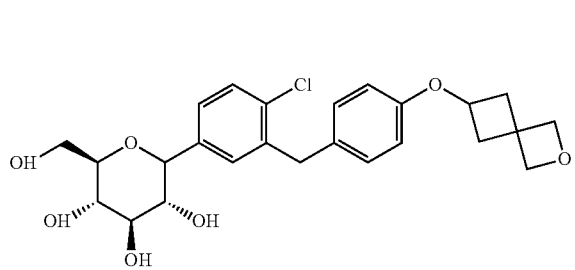 [SMILES: OC[C@H]1OC(c2ccc(Cl)c(Cc3ccc(OC4CC5(COC5)C4)cc3)c2)[C@H](O)[C@@H](O)[C@@H]1O]

Step 1 preparation of Intermediate 9-1

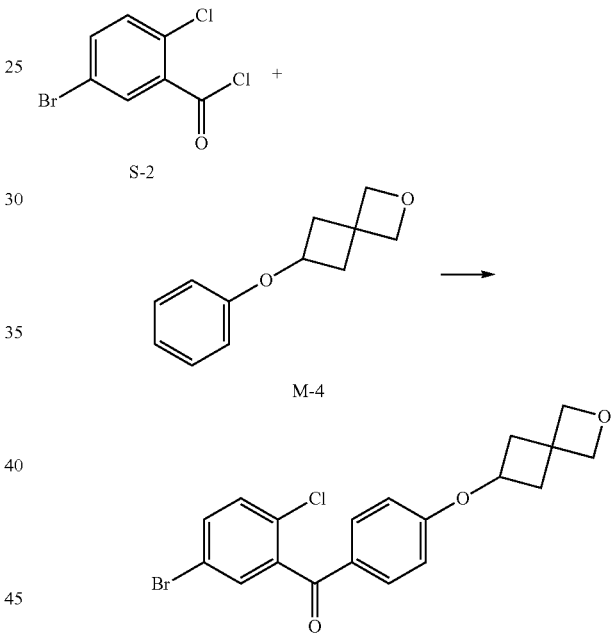

A solution of aluminum trichloride (2.8 g, 21 mmol) in dichloromethane (25 mL) was cooled to 0° C., to which was slowly added Intermediate M-4 (4.07 g, 21.3 mmol) (Intermediate M-4, prepared with reference to Example 13, Step 1-4). The resulting mixture was stirred for 1 h while keeping it at 0° C. Then to the mixture was slowly added dropwise a solution of 2-chloro-5-bromo-benzoyl chloride (Intermediate S-2) (5.41 g, 21.3 mmol) in dichloromethane (15 mL). The reaction was monitored until the reaction completed. The reaction mixture was poured into ice-water (150 mL), and extracted with dichloromethane (3×100 mL). The organic phases were combined and washed respectively with a dilute hydrochloric acid (1N), water, NaOH (1N), and a saturated NaCl solution, and dried over anhydrous $Na_2SO_4$. The resulting organic phase was evaporated by rotation and purified by a column chromatography (n-hexane/ethyl acetate=1/20) to produce 8.6 g of the target compound, Intermediate 9-1.

Step 2 Preparation of Intermediate 9-2

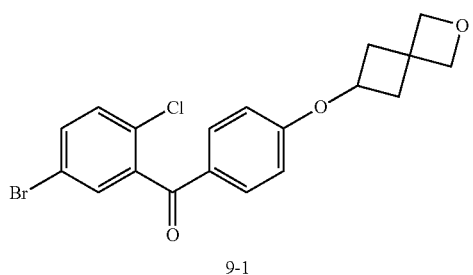

9-1

Step 3 Preparation of Intermediate 9-3

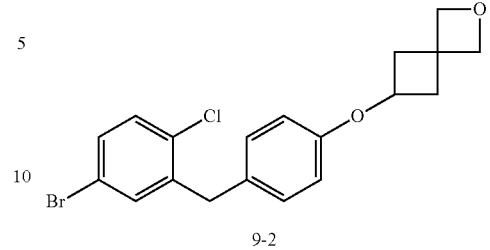

9-2

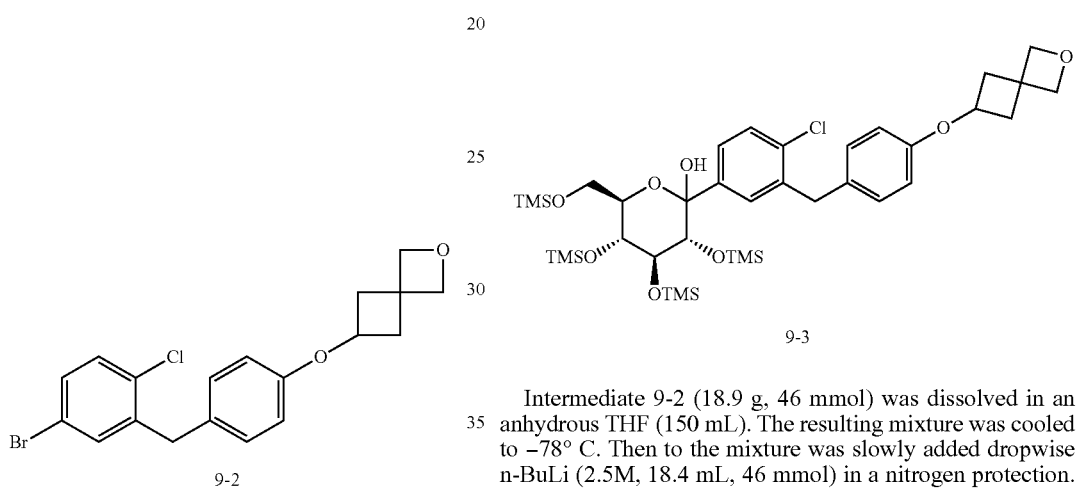

9-2

9-3

Intermediate 9-1 (16.9 g, 39.9 mmol) was dissolved in trifluoroacetic acid (30 mL). Then to the resulting mixture was added triethylsilane (7.86 g, 67.6 mmol). The reaction mixture was heated to reflux for 16 h, adjusted with a saturated aqueous sodium carbonate solution to pH=8, and extracted with ethyl acetate to obtain an organic phase. The organic phase was washed with a saturated NaCl solution, and dried in vacuum to produce 14.0 g of a crude product of Intermediate 9-2.

Intermediate 9-2 (18.9 g, 46 mmol) was dissolved in an anhydrous THF (150 mL). The resulting mixture was cooled to −78° C. Then to the mixture was slowly added dropwise n-BuLi (2.5M, 18.4 mL, 46 mmol) in a nitrogen protection. The resulting mixture was stirred for 3 h. Then to the mixture was added dropwise slowly at −78° C. a solution of (3R,4S,5R,6R)-3,4,5-tris(trimethylsilyloxy)-6-((trimethylsilyloxy)methyl)tetrahydro-2H-pyran-2-one (23.6 g, 50.6 mmol) in n-hexane (300 mL), while the stirring was kept for 0.5 h. Then the reaction mixture was quenched with an aqueous saturated ammonium chloride solution (100 mL). The resulting aqueous layer was extracted with ethyl acetate (3×100 mL). The combined organic phase was washed with water and a saturated NaCl solution, and evaporated by rotation to produce 19.2 g of Intermediate 9-3 as oil.

Step 4 Preparation of Intermediate 9-4

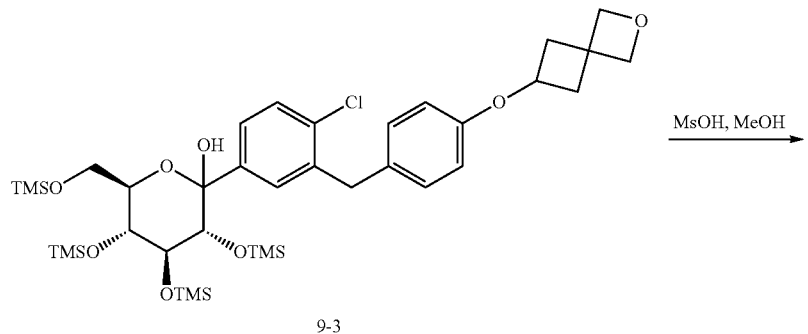

9-3

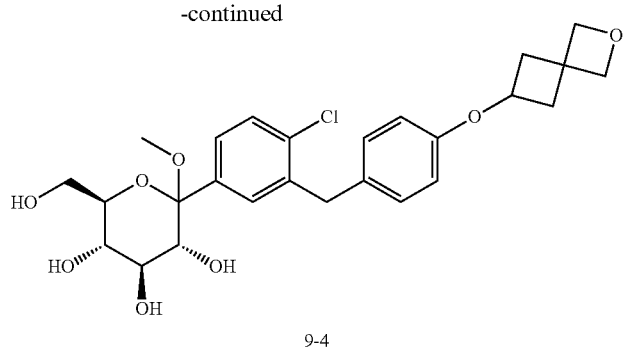

9-4

Intermediate 9-3 (4.93 g, 10 mmol) was dissolved in absolute anhydrous methanol (10 mL). The resulting mixture was cooled to 0° C. To the mixture was added a solution of methanesulfonic acid (0.4 mL) in anhydrous methanol (10 mL). The resulting mixture was slowly warmed up to room temperature and stirred for 16 h, adjusted with an aqueous saturated NaHCO$_3$ solution to pH=8, and extracted with ethyl acetate. The combined organic phase was washed with water and a saturated NaCl solution, dried, and evaporated by rotation to produce 5.07 g of Intermediate 9-4.

Step 5 Preparation of Intermediate 9-5

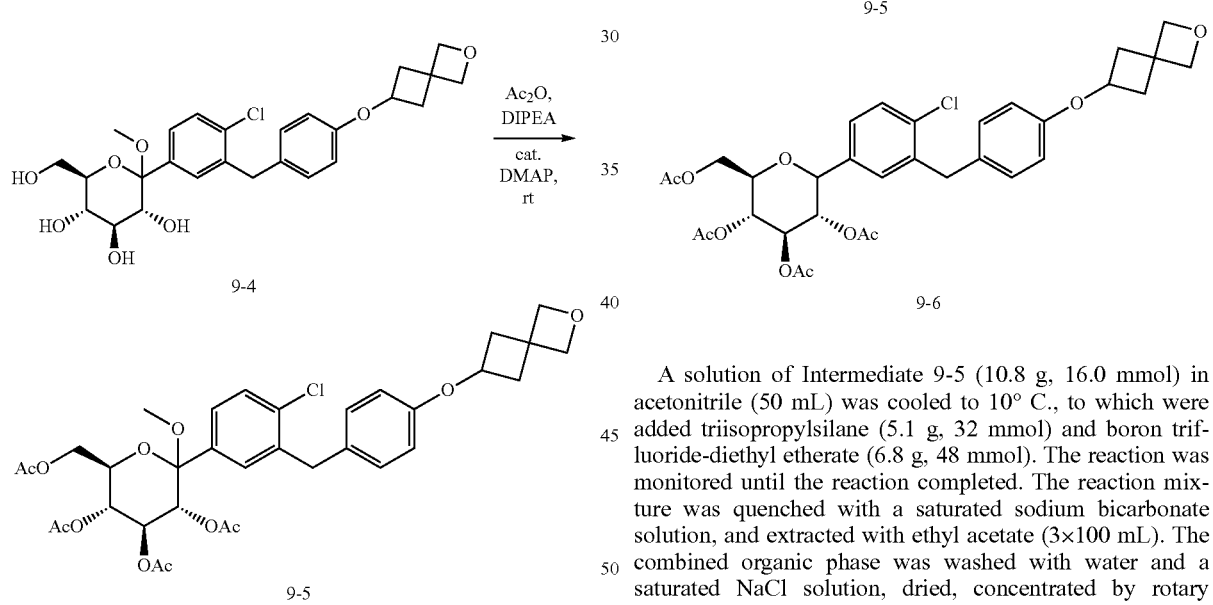

Ac = acetyl

Intermediate 9-4 (4.61 g, 9.1 mmol), diisopropylethylamine (9.4 g, 72.8 mmol) and DMAP (10 mg) were dissolved in THF (100 mL). The resulting mixture was cooled to 0° C. To the mixture was slowly added acetic anhydride (7.43 g, 72.8 mmol). The mixture was stirred for 0.5 h. The reaction mixture was adjusted with a saturated aqueous sodium bicarbonate solution to pH=8, and extracted with ethyl acetate (3×60 mL). The combined organic phase was washed with water (70 mL) and a saturated NaCl solution (70 mL), dried, concentrated by rotary evaporation, and purified by a column chromatography to produce 4.91 g of Intermediate 9-5.

Step 6 Preparation of Intermediate 9-6

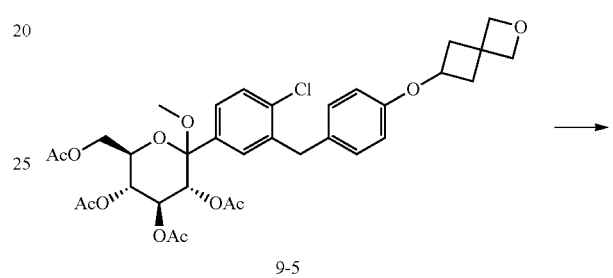

9-5

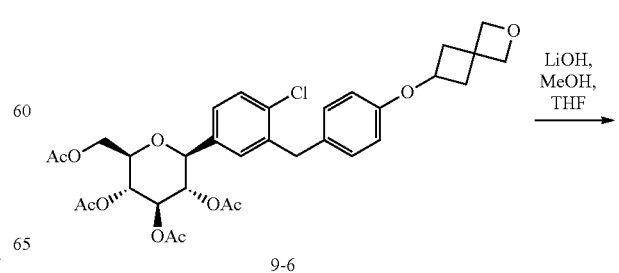

9-6

A solution of Intermediate 9-5 (10.8 g, 16.0 mmol) in acetonitrile (50 mL) was cooled to 10° C., to which were added triisopropylsilane (5.1 g, 32 mmol) and boron trifluoride-diethyl etherate (6.8 g, 48 mmol). The reaction was monitored until the reaction completed. The reaction mixture was quenched with a saturated sodium bicarbonate solution, and extracted with ethyl acetate (3×100 mL). The combined organic phase was washed with water and a saturated NaCl solution, dried, concentrated by rotary evaporation, and recrystallized (n-hexane/ethyl acetate=1/15, V/V) to produce 8.38 g of Intermediate 9-6.

Step 7 Preparation of Intermediate 9-7

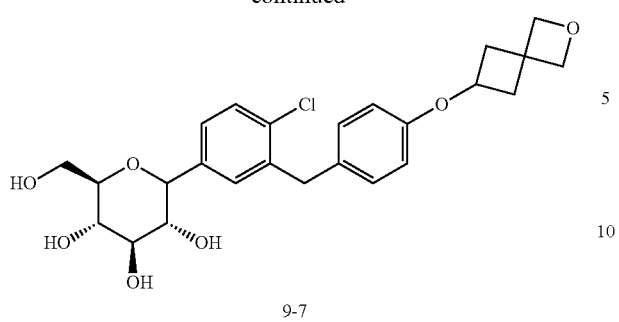

9-7

Intermediate 9-6 (6.47 g, 10.0 mmol) was dissolved in a mixed solution of tetrahydrofuran (100 mL) and methanol (100 mL). To the resulting mixture was added a solution of lithium hydroxide monohydrate (4.4 g, 104 mmol) in water (50 mL) at 0° C. The reaction mixture was warmed up slowly to room temperature, and stirred for 14 h. The reaction was monitored until the reaction completed. The reaction mixture was concentrated, and extracted with dichloromethane. The combined organic phase was washed with water and a saturated NaCl solution, dried, and concentrated to produce 4.10 g of Intermediate 9-7.

Formula: $C_{26}H_{29}ClO_7$; Mw: 476.16; LC-MS (M+H)$^+$: 477

Example 10

Preparation of Compound 10

Step 1 Preparation of Intermediate 10-1

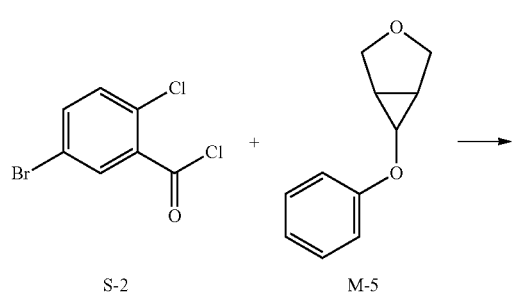

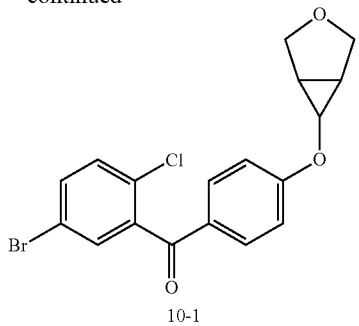

10-1

A solution of aluminum trichloride (2.8 g, 21 mmol) in dichloromethane (25 mL) was cooled to 0° C., to which was slowly added Intermediate M-5 (3.8 g, 21.3 mmol) (Intermediate M-5, prepared with reference to Example 13, step 1-3). The mixture was stirred for 1 h while keeping it at 0° C. Then to the mixture was slowly added dropwise a solution of 2-chloro-5-bromo-benzoyl chloride (Intermediate S-2) (5.4 g, 21.3 mmol) in dichloromethane (15 mL). The reaction was monitored until the reaction completed. The reaction mixture was poured into ice-water (150 mL), and extracted with dichloromethane (3×100 mL). The organic phases were combined and washed respectively with a dilute hydrochloric acid (1N), water, NaOH (1N), and a saturated NaCl solution, and dried over anhydrous $Na_2SO_4$. The resulting organic phase was evaporated by rotation and purified by a column chromatography (n-hexane/ethyl acetate=1/20) to produce 7.94 g of Intermediate 10-1.

Step 2 Preparation of Intermediate 10-2

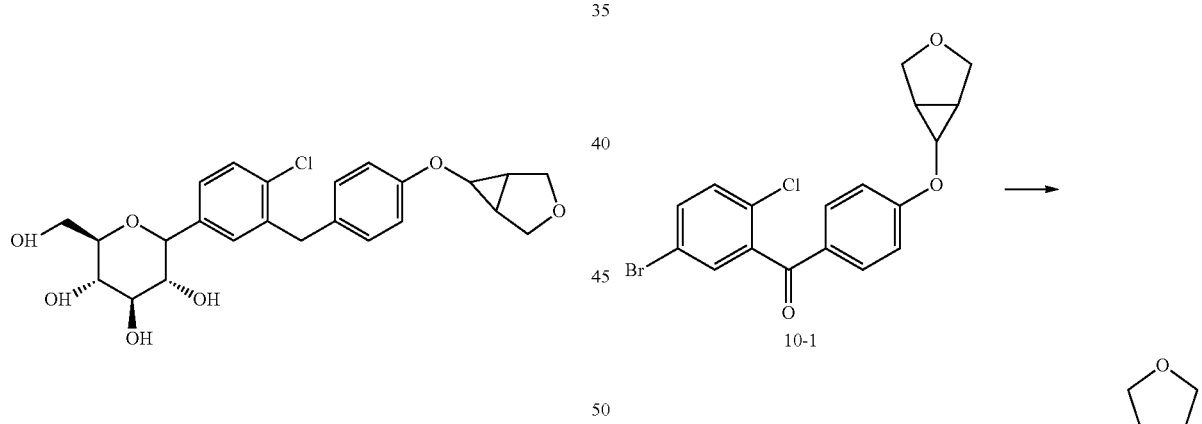

Intermediate 10-1 (15.7 g, 39.9 mmol) was dissolved in trifluoroacetic acid (30 mL). Then to the resulting mixture was added triethylsilane (7.86 g, 67.6 mmol). The reaction mixture was heated to reflux for 16 h, and adjusted with a saturated aqueous sodium carbonate solution to pH=8. The resulting mixture was extracted with ethyl acetate to produce an organic phase. The organic phase was washed with a saturated NaCl solution, and dried in vacuum to produce 13.3 g of a crude product of Intermediate 10-2.

Step 3 Preparation of Intermediate 10-3

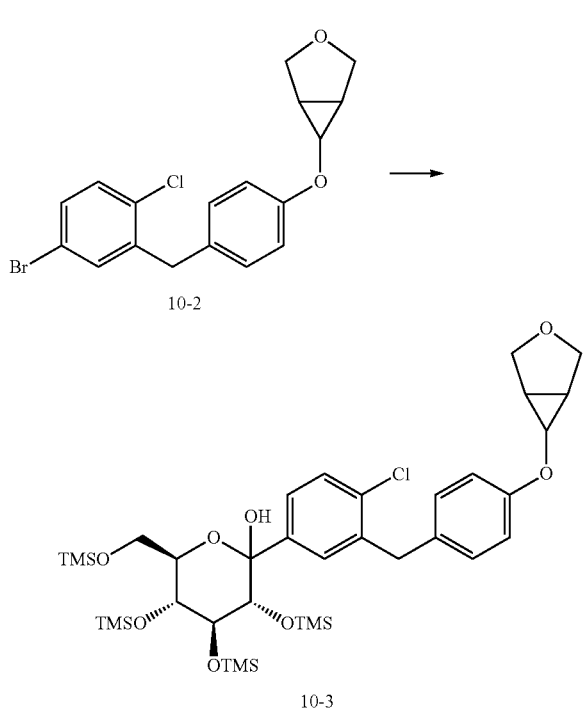

Intermediate 10-2 (17.5 g, 46 mmol) was dissolved in anhydrous THF (150 mL). The resulting mixture was cooled to −78° C. Then to the mixture was slowly added dropwise n-BuLi (2.5M, 18.4 mL, 46 mmol) in a nitrogen protection. The resulting mixture was stirred for 3 h. Then to the mixture was added dropwise slowly a solution of (3R,4S,5R,6R)-3,4,5-tris(trimethylsilyloxy)-6-((trimethylsilyloxy)methyl)tetrahydro-2H-pyran-2-one (23.6 g, 50.6 mmol) in n-hexane (300 mL) at −78° C., while the stirring was kept for 0.5 h. Then the reaction mixture was quenched with an aqueous saturated ammonium chloride solution (100 mL). The resulting aqueous layer was extracted with ethyl acetate (3×100 mL). The combined organic phase was washed with water and a saturated NaCl solution, and evaporated by rotation to produce 18.7 g of Intermediate 10-3 as oil.

Step 4 Preparation of Intermediate 10-4

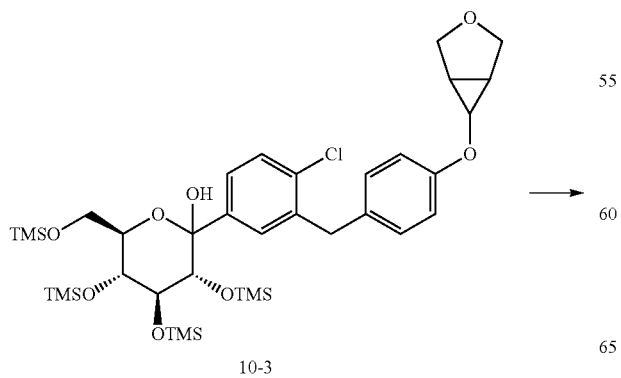

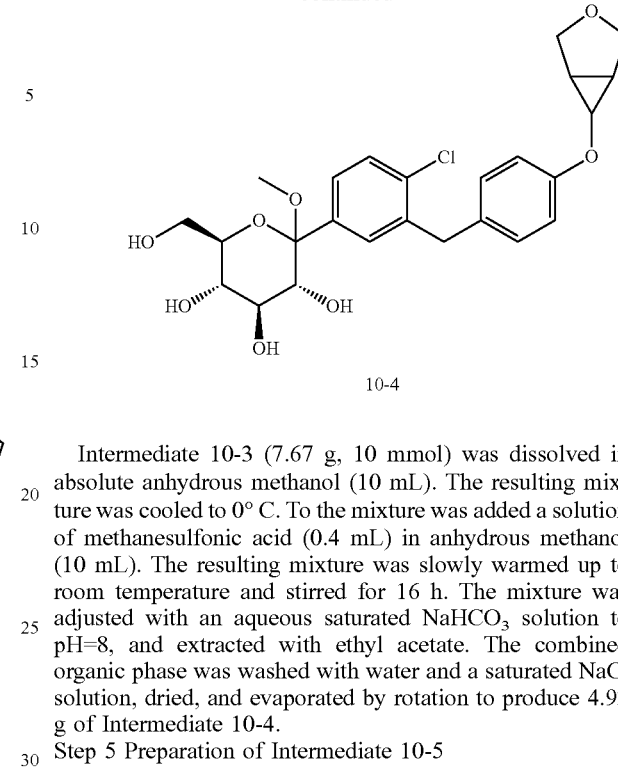

Intermediate 10-3 (7.67 g, 10 mmol) was dissolved in absolute anhydrous methanol (10 mL). The resulting mixture was cooled to 0° C. To the mixture was added a solution of methanesulfonic acid (0.4 mL) in anhydrous methanol (10 mL). The resulting mixture was slowly warmed up to room temperature and stirred for 16 h. The mixture was adjusted with an aqueous saturated NaHCO₃ solution to pH=8, and extracted with ethyl acetate. The combined organic phase was washed with water and a saturated NaCl solution, dried, and evaporated by rotation to produce 4.93 g of Intermediate 10-4.

Step 5 Preparation of Intermediate 10-5

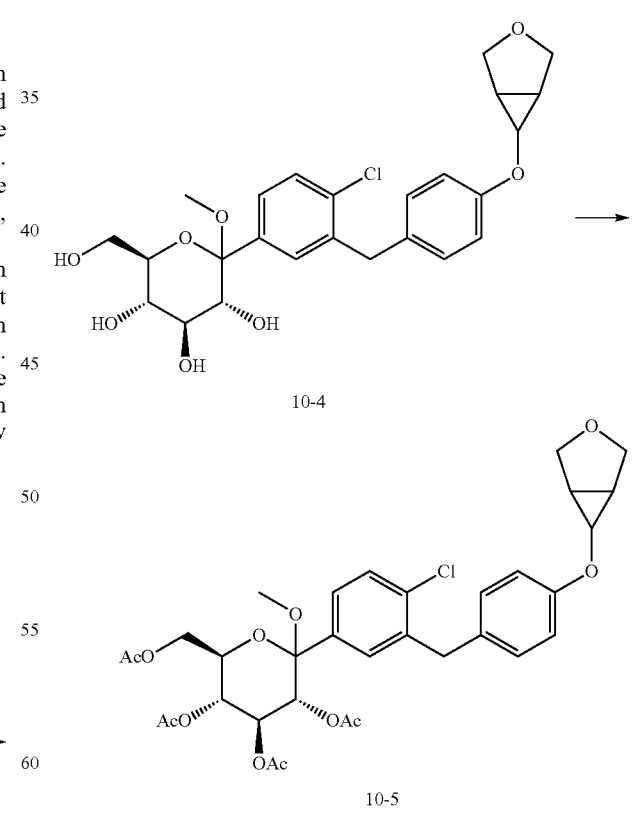

Intermediate 10-4 (4.48 g, 9.1 mmol), diisopropylethylamine (9.4 g, 72.8 mmol) and DMAP (10 mg) were dissolved in THF (100 mL). The resulting mixture was cooled to 0° C. To the mixture was slowly added acetic anhydride (7.43 g, 72.8 mmol). The mixture was stirred for 0.5 h. The reaction mixture was adjusted with a saturated aqueous sodium bicarbonate solution to pH=8, and extracted with ethyl acetate (3×60 mL). The combined organic phase was washed with water (70 mL) and a saturated NaCl solution (70 mL), dried, concentrated by rotary evaporation, and purified by a column chromatography to produce 4.87 g of Intermediate 10-5.

Step 6 Preparation of Intermediate 10-6

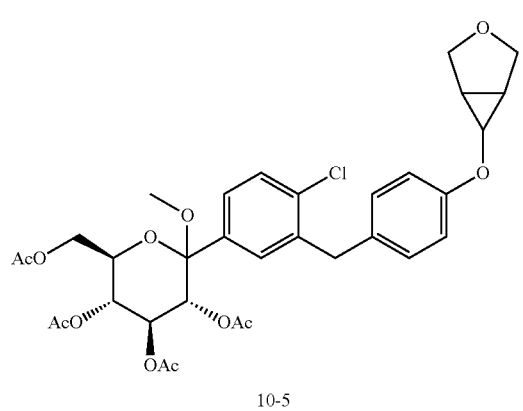

10-5

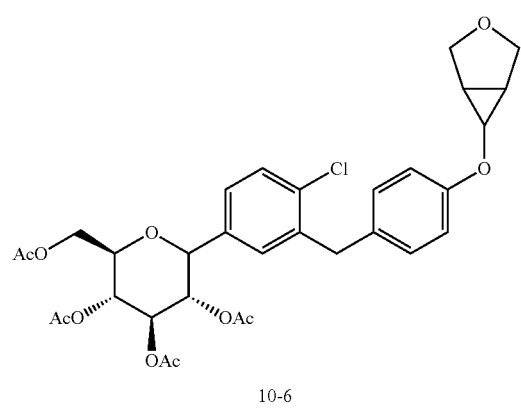

10-6

A solution of Intermediate 10-5 (10.6 g, 16.0 mmol) in acetonitrile (50 mL) was cooled to 10° C. To the resulting mixture were added triisopropylsilane (5.1 g, 32 mmol) and boron trifluoride-diethyl etherate (6.8 g, 48 mmol). The reaction was monitored until the reaction completed. The reaction mixture was quenched with a saturated sodium bicarbonate solution, and extracted with ethyl acetate (3×100 mL). The combined organic phase was washed with water and a saturated NaCl solution, dried, concentrated by rotary evaporation, and recrystallized (n-hexane/ethyl acetate=1/15, V/V) to produce 8.60 g of Intermediate 10-6.

Step 7 Preparation of Compound 10

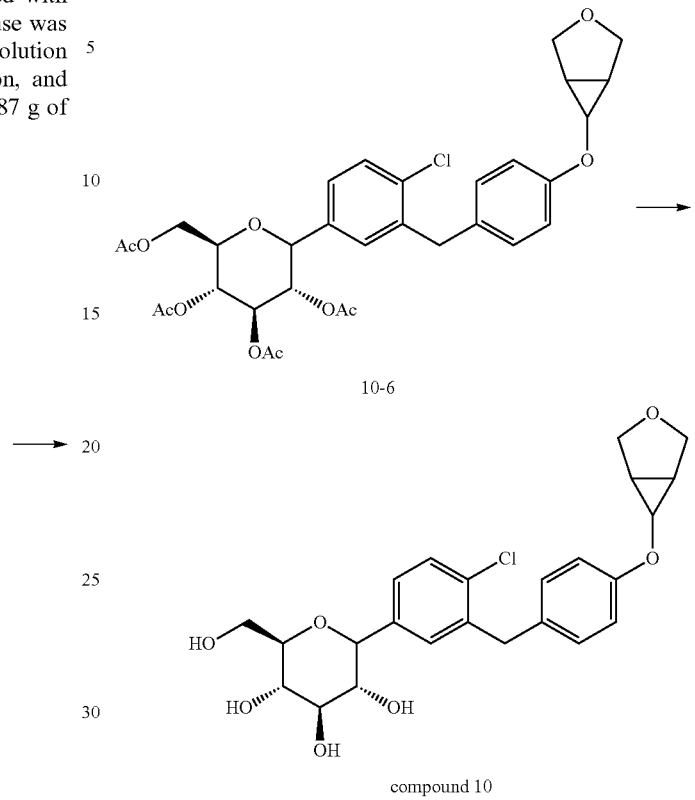

Intermediate 10-6 (6.33 g, 10.0 mmol) was dissolved in a mixed solution of tetrahydrofuran (100 mL) and methanol (100 mL). To the resulting mixture was added a solution of lithium hydroxide monohydrate (having a content of 75%) (4.4 g, 104 mmol) in water (50 mL) at 0° C. The reaction mixture was warmed up slowly to room temperature, and stirred for 14 h. The reaction was monitored until the reaction completed. The reaction mixture was concentrated, and extracted with dichloromethane. The combined organic phase was washed with water and a saturated NaCl solution, dried, and concentrated to produce 4.17 g of Compound 10.

Formula: $C_{24}H_{27}ClO_7$; Mw: 463; MS(m/z): 463.2 $(M+H)^+$.

$^1$H-NMR: (MeOD, 400 MHz) δ: 7.35-7.33 (m, 2H), 7.26-7.29 (d, 1H), 7.11-7.13 (m, 2H), 6.87-6.89 (m, 2H), 4.10-4.01 (m, 5H), 3.88 (d, 1H), 3.77-3.67 (m, 3H), 3.45-3.38 (m, 5H), 1.95 (s, 2H).

Example 11

Preparation of Compound 11

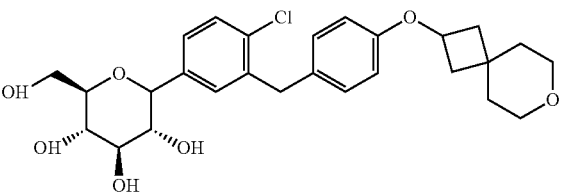 [SMILES: OC[C@H]1OC(c2ccc(Cl)c(Cc3ccc(OC4CC5(CCOCC5)C4)cc3)c2)[C@H](O)[C@@H](O)[C@@H]1O]

Compound 11 was prepared with reference of Example 9.
Formula: $C_{27}H_{33}CO_7$; Mw: 504.19; LC-MS (M+H)$^+$: 505

Example 12

Preparation of Compound 12

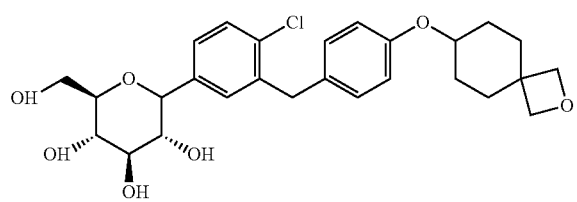 [SMILES: OC[C@H]1OC(c2ccc(Cl)c(Cc3ccc(OC4CCC5(CC4)COC5)cc3)c2)[C@H](O)[C@@H](O)[C@@H]1O]

Compound 12 was prepared with reference of Example 9.
Formula: $C_{27}H_{33}ClO_7$; Mw: 504.19; LC-MS (M+H)$^+$: 505

Example 13

Preparation of Compound 13

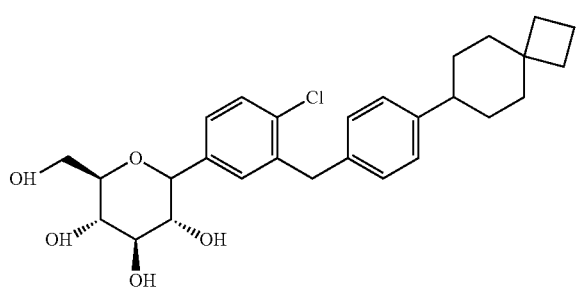 [SMILES: OC[C@H]1OC(c2ccc(Cl)c(Cc3ccc(C4CCC5(CCC5)CC4)cc3)c2)[C@H](O)[C@@H](O)[C@@H]1O]

Step 1 Preparation of Intermediate 13-1

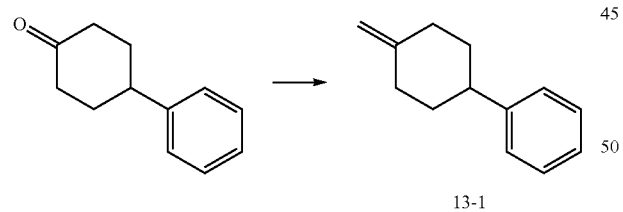

In a 250 mL reaction vessel, triphenylmethyl phosphonium bromide (5.7 g, 16.4 mmol) was dissolved in 100 mL tetrahydrofuran. To the resulting mixture was slowly added potassium tertbutoxide (1.8 g, 16.4 mmol) at 0° C. After the stirring was continued for 0.5 hr, 4-phenylcyclohexanone (17.4 g, 10 mmol) was dissolved in 30 mL tetrahydrofuran, and the resulting mixture was added dropwise to the reaction vessel. After the dropwise addition, the reaction mixture was reacted at room temperature for 12 h. The reaction mixture was concentrated in vacuum, and dispersed in 1 L petroleum ether. The resulting mixture was quickly filtered through a silica-gel column, and concentrated to produce the target Intermediate 13-1 (12.7 g).

Step 2 Preparation of Intermediate 13-2

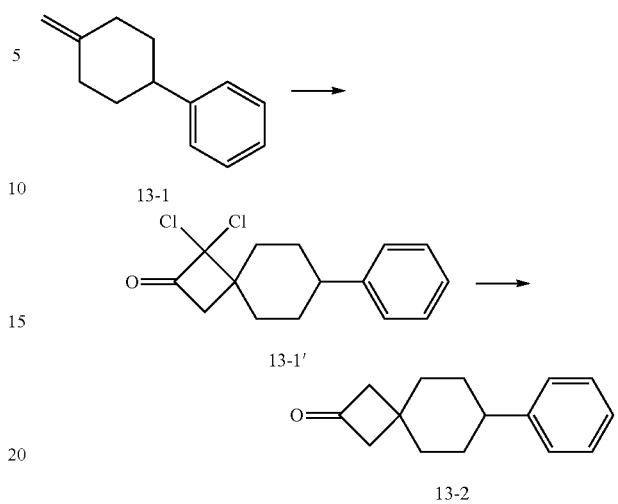

In a 500 mL reaction vessel, Intermediate 13-1 (7.8 g, 45.68 mmol) and Zn—Cu alloy (22.87 g, 228.4 mmol) were dispersed in 200 mL anhydrous ether. To the reaction vessel was slowly added dropwise a dispersion of trichloroacetyl chloride (24.66 g, 137.04 mmol) in 50 mL ethylene glycol dimethyl ether at 0° C. After the completion of dropwise addition, the resulting mixture was reacted at room temperature for 18 hr. The reaction mixture was slowly poured into 500 mL of a saturated aqueous sodium bicarbonate solution. The resulting mixture was extracted with anhydrous ether for three times (200 mL×3). The organic phases were combined, washed with a saturated NaCl solution, dried over anhydrous sodium sulfate, and concentrated in vacuum to produce a residue, which was dissolved in 200 L anhydrous methanol. Then to the resulting mixture were added activated Zn powder (5.36 g, 77.88 mmol) and ammonium chloride (2.76 g, 51.00 mmol). The resulting mixture was reacted under reflux for 4 h, filtered, concentrated and purified with a silica-gel column chromatography (PE/EA=1:10-1:3) to produce Intermediate 13-2 (5.8 g).

Step 3 Preparation of Intermediate 13-3

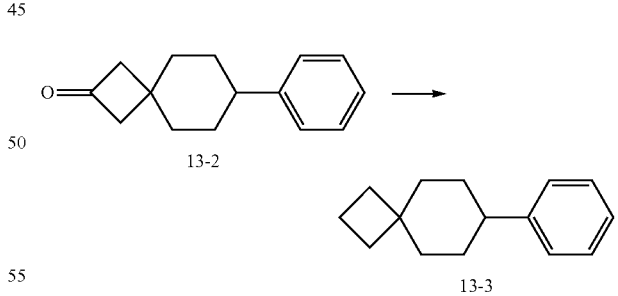

In a 250 mL reaction vessel, Intermediate 13-2 (5.0 g, 23.4 mmol), hydrazine hydrate (8.10 g, 201 mmol) and sodium hydroxide (5.85 g, 146.4 mmol) were dissolved in 100 mL triethylene glycol. The resulting mixture was reacted under reflux for 1 h. After removing the reflux device, the reaction temperature was raised up to 200° C. and the reaction mixture was reacted for 3 h, cooled, extracted with ethyl ether, concentrated, and purified with a silica-gel column chromatography to produce Intermediate 13-3 (4.4 g).

Step 4 Preparation of Intermediate 13-4

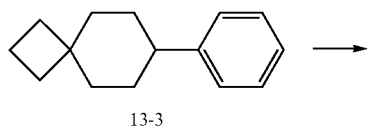

13-3

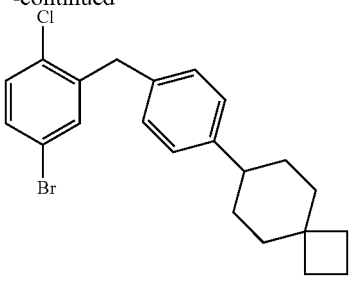

13-5

In a 250 mL reaction vessel, Intermediate 13-4 (2 g, 4.9 mmol) and triethylsilane (1.1 g, 10 mmol) were dissolved in 20 mL acetonitrile. To the resulting mixture was added dropwise boron trifluoride-diethyl etherate (2.8 mL, 20 mmol) in an ice-water bath. After the completion of dropwise addition, the resulting mixture was stirred at room temperature overnight. The reaction solution was poured into 100 mL ice-water, and extracted with ethyl acetate (100 mL×3). The organic phases were combined, washed with a saturated NaCl solution, dried over anhydrous sodium sulfate, concentrated, and purified with a silica-gel column chromatography (PE/EA=15:1) to produce 1.5 g Intermediate 13-5.

Step 6 Preparation of Intermediate 13-6

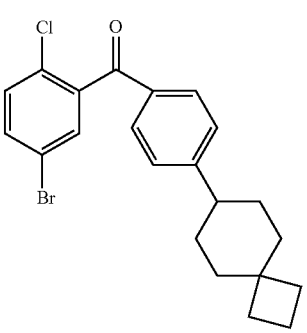

13-4

In a 250 mL reaction vessel, 5-bromo-2-chlorobenzoic acid (1.9 g, 8 mmol) and 0.2 mL DMF were mixed in 20 mL dichloromethane. To the resulting mixture was slowly added oxalyl chloride (5 g, 40 mmol). The reaction was continued for 0.5 h under stirring. After concentration, the resulting mixture was re-dissolved in 20 mL dichloromethane. To the resulting mixture was added anhydrous aluminum trichloride (1.6 g, 12 mmol). Intermediate 13-3 (2.4 g, 12 mmol) was dissolved in 10 mL dichloromethane at 0° C., and the resulting mixture was slowly added dropwise to the reaction vessel. After the completion of dropwise addition, the resulting mixture was stirred at room temperature for 18 h, and poured into 50 mL ice-water. The resulting mixture was extracted with dichloromethane (100 mL×3). The organic phases were combined, washed with a saturated NaCl solution, dried over anhydrous sodium sulfate, concentrated and purified with a silica-gel column chromatography (PE/EA=10:1) to produce Intermediate 13-4 (2.0 g).

Step 5 Preparation of Intermediate 13-5

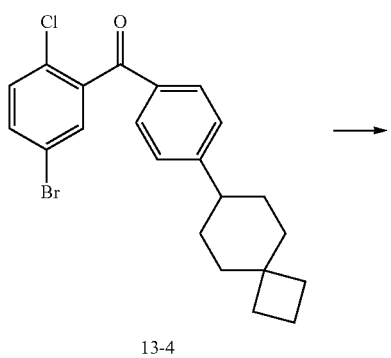

13-4

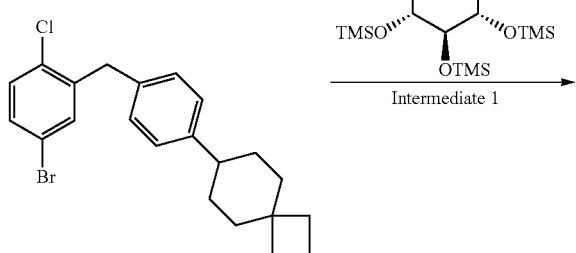

13-5

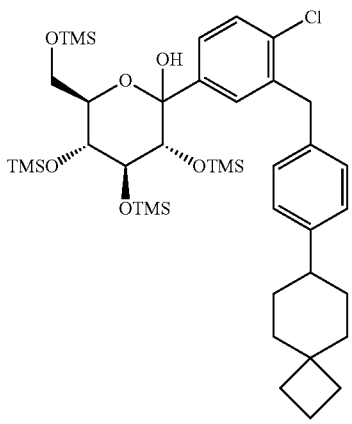

13-6

In a 250 mL reaction vessel, Intermediate 13-5 (0.8 g, 2 mmol) was dissolved in 15 mL anhydrous tetrahydrofuran in a nitrogen protection. At −78° C., to the reaction vessel was added dropwise n-butyl lithium (2.4M, 1 mL, 2.4 mmol) at a temperature not higher than −75° C. While the low temperature condition was maintained, the reaction mixture was reacted for 3 h. Intermediate 1 (1 g, 2.1 mmol) was dissolved in 5 mL tetrahydrofuran, and the resulting mixture was slowly added dropwise to the reaction vessel. After the temperature naturally rose to room temperature, the reaction was continued for 1 h. Into the reaction mixture was poured 100 mL of an aqueous saturated ammonium chloride solution. The resulting mixture was extracted with ethyl acetate (100 mL×3). The organic phases were combined, washed with a saturated NaCl solution, dried over anhydrous sodium sulfate, and concentrated to produce a crude product of Intermediate 13-6, which was directly used in the next reaction.

Step 7 Preparation of Intermediate 13-7

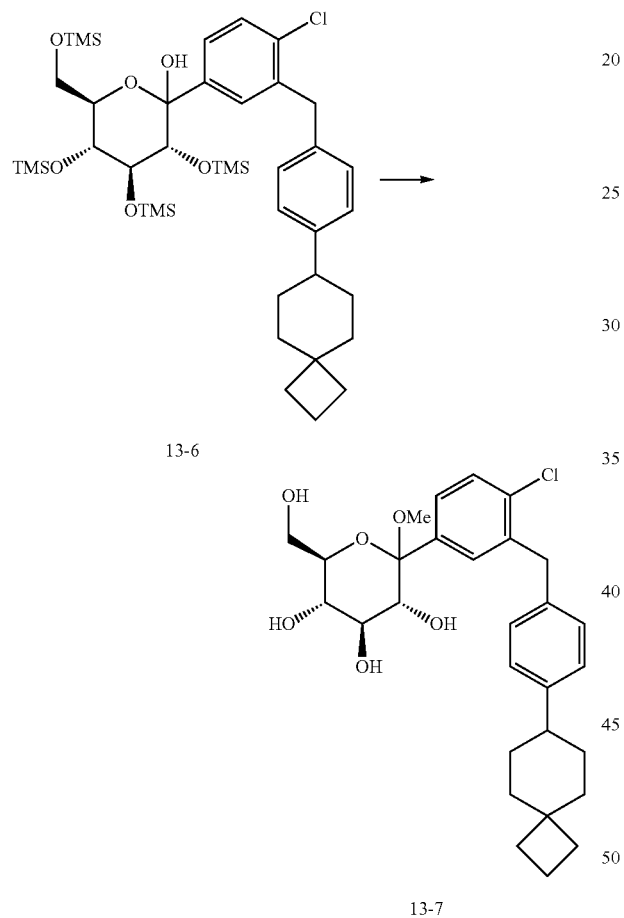

In a 50 mL reaction vessel, the crude product of Intermediate 13-6 from the above step was dissolved in 20 mL anhydrous methanol. Under cooling in an ice-water bath, to the reaction vessel was added dropwise a dispersion of methanesulfonic acid (0.4 mL) in 5 mL methanol. The resulting mixture was reacted at room temperature for 3 h. The reaction mixture was added dropwise to 100 mL of a saturated aqueous sodium bicarbonate solution. The resulting mixture was extracted with ethyl acetate (100 mL×3). The organic phases were combined, washed with a saturated NaCl solution, dried over anhydrous sodium sulfate, and concentrated to produce a crude product of Intermediate 13-7, which was directly used in the next reaction.

Step 8 Preparation of Intermediate 13-8

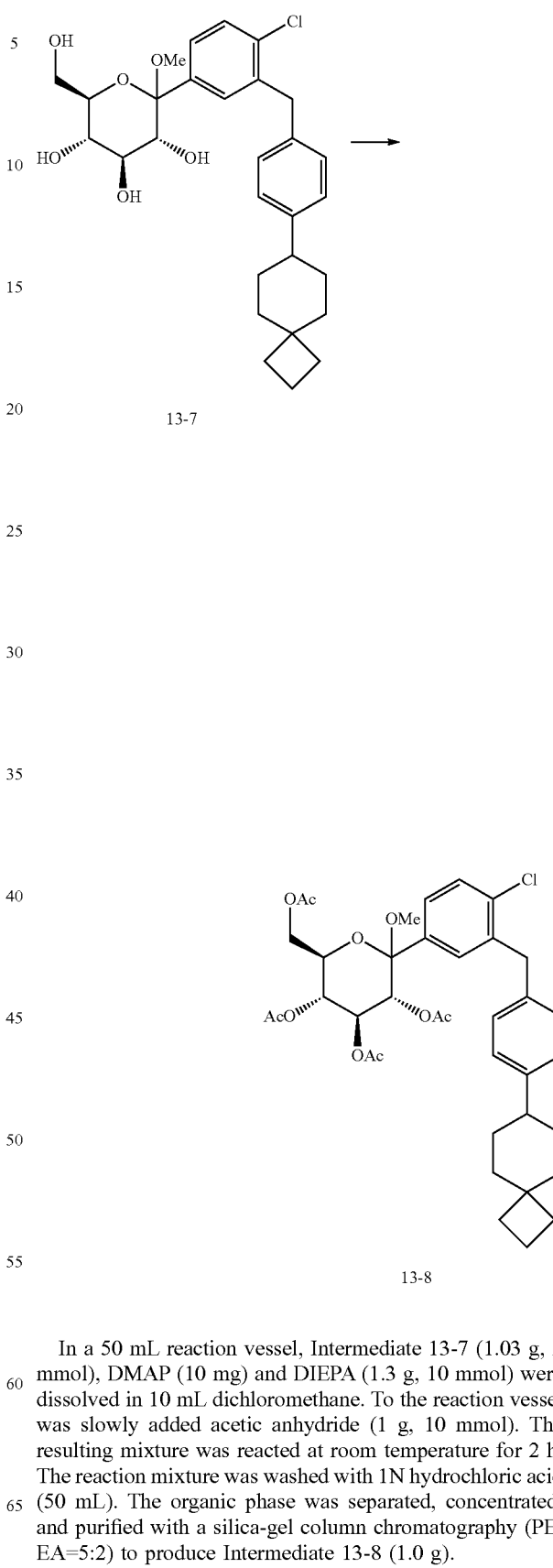

In a 50 mL reaction vessel, Intermediate 13-7 (1.03 g, 2 mmol), DMAP (10 mg) and DIEPA (1.3 g, 10 mmol) were dissolved in 10 mL dichloromethane. To the reaction vessel was slowly added acetic anhydride (1 g, 10 mmol). The resulting mixture was reacted at room temperature for 2 h. The reaction mixture was washed with 1N hydrochloric acid (50 mL). The organic phase was separated, concentrated, and purified with a silica-gel column chromatography (PE/EA=5:2) to produce Intermediate 13-8 (1.0 g).

Step 9 Preparation of Intermediate 13-9

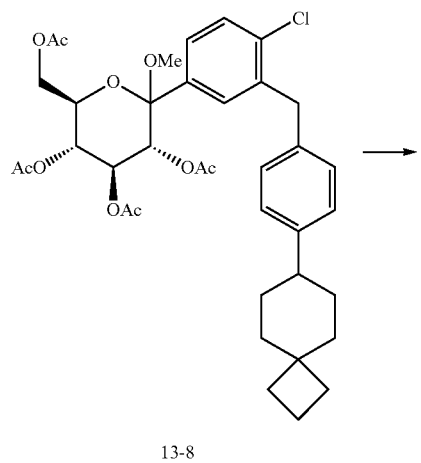

13-8

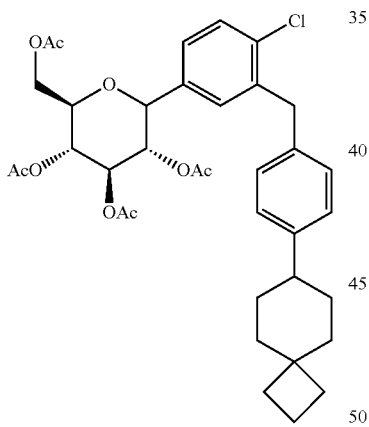

13-9

In a 100 mL reaction vessel, Intermediate 13-8 (1.0 g, 1.5 mmol) was dissolved in 10 mL acetonitrile. To the reaction vessel was added triethylsilane (0.46 g, 4 mmol), and the resulting mixture was cooled to 0° C., to which was added dropwise 1.2 mL boron trifluoride-diethyl etherate. The reaction mixture was stirred at room temperature for 16 h, and poured into 50 mL of a saturated aqueous sodium bicarbonate solution. The resulting mixture was extracted with ethyl acetate (100 mL×3). The organic phases were combined, washed with a saturated NaCl solution, dried over anhydrous sodium sulfate, concentrated and purified with a silica-gel column chromatography (PE/EA=5:2) to produce Intermediate 13-9 (0.91 g) as an oil.

Step 10 Preparation of Compound 13

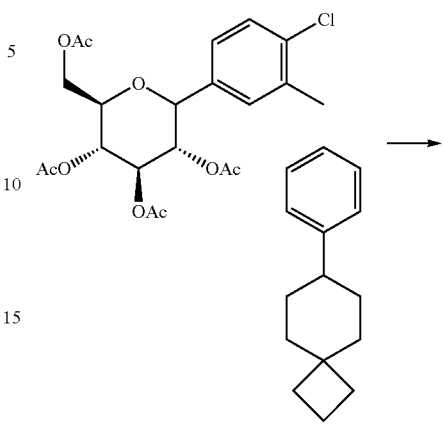

13-9

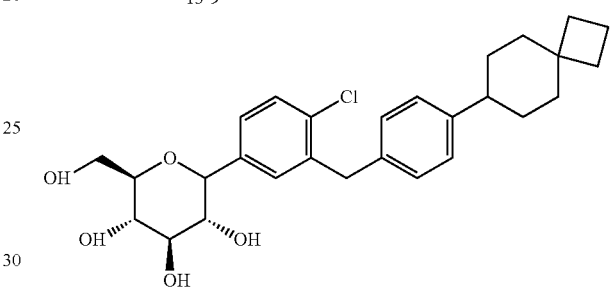

Compound 13

In a 50 mL reaction vessel, Intermediate 13-9 (0.8 g, 1.2 mmol) and lithium hydroxide monohydrate (having a content of 75%) (0.26 g, 6 mmol) were dissolved in a mixed solvent of 10 mL methanol, 10 mL water and 5 mL tetrahydrofuran. The resulting mixture was stirred at room temperature overnight. The reaction mixture was concentrated, separated with a reversed phase chromatography column, and freezing-dried to produce 67 mg of Compound 13.

Formula: $C_{28}H_{35}ClO_5$; Mw: 487; MS(m/z): 486.2/485.2 $(M)^+$.

$^1$H-NMR: (MeOD, 400 MHz) δ: 7.35-7.07 (m, 7H), 4.10-4.00 (m, 3H), 3.86 (m, 1H), 3.69 (m, 1H), 3.47-3.38 (m, 4H), 2.36 (m, 1H), 2.01-1.17 (m, 14H).

Example 14

Preparation of Compound 14

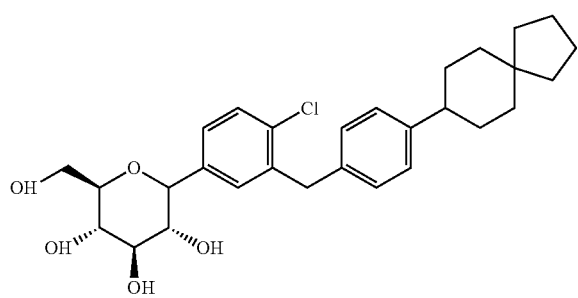 [SMILES: OC[C@H]1OC(c2ccc(Cl)c(Cc3ccc(C4CCC5(CCCC5)CC4)cc3)c2)[C@H](O)[C@@H](O)[C@@H]1O]

Formula: $C_{29}H_{37}ClO_5$; Mw: 501; MS(m/z): 500.2/499.2 $(M)^+$.

Example 15

Preparation of Compound 15

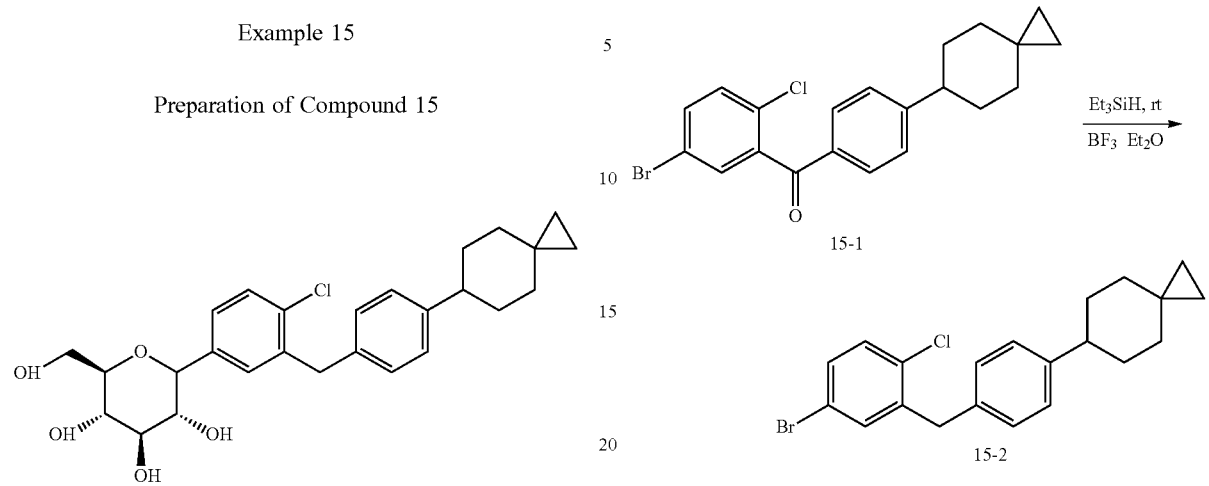

Step 1 Preparation of Intermediate 15-1

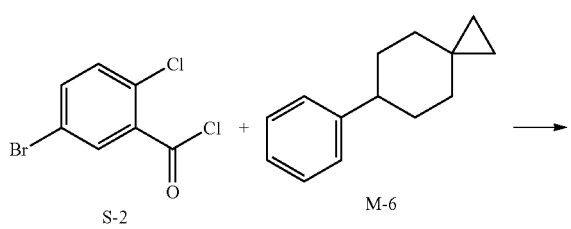

A solution of aluminum trichloride (10.4 g, 77.8 mmol) in dichloromethane (100 mL) was cooled to 0° C., to which was slowly added Intermediate M-6 (5.8 g, 31 mmol) (Intermediate M-6, prepared with reference to Example 13 step 1-3). The resulting mixture was stirred for 20 mins while the temperature was maintained at 0° C. Then to the mixture was slowly added dropwise a solution of 2-chloro-5-bromo-benzoyl chloride (Intermediate S-2) (15.8 g, 62.3 mmol) in dichloromethane (100 mL). The reaction was monitored until the reaction completed. The reaction mixture was poured into ice-water (150 mL), and extracted with dichloromethane (3×100 mL). The organic phases were combined and washed respectively with a dilute hydrochloric acid (1N), water, NaOH (1N), and a saturated NaCl solution, and dried over anhydrous $Na_2SO_4$. The resulting organic phase was evaporated by rotation and purified by a column chromatography (n-hexane/ethyl acetate=1/20) to produce 8.65 g of the target compound, Intermediate 15-1.

Step 2 Preparation of Intermediate 15-2

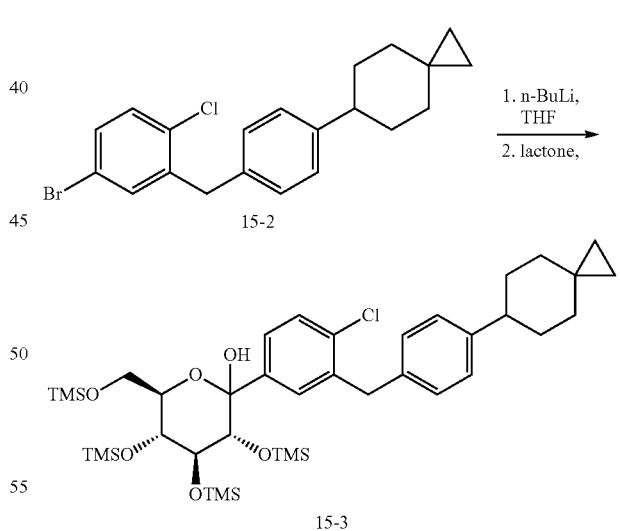

Intermediate 15-1 (8.5 g, 21.4 mmol) was dissolved in acetonitrile (30 mL) and dichloromethane (15 mL). Under an ice bath, to the resulting mixture were added triethylsilane (10.3 mL) and boron trifluoride-diethyl etherate (6.2 mL). The reaction mixture was kept at room temperature overnight. On the second day, the reaction mixture was heated and reacted at 50° C. for 3 h. The mixture was adjusted with a saturated aqueous sodium carbonate solution to pH=8, and extracted with ethyl acetate to produce an organic phase. The organic phase was washed with a saturated NaCl solution, and dried in vacuum to produce 5.6 g of a crude product of Intermediate 15-2.

Step 3 Preparation of Intermediate 15-3

Intermediate 15-2 (3.5 g, 9 mmol) was dissolved in anhydrous THF (50 mL). The resulting mixture was cooled to −78° C. Then to the mixture was slowly added dropwise n-BuLi (2.5M, 4.7 mL, 11.7 mmol) in a nitrogen protection. The stirring was maintained for 2 h. Then to the mixture was slowly added dropwise a solution of (3R,4 S,5R,6R)-3,4,5-tris(trimethylsilyloxy)-6-((trimethylsilyloxy)methyl)tetrahydro-2H-pyran-2-one in tetrahydrofuran (6.3 g, 13.5 mmol) at −78° C. The stirring was maintained for 2 h. Then the reaction mixture was quenched with an aqueous saturated ammonium chloride solution (50 mL). The aqueous layer was extracted with ethyl acetate (3×50 mL). The combined organic phase was washed with water and a saturated NaCl solution, and evaporated by rotation to produce 5.8 g of Intermediate 15-3 as oil.

Step 4 Preparation of Intermediate 15-4

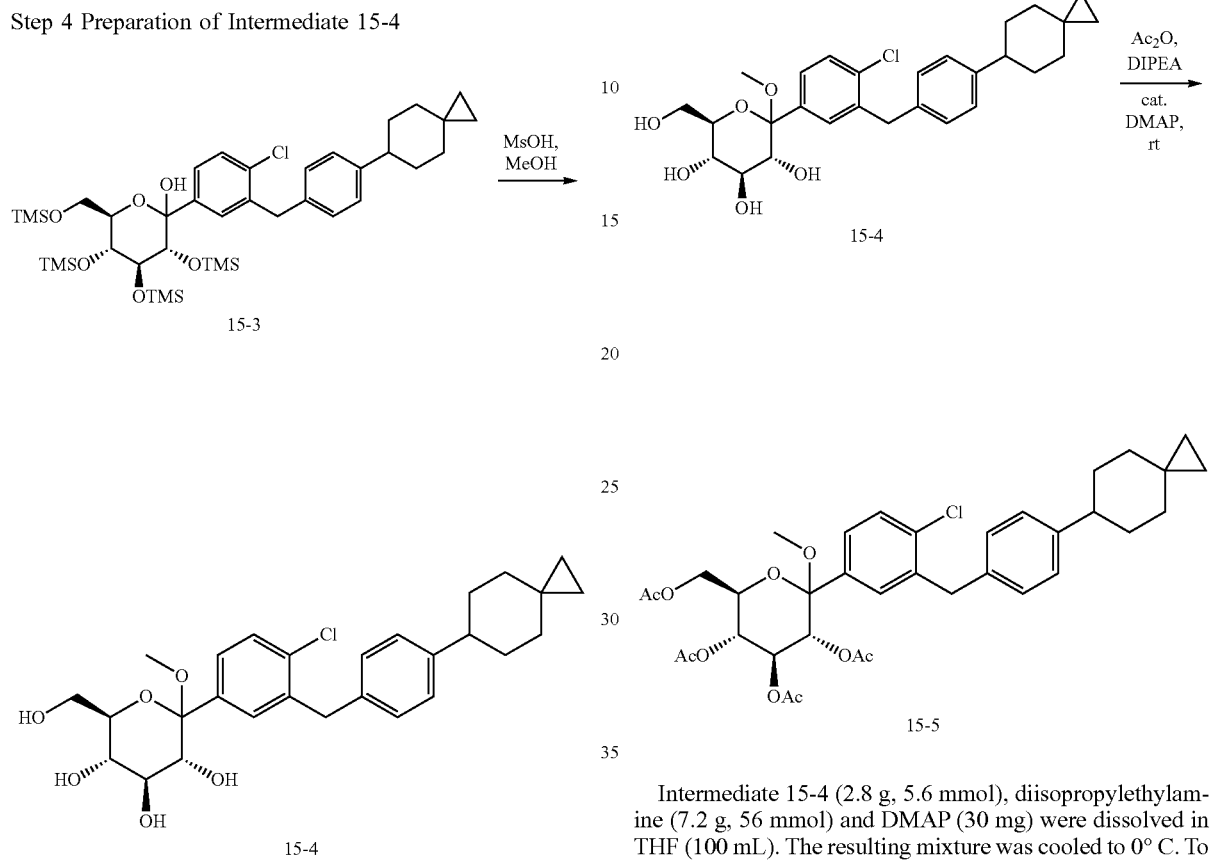

Intermediate 15-3 (5.6 g, 7.2 mmol) was dissolved in absolute anhydrous methanol (50 mL). The resulting mixture was cooled to 0° C., to which was added a solution of methanesulfonic acid (4 mL) in anhydrous methanol (10 mL). The resulting mixture was slowly warmed up to room temperature and stirred for 12 h. The mixture was adjusted with an aqueous saturated NaHCO$_3$ solution to pH=8, and extracted with ethyl acetate. The combined organic phase was washed with water and a saturated NaCl solution, dried, and evaporated by rotation to produce 2.8 g of Intermediate 15-4.

Step 5 Preparation of Intermediate 15-5

Intermediate 15-4 (2.8 g, 5.6 mmol), diisopropylethylamine (7.2 g, 56 mmol) and DMAP (30 mg) were dissolved in THF (100 mL). The resulting mixture was cooled to 0° C. To the mixture was slowly added acetic anhydride (5.68 g, 56 mmol). The resulting mixture was stirred for 2 h. The reaction mixture was adjusted with a saturated aqueous sodium bicarbonate solution to pH=8, and extracted with ethyl acetate (3×100 mL). The combined organic phase was washed with water (100 mL) and a saturated NaCl solution (100 mL), dried, concentrated by rotary evaporation, and purified by a column chromatography to produce 2.6 g of Intermediate 15-5.

Step 6 Preparation of Intermediate 15-6

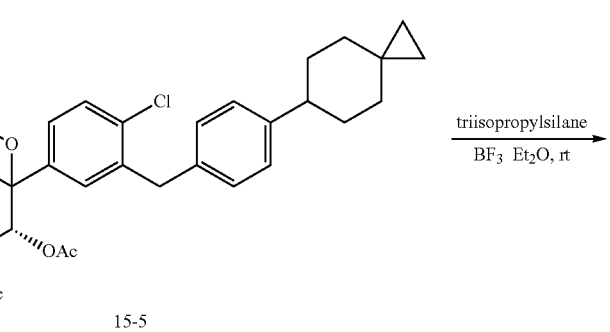

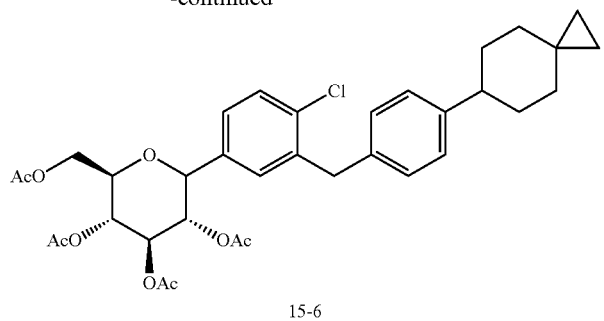

15-6

A solution of Intermediate 15-5 (1.1 g, 1.64 mmol) in acetonitrile (50 mL) was cooled to 10° C., to which were added triisopropylsilane (0.78 g, 4.9 mmol) and boron trifluoride-diethyl etherate (0.93 g, 6.5 mmol). The reaction was monitored until the reaction completed. The reaction mixture was quenched with a saturated sodium bicarbonate solution, and extracted with ethyl acetate (3×100 mL). The combined organic phase was washed with water and a saturated NaCl solution, dried, concentrated by rotary evaporation, purified with a column chromatography (petroleum ether/ethyl acetate=1/5, V/V) to produce 0.7 g of Intermediate 15-6.

Step 7 Preparation of Compound 15

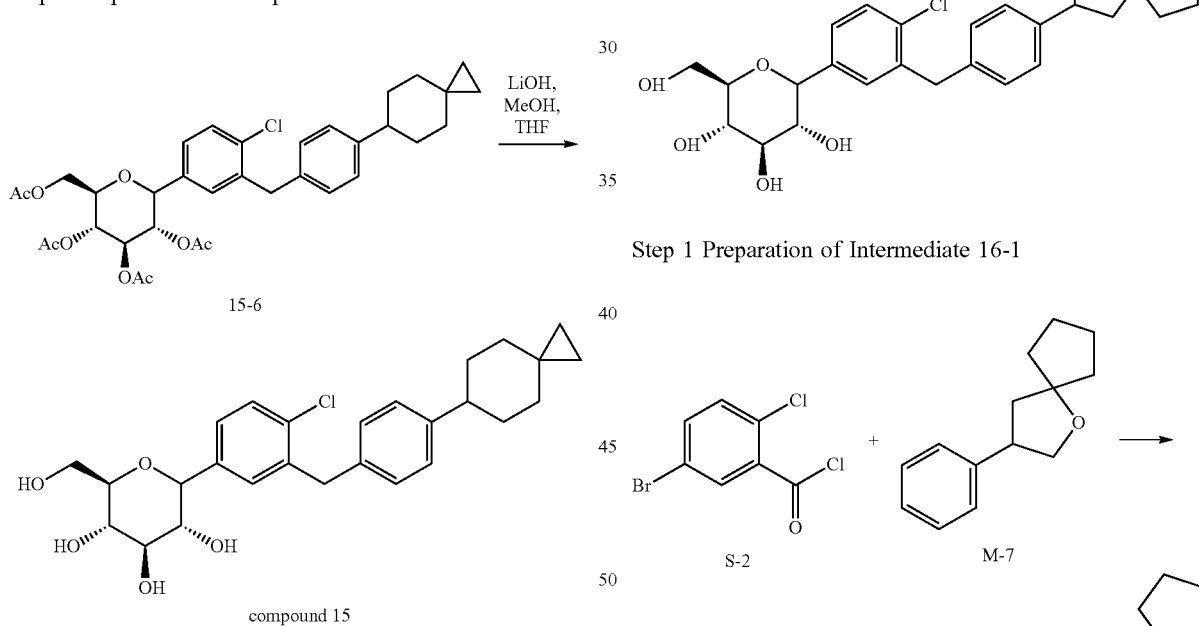

Intermediate 15-6 (0.3 g, 0.46 mmol) was dissolved in a mixed solution of tetrahydrofuran (5 mL) and methanol (5 mL). To the resulting mixture was added an aqueous lithium hydroxide monohydrate solution (1N, 1 mL) at 0° C. The reaction mixture was warmed up slowly to room temperature, and stirred for 3 h. The reaction was monitored until the reaction completed. The reaction mixture was concentrated, and extracted with dichloromethane. The combined organic phase was washed with water and a saturated NaCl solution, dried, and concentrated to produce 0.088 g of Compound 15. Formula: $C_{27}H_{33}ClO_5$; Mw: 473; MS(m/z): 472.2/471.2 $(M)^+$.

$^1$H-NMR: (MeOD, 400 MHz) δ: 7.53 (d, 1H), 7.40 (d, 1H), 7.36 (d, 2H), 7.03-6.98 (m, 3H), 4.07-3.90 (m, 2H), 3.80-3.72 (m, 2H), 3.49-3.35 (m, 1H), 3.32-3.31 (m, 1H), 3.14-3.06 (m, 3H), 2.19 (m, 1H), 1.85-1.78 (m, 2H), 1.67-1.64 (m, 3H), 1.38-1.29 (m, 3H), 1.09-0.90 (m, 4H).

Example 16

Preparation of Compound 16

Step 1 Preparation of Intermediate 16-1

A solution of aluminum trichloride (2.8 g, 21 mmol) in dichloromethane (25 mL) was cooled to 0° C., to which was slowly added 3-phenyl-1-oxaspiro[4.4]nonane (4.30 g, 21.3 mmol) (Intermediate M-7, prepared with reference to Example 13, step 1-3). The mixture was stirred for 1 h while keeping it at 0° C. Then to the mixture was slowly added dropwise a solution of 2-chloro-5-bromo-benzoyl chloride (4.56 g, 21.3 mmol) in dichloromethane (15 mL). The reaction was monitored until the reaction completed. The reaction mixture was poured into ice-water (150 mL), and extracted with dichloromethane (3×100 mL). The organic phases were combined and washed respectively with a dilute hydrochloric acid (1N), water, NaOH (1N), and a saturated NaCl solution, and dried over anhydrous Na$_2$SO$_4$. The resulting organic phase was evaporated by rotation and purified by a column chromatography (n-hexane/ethyl acetate=1/20) to produce 6.78 g of the target compound, Intermediate 16-1.

Step 2 Preparation of Intermediate 16-2

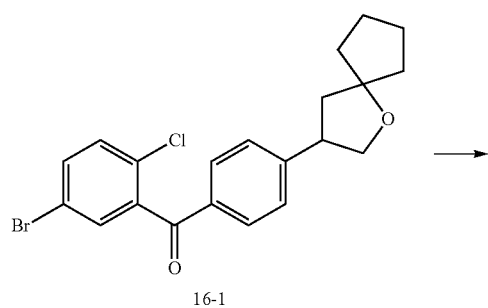

16-1

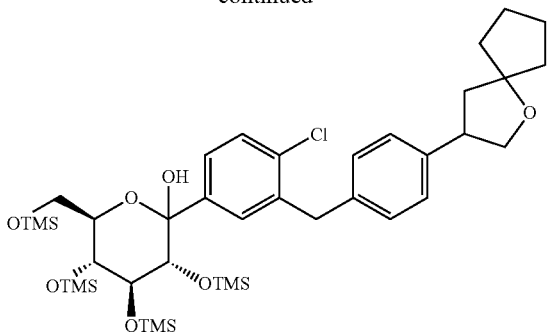

16-3

Intermediate 16-2 (18.6 g, 46 mmol) was dissolved in an anhydrous THF (150 mL). The resulting mixture was cooled to −78° C. Then to the mixture was slowly added dropwise n-BuLi (2.5M, 18.4 mL, 46 mmol) in a nitrogen protection. The resulting mixture was stirred for 3 h. Then to the mixture was slowly added dropwise a solution of (3R,4S, 5R,6R)-3,4,5-tris(trimethylsilyloxy)-6-((trimethylsilyloxy) methyl)tetrahydro-2H-pyran-2-one in n-hexane (300 mL) at −78° C., while the stirring was kept for 0.5 h. Then the reaction mixture was quenched with an aqueous saturated ammonium chloride solution (100 mL). The resulting aqueous layer was extracted with ethyl acetate (3×100 mL). The combined organic phase was washed with water and a saturated NaCl solution, and evaporated by rotation to produce 17.2 g of Intermediate 16-3 as oil.

Step 4 Preparation of Intermediate 16-4

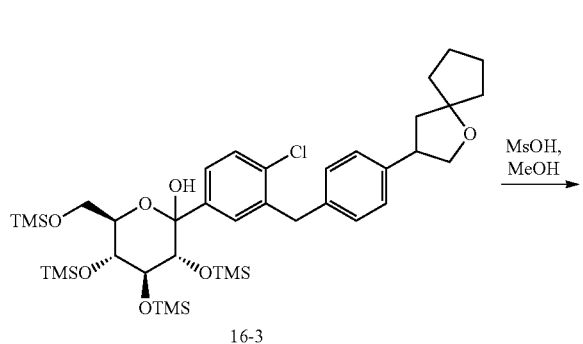

16-3

Intermediate 16-1(16.68 g, 39.9 mmol) was dissolved in trifluoroacetic acid (30 mL). Then to the resulting mixture was added triethylsilane (7.86 g, 67.6 mmol). The reaction mixture was heated to reflux for 16 h, adjusted with a saturated aqueous sodium carbonate solution to pH=8, and extracted with ethyl acetate to produce an organic phase. The organic phase was washed with a saturated NaCl solution, and dried in vacuum to produce 10.5 g of a crude product of Intermediate 16-2.

Step 3 Preparation of Intermediate 16-3

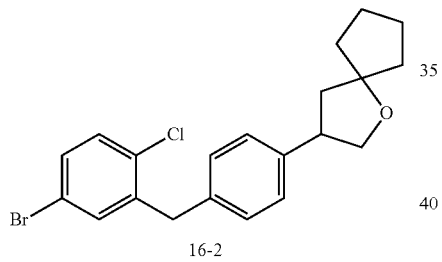

16-2

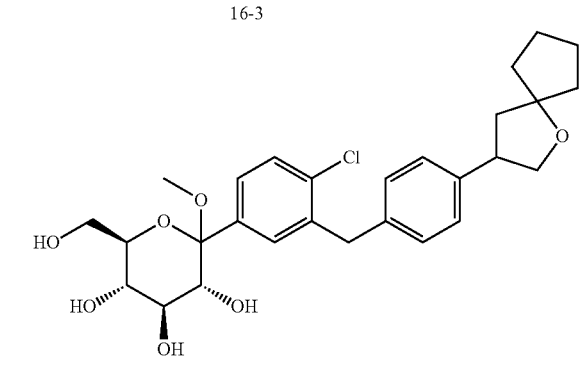

16-4

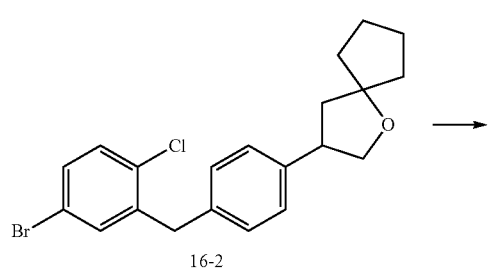

16-2

Intermediate 16-3 (4.90 g, 10.0 mmol) was dissolved in absolute anhydrous methanol (10 mL). The resulting mixture was cooled to 0° C., to which was added a solution of methanesulfonic acid (0.4 mL) in anhydrous methanol (10 mL). The resulting mixture was slowly warmed up to room temperature and stirred for 16 h, adjusted with an aqueous saturated NaHCO$_3$ solution to pH=8, and extracted with ethyl acetate. The combined organic phase was washed with water and a saturated NaCl solution, dried, and evaporated by rotation to produce 5.18 g of Intermediate 16-4.

Step 5 Preparation of Intermediate 16-5

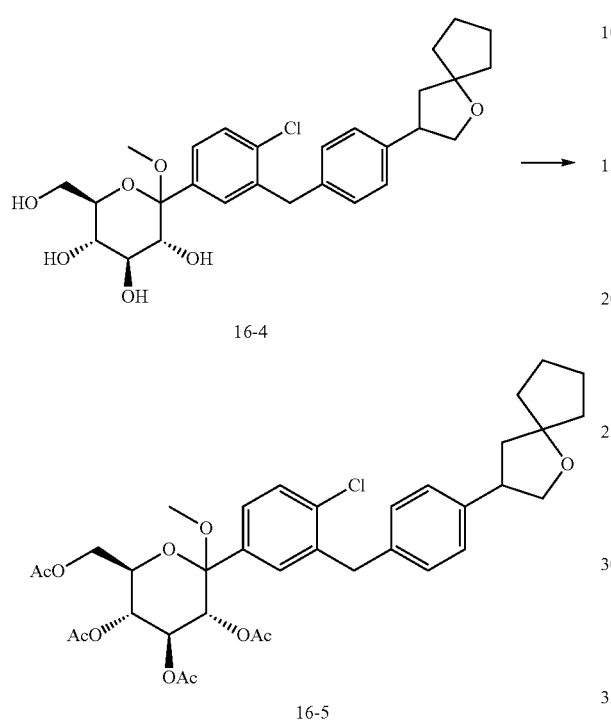

16-4

16-5

Intermediate 16-4 (4.71 g, 9.1 mmol), diisopropylethylamine (9.4 g, 72.8 mmol) and DMAP (10 mg) were dissolved in THF (100 mL). The resulting mixture was cooled to 0° C. To the mixture was slowly added acetic anhydride (7.43 g, 72.8 mmol). The resulting mixture was stirred for 0.5 h. The reaction mixture was adjusted with a saturated aqueous sodium bicarbonate solution to pH=8, and extracted with ethyl acetate (3×60 mL). The combined organic phase was washed with water (70 mL) and a saturated NaCl solution (70 mL), dried, concentrated by rotary evaporation, and purified by a column chromatography to produce 3.93 g of Intermediate 16-5.

Step 6 Preparation of Intermediate 16-6

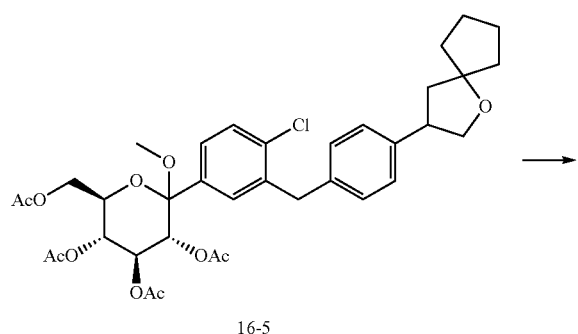

16-5

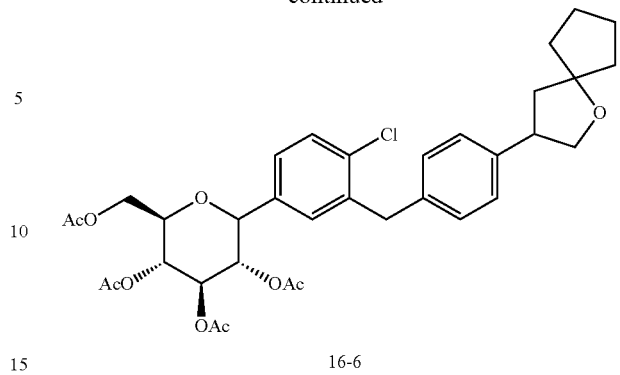

16-6

A solution of Intermediate 16-5 (10.98 g, 16.0 mmol) in acetonitrile (50 mL) was cooled to 10° C., to which was added triisopropylsilane (5.1 g, 32 mmol) and boron trifluoride-diethyl etherate (6.8 g, 48 mmol). The reaction was monitored until the reaction completed. The reaction mixture was quenched with a saturated sodium bicarbonate solution, and extracted with ethyl acetate (3×100 mL).

The combined organic phase was washed with water and a saturated NaCl solution, dried, concentrated by rotary evaporation, and recrystallized (n-hexane/ethyl acetate=1/15, V/V) to produce 7.56 g of Intermediate 16-6.

Step 7 Preparation of Intermediate 16-7

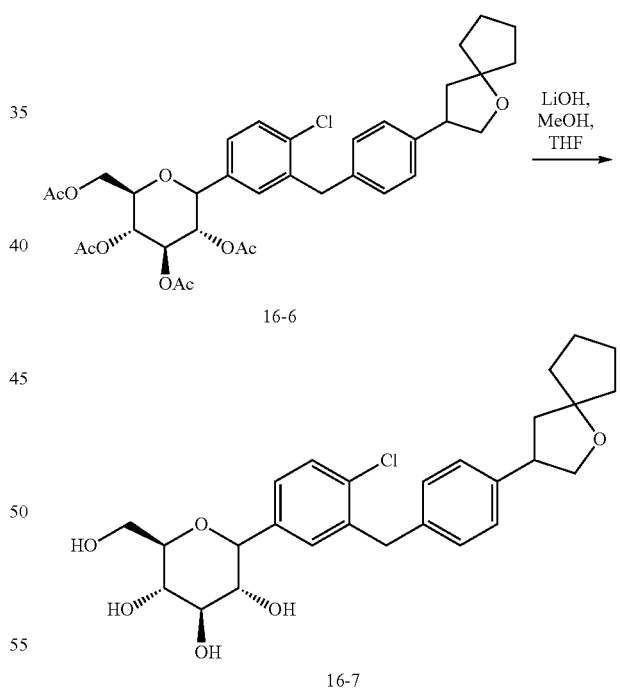

16-6

16-7

Intermediate 16-6 (9.77 g, 14.9 mmol) was dissolved in a mixed solution of tetrahydrofuran (100 mL) and methanol (100 mL). To the resulting mixture was added a solution of lithium hydroxide monohydrate (4.4 g, 104 mmol) in water (50 mL) at 0° C. The reaction mixture was warmed up slowly to room temperature, and stirred for 14 h. The reaction was monitored until the reaction completed. The reaction mixture was concentrated, and extracted with dichloromethane. The combined organic phase was washed with water and a saturated NaCl solution, dried, and concentrated to produce 6.47 g of Intermediate 16-7.

Formula: $C_{27}H_{33}ClO_6$; Mw: 488.5; LC-MS(M+H)$^+$: 489.

Example 17

Preparation of Compound 17

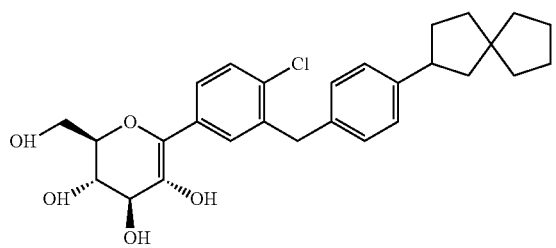

6.46 g of Compound 17 was prepared with reference of Example 14.

Formula: $C_{28}H_{35}ClO_5$; Mw: 487; LC-MS (M+H)$^+$: 487.

Example 18

Preparation of Compound 18

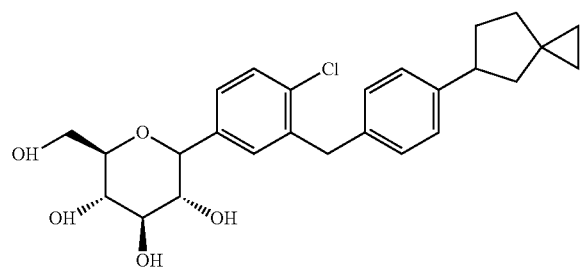 [SMILES: OC[C@H]1OC(c2ccc(Cl)c(Cc3ccc(C4CCC5(CC5)C4)cc3)c2)[C@H](O)[C@@H](O)[C@@H]1O]

Step 1 Preparation of Intermediate 18-1

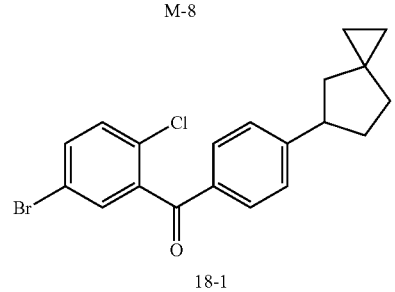

A solution of aluminum trichloride (10.4 g, 77.8 mmol) in dichloromethane (100 mL) was cooled to 0° C., to which was slowly added Intermediate M-8 (5.38 g, 31 mmol) (prepared with reference to Example 13, step 1-3). The resulting mixture was kept at 0° C. while the mixture was stirred for 20 mins. Then to the mixture was slowly added dropwise a solution of 2-chloro-5-bromo-benzoyl chloride (11.8 g, 46.8 mmol) in dichloromethane (100 mL). The reaction was monitored until the reaction completed. The reaction mixture was poured into ice-water (150 mL), and extracted with dichloromethane (3×100 mL). The organic phases were combined and washed respectively with a dilute hydrochloric acid (1N), water, NaOH (1N), and a saturated NaCl solution, and dried over anhydrous $Na_2SO_4$. The resulting organic phase was evaporated by rotation and purified by a column chromatography (n-hexane/ethyl acetate=1/30) to produce 6.25 g of the target compound, Intermediate 18-1.

Step 2 Preparation of Intermediate 18-2

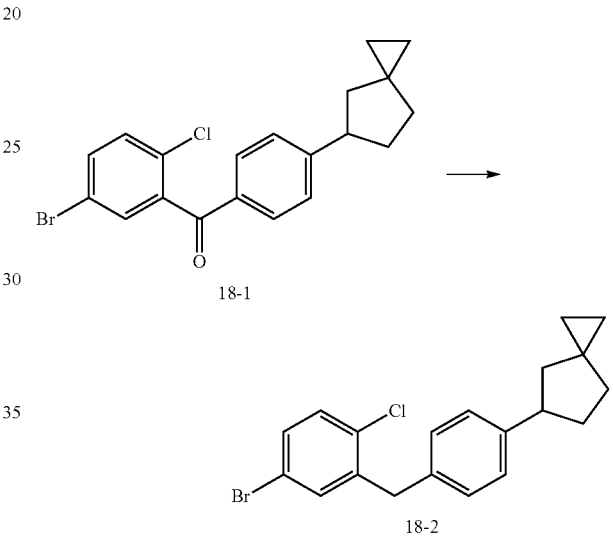

Intermediate 18-1 (5.69 g, 14.7 mmol) was dissolved in a mixed solution of acetonitrile (30 mL) and dichloromethane (15 mL). Under an ice bath, to the resulting mixture were added triethylsilane (5.12 g, 43 mmol) and boron trifluoride-diethyl etherate (4.2 g, 30 mmol). The resulting mixture was kept at room temperature overnight. On the next day, the reaction mixture was heated to 50° C. and reacted for 3 h, adjusted with a saturated aqueous sodium carbonate solution to pH=8, and extracted with ethyl acetate to produce an organic phase. The organic phase was washed with a saturated NaCl solution, and dried in vacuum to produce 3.8 g of a crude product of Intermediate 18-2.

Step 3 Preparation of Intermediate 18-3

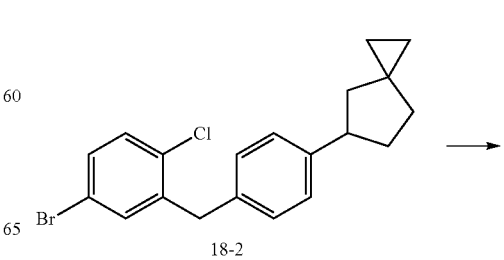

-continued

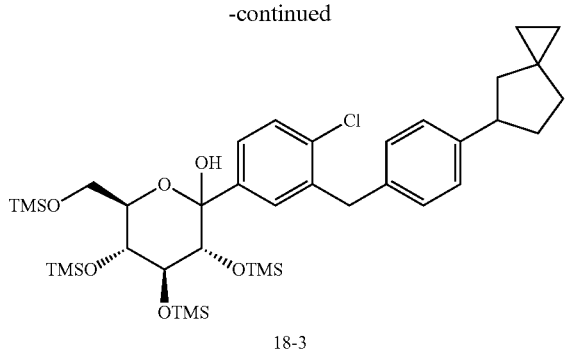

18-3

Intermediate 18-2 (1.5 g, 3.9 mmol) was dissolved in anhydrous tetrahydrofuran (30 mL). The resulting mixture was cooled to −78° C. Then to the mixture was slowly added dropwise n-BuLi (2.5M, 5.2 mmol) in a nitrogen protection. After the stirring was kept for 2 h, to the resulting mixture was slowly added dropwise a solution of (3R,4S,5R,6R)-3,4,5-tris(trimethylsilyloxy)-6-((trimethylsilyloxy)methyl)tetrahydro-2H-pyran-2-one in tetrahydrofuran (2.8 g, 5.9 mmol) at −78° C. The stirring was kept at −78° C. for 2 h. Then the reaction mixture was quenched with an aqueous saturated ammonium chloride solution (30 mL). The aqueous layer was extracted with ethyl acetate (3×50 mL). The combined organic phase was washed with water and a saturated NaCl solution, and evaporated by rotation to produce 2.51 g of Intermediate 18-3 as oil.

Step 4 Preparation of Intermediate 18-4

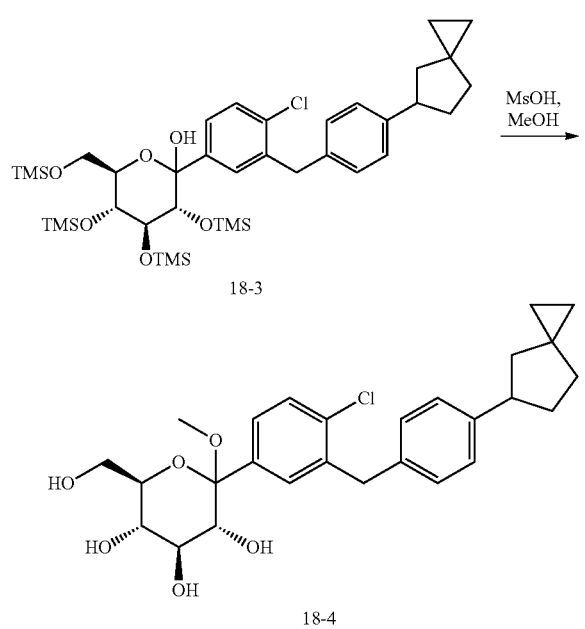

Intermediate 18-3 (4.16 g, 5.45 mmol) was dissolved in absolute anhydrous methanol (10 mL). The resulting mixture was cooled to 0° C., to which was added a solution of methanesulfonic acid (1.5 mL) in anhydrous methanol (10 mL). The resulting mixture was slowly warmed up to room temperature and stirred for 12 h. The mixture was adjusted with an aqueous saturated NaHCO₃ solution to pH=8, and extracted with ethyl acetate. The combined organic phase was washed with water and a saturated NaCl solution, dried, and evaporated by rotation to produce 2.1 g of Intermediate 18-4.

Step 5 Preparation of Intermediate 18-5

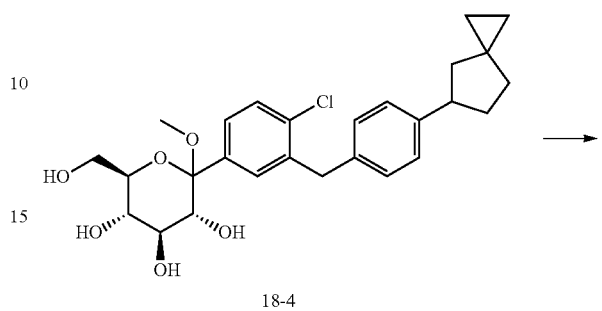

18-4

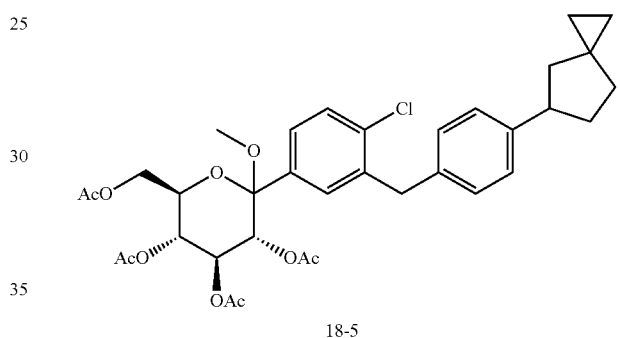

18-5

Intermediate 18-4 (2.1 g, 4.3 mmol), diisopropylethylamine (5.56 g, 43 mmol) and DMAP (30 mg) were dissolved in tetrahydrofuran (30 mL). The resulting mixture was cooled to 0° C. To the mixture was slowly added acetic anhydride (4.38 g, 43 mmol). The reaction mixture was stirred for 2 h, adjusted with a saturated aqueous sodium bicarbonate solution to pH=8, and extracted with ethyl acetate (3×30 mL). The combined organic phase was washed with water (30 mL) and a saturated NaCl solution (30 mL), dried, concentrated by rotary evaporation, and purified by a column chromatography to produce 1.73 g of Intermediate 18-5.

Step 6 Preparation of Intermediate 18-6

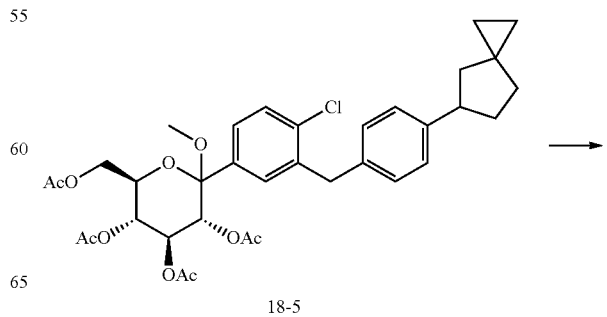

18-5

-continued

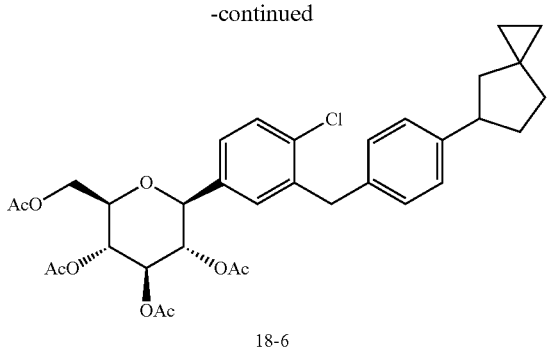

18-6

A solution of Intermediate 18-5 (1.73 g, 2.64 mmol) in acetonitrile (50 mL) was cooled to 10° C., to which were added triethylsilane(1.26 g, 7.9 mmol) and boron trifluoride-diethyl etherate (1.49 g, 10.5 mmol). The reaction was monitored until the reaction completed. The reaction mixture was quenched with a saturated sodium bicarbonate solution, and extracted with ethyl acetate (3×50 mL). The combined organic phase was washed with water and a saturated NaCl solution, dried, concentrated by rotary evaporation, and purified with a column chromatography (petroleum ether/ethyl acetate=1/5) to produce 0.8 g of the target compound, Intermediate 18-6.

Step 7 Preparation of Compound 18

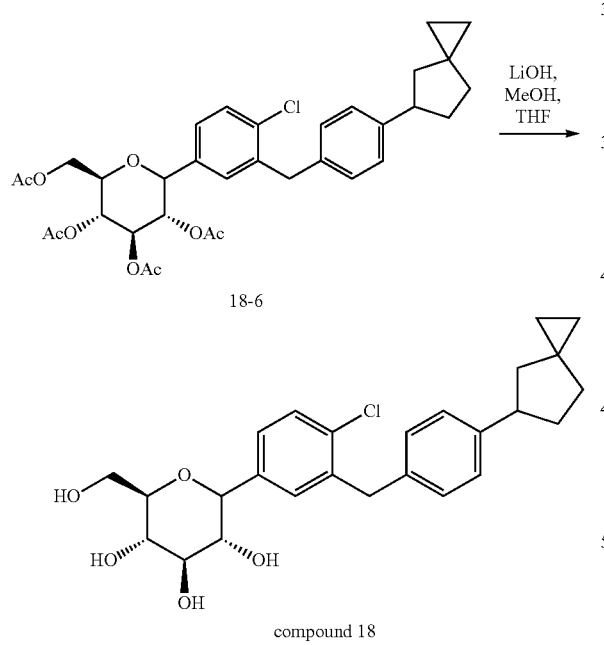

Intermediate 18-6 (0.8 g, 1.28 mmol) was dissolved in a mixed solution of tetrahydrofuran (8 mL) and methanol (15 mL). To the resulting mixture was added an aqueous lithium hydroxide monohydrate solution (1N, 8 mL) at 0° C. The reaction mixture was warmed up slowly to room temperature, and stirred for 3 h. The reaction was monitored until the reaction completed. The reaction mixture was concentrated, and extracted with dichloromethane. The combined organic phase was washed with water and a saturated NaCl solution, dried, and concentrated to produce 0.088 g of Compound 18. Formula: $C_{26}H_{31}ClO_5$; Mw: 459; MS(m/z): 476.3 $(M+NH_4^+)^+$.

$^1$H-NMR: (MeOD, 400 MHz) δ: 7.35 (d, 2H), 7.31 (d, 1H), 7.09 (d, 1H, 7.03-6.98 (m, 3H), 4.10-4.07 (m, 3H), 3.88-3.85 (m, 2H), 3.69-3.68 (m, 1H), 3.48-3.38 (m, 3H), 2.92-2.88 (d, 1H), 1.85-1.81 (m, 2H), 1.64-1.58 (m, 2H), 1.44-1.41 (m, 4H), 1.38-1.29 (m, 2H).

Example 19

Preparation of Compound 19

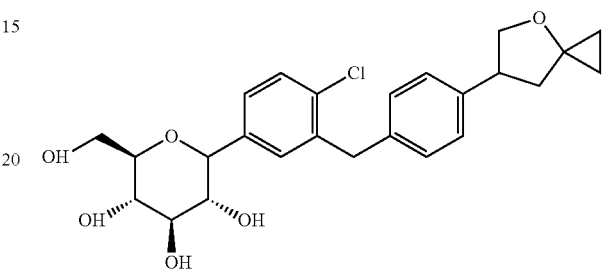

Compound 19 (6.47 g) was prepared with reference of Example 16.

Formula: $C_{25}H_{29}ClO_6$; Mw: 460.5; LC-MS (M+H)$^+$: 461.

Meanwhile, the racemic compounds 1-2 and the compounds 4-19 as prepared above were resolved with a preparative HPLC by gradient elution (C-18 column, eluent: 5%-95% methanol/water) to produce the following compounds:

| No. | Chemical Structure |
|---|---|
| 20 | 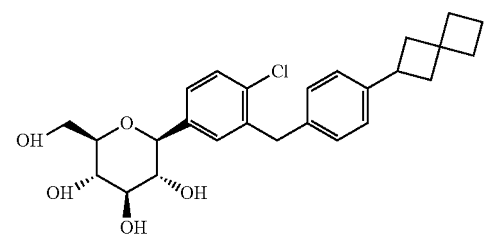 [SMILES: OC[C@H]1O[C@@H](c2ccc(Cl)c(Cc3ccc(C4CC5(CCC5)C4)cc3)c2)[C@H](O)[C@@H](O)[C@@H]1O] |
| 21 | 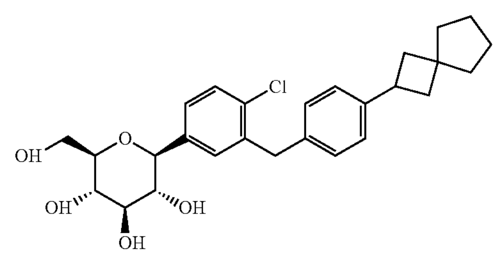 [SMILES: OC[C@H]1O[C@@H](c2ccc(Cl)c(Cc3ccc(C4CC5(CCCC5)C4)cc3)c2)[C@H](O)[C@@H](O)[C@@H]1O] |
| 22 | 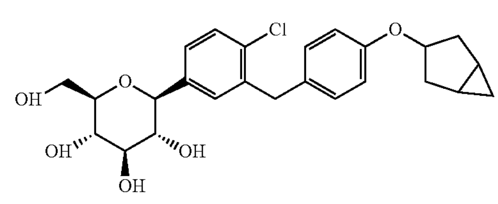 [SMILES: OC[C@H]1O[C@@H](c2ccc(Cl)c(Cc3ccc(OC4CC5CC5C4)cc3)c2)[C@H](O)[C@@H](O)[C@@H]1O] |

| No. | Chemical Structure |
|---|---|
| 23 | 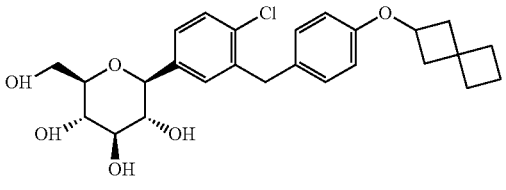 [SMILES: OC[C@H]1O[C@@H](c2ccc(Cl)c(Cc3ccc(OC4CC5(CCC5)C4)cc3)c2)[C@H](O)[C@@H](O)[C@@H]1O] |
| 24 | 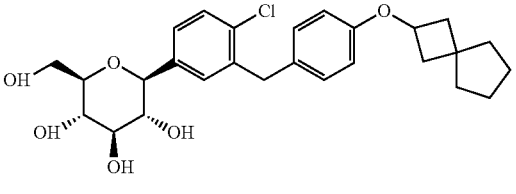 [SMILES: OC[C@H]1O[C@@H](c2ccc(Cl)c(Cc3ccc(OC4CC5(CCCC5)C4)cc3)c2)[C@H](O)[C@@H](O)[C@@H]1O] |
| 25 | 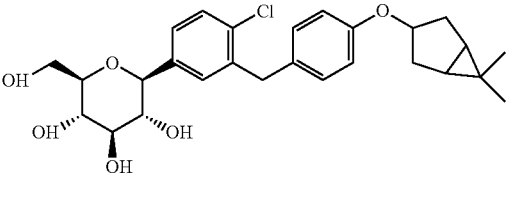 [SMILES: CC1(C)C2CC(Oc3ccc(Cc4cc([C@@H]5O[C@H](CO)[C@@H](O)[C@H](O)[C@H]5O)ccc4Cl)cc3)CC21] |
| 26 | 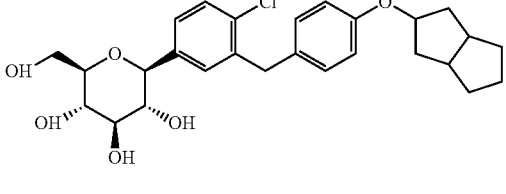 |
| 27 | 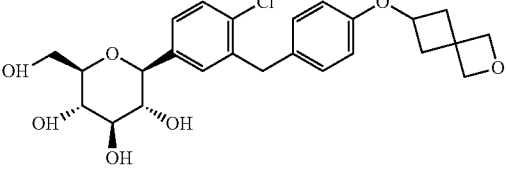 |
| 28 | 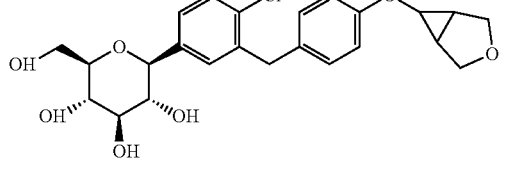 |
| 29 | 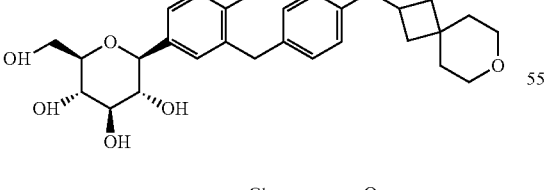 |
| 30 | 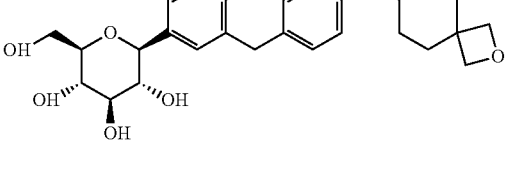 |
| No. | Chemical Structure |
|---|---|
| 31 | 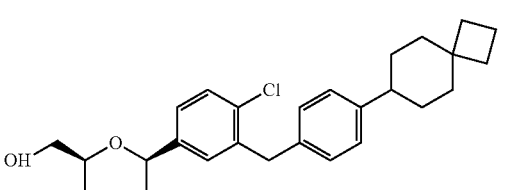 |
| 32 | 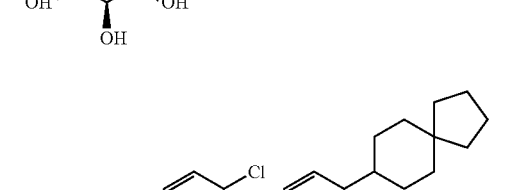 |
| 33 | 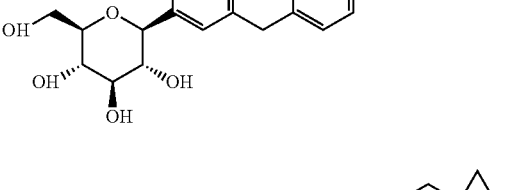 |
| 34 | 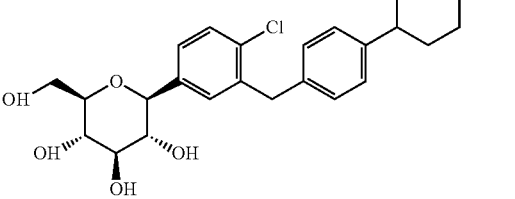 |
| 35 | 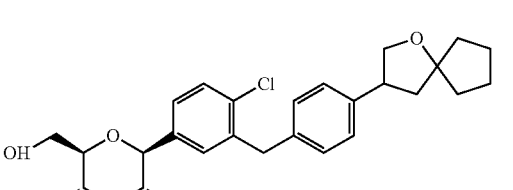 |
| 36 | 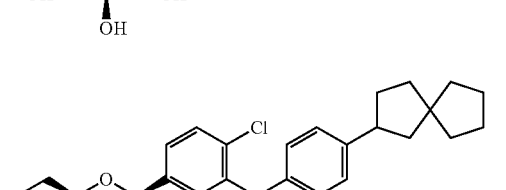 |

| No. | Chemical Structure |
|---|---|
| 37 | 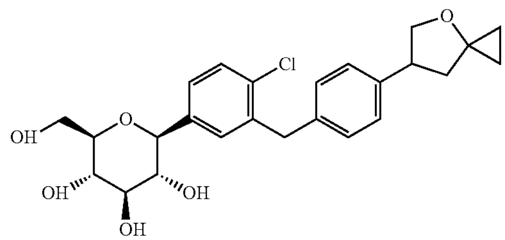 [SMILES: OC[C@H]1O[C@@H](c2ccc(Cl)c(Cc3ccc(C4COC5(CC5)C4)cc3)c2)[C@H](O)[C@@H](O)[C@@H]1O] |
| 38 | 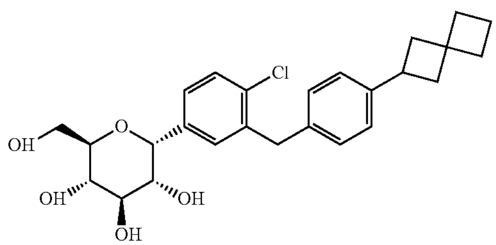 [SMILES: OC[C@H]1O[C@H](c2ccc(Cl)c(Cc3ccc(C4CC5(CCC5)C4)cc3)c2)[C@H](O)[C@@H](O)[C@@H]1O] |
| 39 | 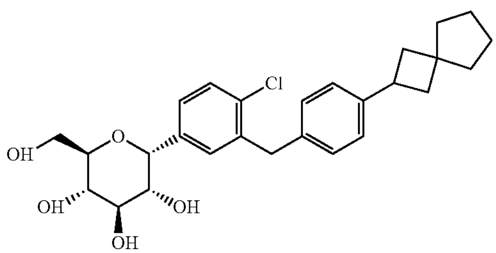 [SMILES: OC[C@H]1O[C@H](c2ccc(Cl)c(Cc3ccc(C4CC5(CCCC5)C4)cc3)c2)[C@H](O)[C@@H](O)[C@@H]1O] |
| 40 | 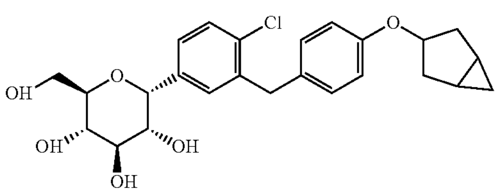 [SMILES: OC[C@H]1O[C@H](c2ccc(Cl)c(Cc3ccc(OC4CC5CC5C4)cc3)c2)[C@H](O)[C@@H](O)[C@@H]1O] |
| 41 | 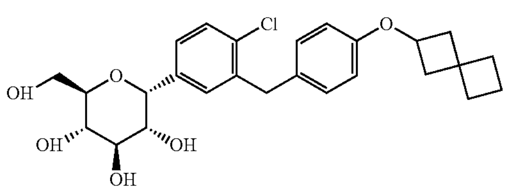 [SMILES: OC[C@H]1O[C@H](c2ccc(Cl)c(Cc3ccc(OC4CC5(CCC5)C4)cc3)c2)[C@H](O)[C@@H](O)[C@@H]1O] |
| 42 | 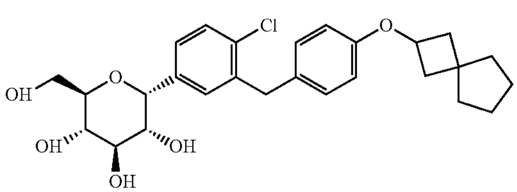 [SMILES: OC[C@H]1O[C@H](c2ccc(Cl)c(Cc3ccc(OC4CC5(CCCC5)C4)cc3)c2)[C@H](O)[C@@H](O)[C@@H]1O] |
| 43 | 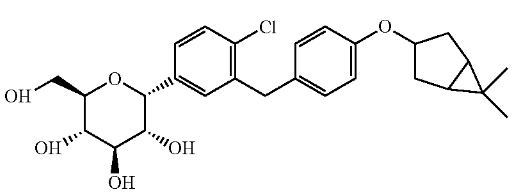 [SMILES: CC1(C)C2CC(Oc3ccc(Cc4cc([C@H]5O[C@H](CO)[C@@H](O)[C@H](O)[C@H]5O)ccc4Cl)cc3)CC21] |
| 44 | |
| 45 | |
| 46 | |
| 47 | |
| 48 | |
| 49 | |
| 50 | |

-continued

| No. | Chemical Structure |
|---|---|
| 51 | 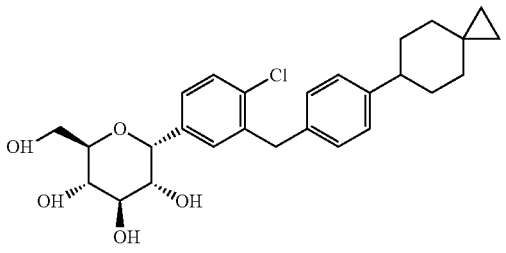 [SMILES: OC[C@H]1O[C@H](c2ccc(Cl)c(Cc3ccc(C4CCC5(CC4)CC5)cc3)c2)[C@H](O)[C@@H](O)[C@@H]1O] |
| 52 | 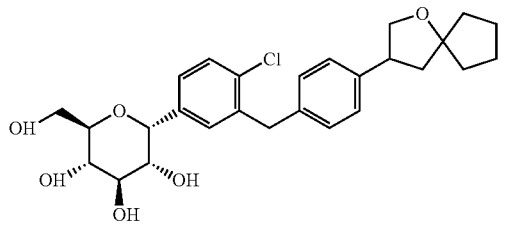 [SMILES: OC[C@H]1O[C@H](c2ccc(Cl)c(Cc3ccc(C4COC5(CCCC5)C4)cc3)c2)[C@H](O)[C@@H](O)[C@@H]1O] |
| 53 | 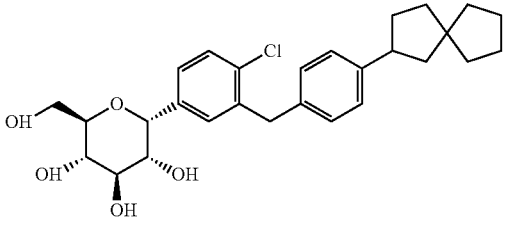 [SMILES: OC[C@H]1O[C@H](c2ccc(Cl)c(Cc3ccc(C4CCC5(CCCC5)C4)cc3)c2)[C@H](O)[C@@H](O)[C@@H]1O] |
| 54 | 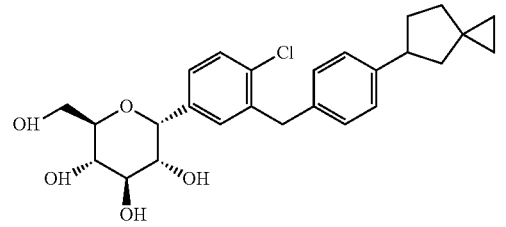 [SMILES: OC[C@H]1O[C@H](c2ccc(Cl)c(Cc3ccc(C4CCC5(CC5)C4)cc3)c2)[C@H](O)[C@@H](O)[C@@H]1O] |
| 55 | 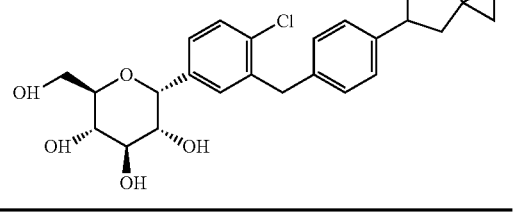 |

The invention claimed is:

1. A compound represented by general formula (I), a pharmaceutically acceptable salt thereof or a stereoisomer thereof:

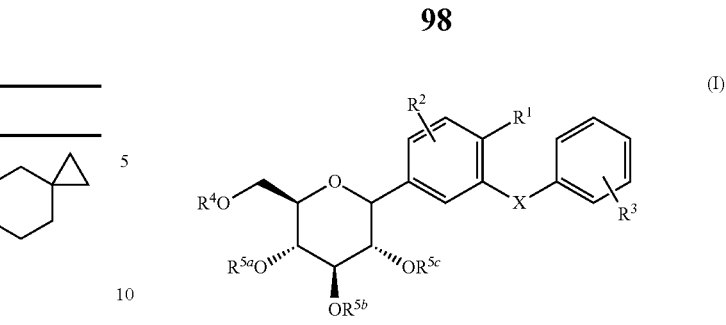

wherein, $R^1$ and $R^2$ each independently represent hydrogen, —OH, —OR$^6$, alkyl, —CF$_3$, —OCHF$_2$, —OCF$_3$, halogen, —CN, C$_{2-6}$alkynyl, C$_{2-6}$alkenyl, cycloalkyl, C$_{2-4}$alkenyl-C$_{1-4}$alkyl, C$_{2-4}$alkynyl-C$_{1-4}$alkyl, C$_{2-4}$alkenyl-C$_{1-4}$ alkoxy, C$_{2-4}$alkynyl-C$_{1-4}$alkoxy, C$_{3-7}$cycloalkyl-C$_{1-4}$alkyl, —NR$^7$R$^{7a}$, carbonyl, —COOR$^{6a}$, —COOH, —COR$^{7b}$, —CH(OH)R$^{7c}$, —CH(OR$^{6g}$)R$^{7d}$, —CONR$^7$R$^{7a}$, —NHCOR$^{6b}$, —NHSO$_2$R$^{6c}$, —NHSO$_2$aryl, aryl, —SR$^{6d}$, —SOR$^{6e}$, —SO$_2$R$^{6f}$, —SO$_2$aryl, or $R^1$ and $R^2$ together with carbon atoms attached thereto form a ring or a 3-14 membered heterocyclic ring containing 1-4 heteroatoms selected from N, O, S, SO and/or SO$_2$;

$R^3$ represents OR$^8$, a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or SO$_2$;

$R^4$, $R^{5a}$, $R^{5b}$ and $R^{5c}$ respectively represent hydrogen, (C$_{1-18}$-alkyl)carbonyl, (C$_{1-18}$-alkyl)oxycarbonyl, arylcarbonyl, or aryl-(C$_{1-3}$alkyl)carbonyl;

$R^8$ represents a 6 membered fused-ring group;

$R^6$, $R^{6a}$, $R^{6b}$, $R^{6c}$, $R^{6d}$, $R^{6e}$ and $R^{6f}$ respectively represent alkyl or cycloalkyl, or alkyl or cycloalkyl in which one or more carbon atoms are replaced with one or more heteroatoms selected from N, O, S, SO and/or SO$_2$;

$R^7$, $R^{7a}$, $R^{7b}$, $R^{7c}$ and $R^{7d}$ respectively represent hydrogen, alkyl, aryl, alkylaryl or cycloalkyl, or $R^7$ and $R^{7a}$ together with the nitrogen attached thereto form a 3-14 membered heterocyclyl containing 1-4 heteroatoms selected from N, O, S, SO and/or SO$_2$;

X represents a chemical bond, NH, O, S, SO, SO$_2$ or an alkylene, said alkylene can be further substituted by one or more substituents, which comprise halogen, hydroxyl, C$_{1-4}$alkyl, cycloalkyl, C$_{1-4}$alkoxy, C$_{1-4}$alkyl that is substituted by halogen;

wherein the alkyl, the cycloalkyl, the aryl, the heterocyclyl, the spiro-ring group, the bridged-ring group, and the fused-ring group, as mentioned above, can be further substituted by one or more substituents, which comprise halogen, hydroxyl, amino, carboxyl, alkyl, alkoxy, aminosulfonyl, carbamoyl, C$_{1-4}$alkoxy that is substituted by halogen, and C$_{1-4}$alkyl that is substituted by halogen, hydroxyl, amino, and/or carboxyl.

2. The compound according to claim 1, a pharmaceutically acceptable salt thereof or a stereoisomer thereof:

wherein, $R^1$ represents hydrogen, —OH, —OR$^6$, alkyl, —CF$_3$, —OCHF$_2$, —OCF$_3$, halogen or —CN;

R² represents hydrogen;
R³ represents OR⁸, a 5-12 membered spiro-ring group, a 5-12 membered bridged-ring group or a 6-14 membered fused-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or SO₂;
R⁴, R⁵ᵃ, R⁵ᵇ and R⁵ᶜ respectively represent hydrogen, ($C_{1-18}$-alkly)carbonyl, ($C_{1-18}$-alkyl)oxycarbonyl, arylcarbonyl, or aryl-($C_{1-3}$alkyl)carbonyl;
R⁸ represents a 6 membered fused-ring group;
X represents a chemical bond or an alkylene, said alkylene can be further substituted by one or more substituents, which comprise halogen, hydroxyl, $C_{1-4}$alkyl, $C_{1-4}$alkoxy, and $C_{1-4}$alkyl that is substituted by halogen;
wherein the alkyl, the aryl, the spiro-ring group, the bridged-ring group, and the fused-ring group can be further substituted by one or more substituents, which comprise halogen, hydroxyl, amino, carboxyl, alkyl, alkoxy, aminosulfonyl, carbamoyl, $C_{1-4}$alkoxy that is substituted by halogen, and $C_{1-4}$alkyl that is substituted by halogen, hydroxyl, amino, and/or carboxyl.

3. The compound according to claim 1, a pharmaceutically acceptable salt thereof or a stereoisomer thereof:
wherein,
R¹ represents hydrogen, —OH, —OR⁶, alkyl, —CF₃, —OCHF₂, —OCF₃, halogen or —CN;
R² represents hydrogen;
R³ represents OR⁸, a 7-12 membered spiro-ring group, or a 5-12 membered spiro-ring group, a 5-12 membered bridged-ring group or a 6-14 membered fused-ring group in which one or more carbon atoms are replaced with one or more heteroatoms selected from N, O, S, SO and/or SO₂;
R⁸ represents a 6 membered fused-ring group;
R⁴, R⁵ᵃ, R⁵ᵇ and R⁵ᶜ respectively represent hydrogen;
X is methylene;
wherein the spiro-ring group and the fused-ring group can be further substituted by one or more substituents, which comprise halogen, hydroxyl, amino, carboxyl, alkyl, alkoxy, aminosulfonyl, carbamoyl, $C_{1-4}$alkoxy that is substituted by halogen, and $C_{1-4}$alkyl that is substituted by halogen, hydroxyl, amino, and/or carboxyl.

4. The compound according to claim 1, a pharmaceutically acceptable salt thereof or a stereoisomer thereof:
wherein,
R¹ represents halogen or —CN;
R² represents hydrogen;
R³ represents OR⁸ or a 7-12 membered spiro-ring group;
R⁸ represents a 6 membered fused-ring group;
R⁴, R⁵ᵃ, R⁵ᵇ and R⁵ᶜ respectively represent hydrogen;
X is methylene;
wherein the spiro-ring group and the fused-ring group can be further substituted by one or more substituents, which comprise halogen, hydroxyl, amino, carboxyl, $C_{1-6}$alkyl, $C_{1-6}$alkoxy, aminosulfonyl, and carbamoyl.

5. The compound according to claim 1, a pharmaceutically acceptable salt thereof or a stereoisomer thereof:
wherein,
R¹ represents halogen or —CN;
R² represents hydrogen;
R³ represents OR⁸, a 7-10 membered spiro-ring group or a 7-10 membered spiro-ring group containing 1-2 heteroatoms selected from N, O, S, SO and/or SO₂;

R⁸ represents 6 membered fused-ring group;
R⁴, R⁵ᵃ, R⁵ᵇ and R⁵ᶜ respectively represent hydrogen;
X is methylene.

6. The compound according to claim 1, a pharmaceutically acceptable salt thereof or a stereoisomer thereof:
wherein,
R¹ represents halogen;
R² represents hydrogen;
R³ represents OR⁸ or a 7-10 membered spiro-ring group;
R⁸ represents a 6 membered fused-ring group;
R⁴, R⁵ᵃ, R⁵ᵇ and R⁵ᶜ respectively represent hydrogen;
X is methylene.

7. The compound according to claim 1, a pharmaceutically acceptable salt thereof or a stereoisomer thereof:
wherein R³ is selected from:

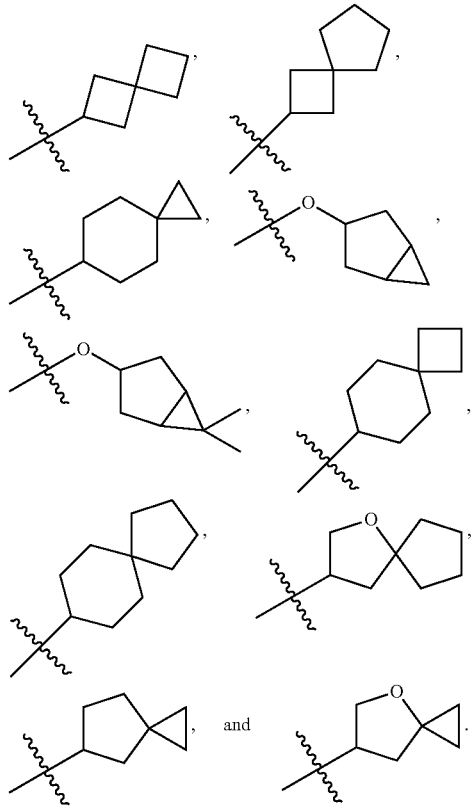

8. The compound according to claim 1, a pharmaceutically acceptable salt thereof or a stereoisomer thereof, wherein said compound is selected from the group consisting of:

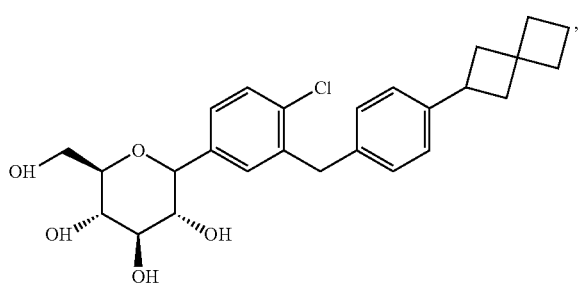

101
-continued
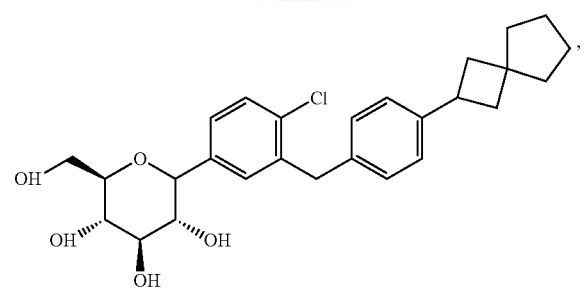
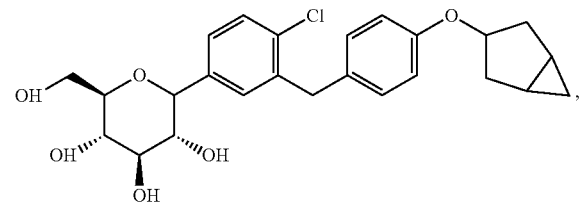
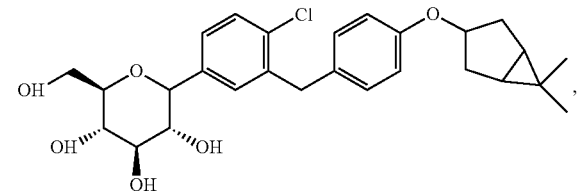
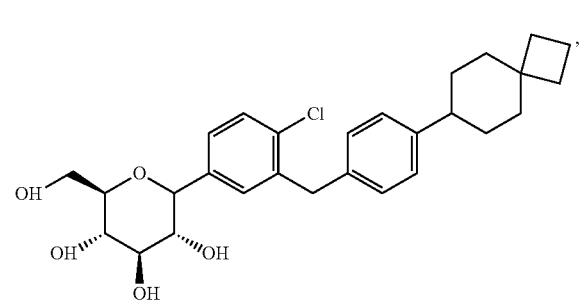
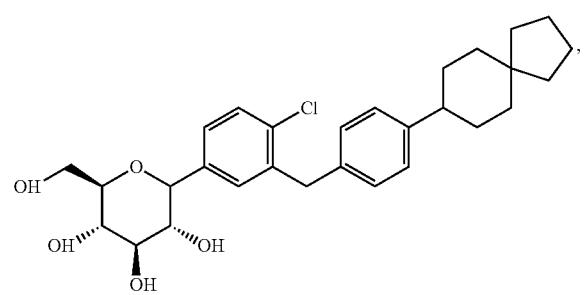
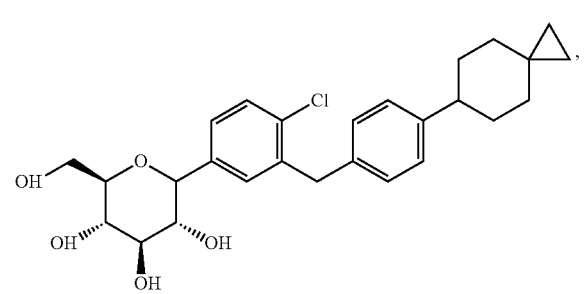
102
-continued
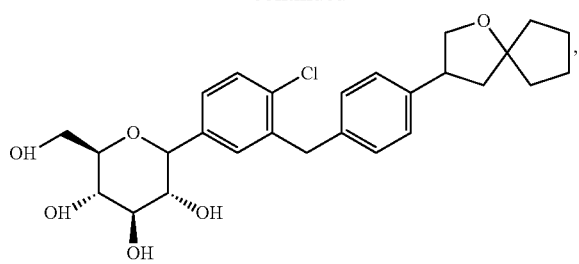
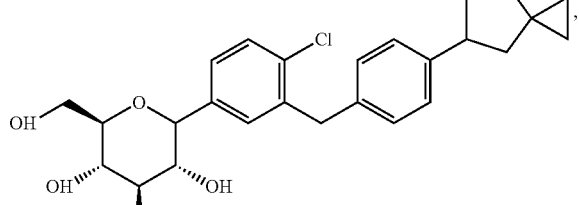
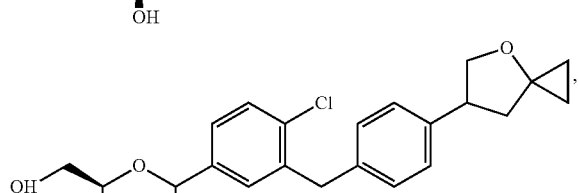
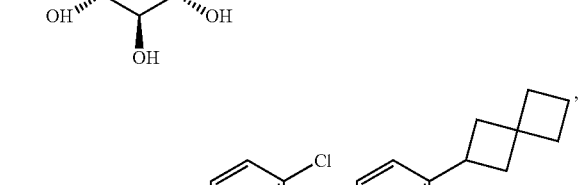
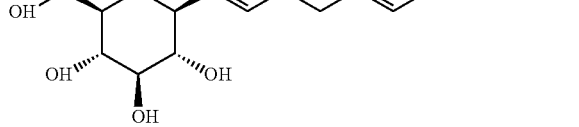
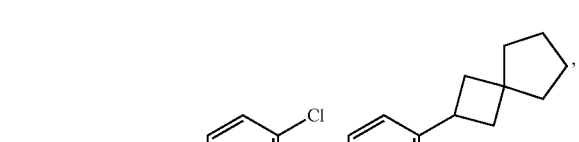
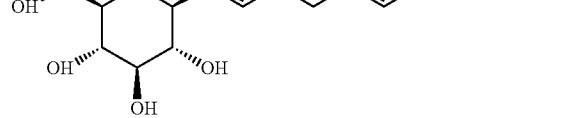
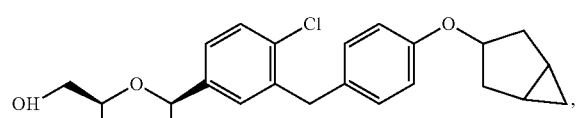

103
-continued
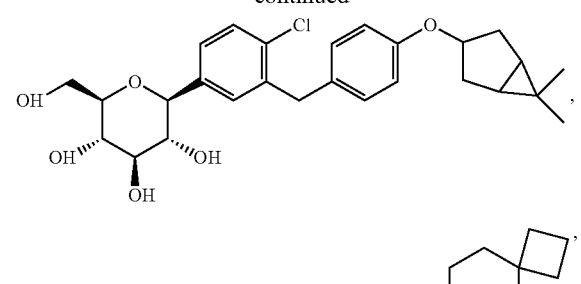
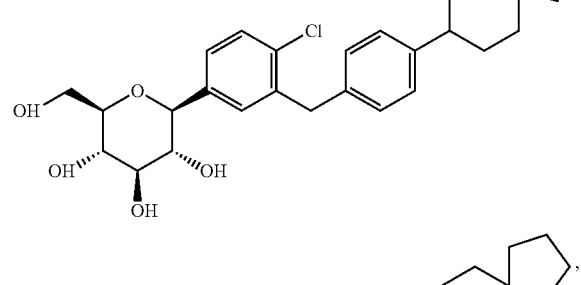
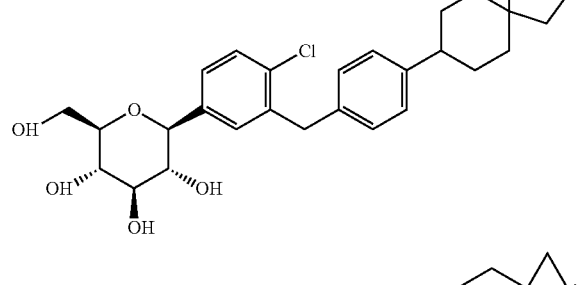
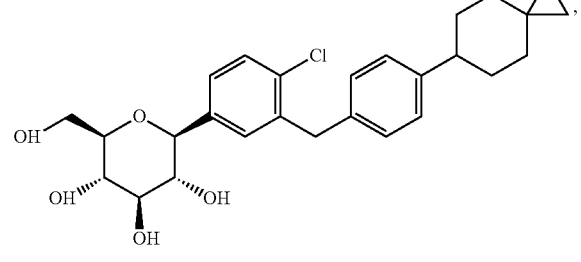
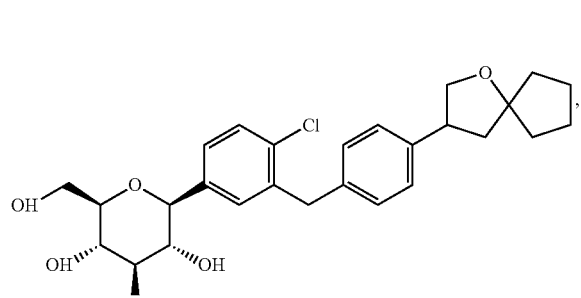
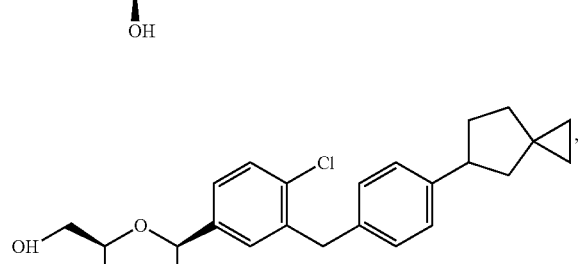
104
-continued
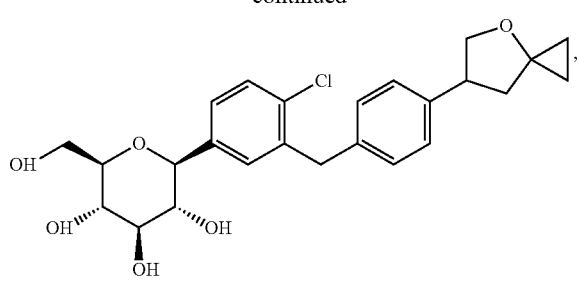
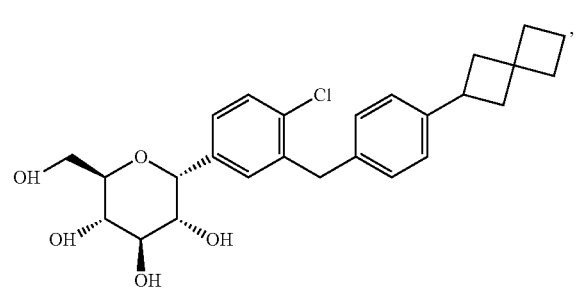
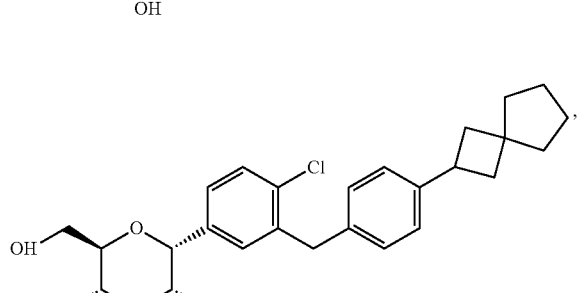
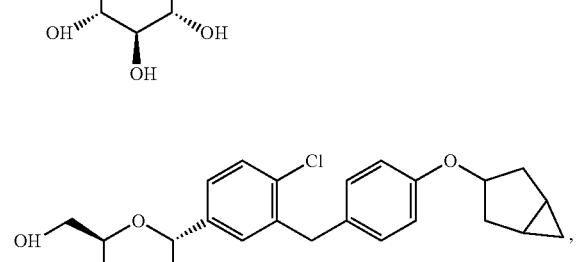
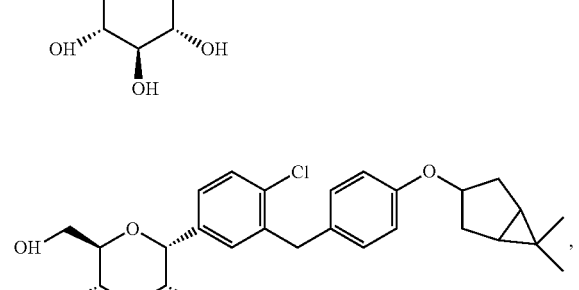
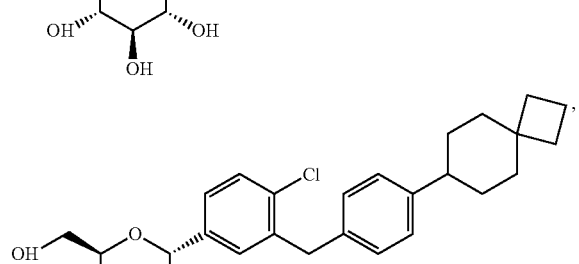

-continued

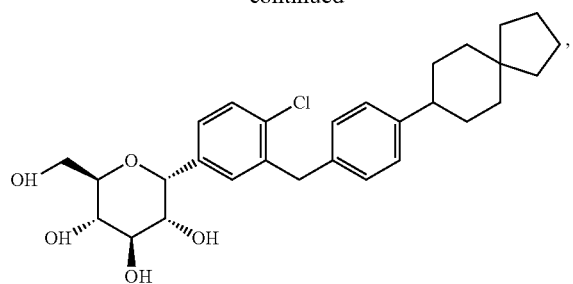

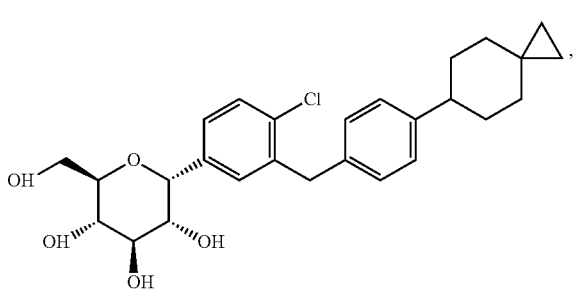

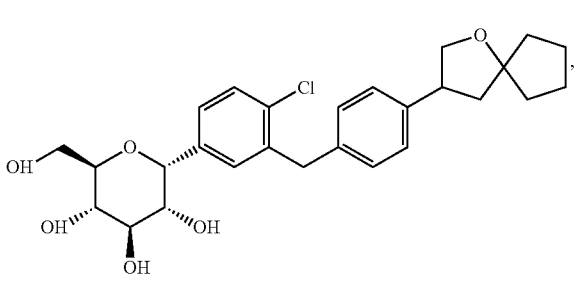

-continued

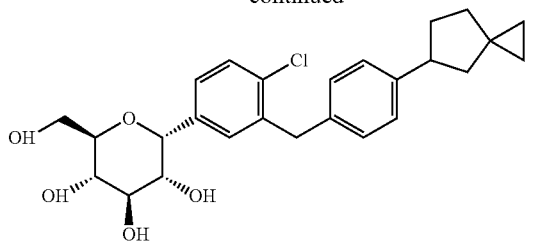

and

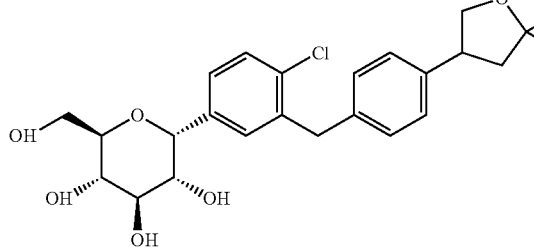

9. A pharmaceutical composition, which contains the compound according to claim 1, a pharmaceutically acceptable salt thereof or a stereoisomer thereof, and one or more pharmaceutically acceptable carriers and/or diluents, and is in any pharmaceutically acceptable dosage form.

10. A method for the treatment of insulin-dependent diabetes mellitus, non-insulin-dependent diabetes mellitus, and various diabetes-associated diseases, comprising the administration of a therapeutically effective amount of the compound according to claim 1, a pharmaceutically acceptable salt thereof or a stereoisomer thereof as sodium glucose co-transporter inhibitor to a subject in need thereof.

11. The method according to claim 10, wherein the diabetes-associated disease is insulin resistance disease or obesity.

* * * * *

UNITED STATES PATENT AND TRADEMARK OFFICE
CERTIFICATE OF CORRECTION

PATENT NO. : 9,562,029 B2  
APPLICATION NO. : 14/129316  
DATED : February 7, 2017  
INVENTOR(S) : Wu Page 1 of 1

It is certified that error appears in the above-identified patent and that said Letters Patent is hereby corrected as shown below:

On the Title Page

Item (54), and in the Specification, Column 1, Line 1, delete "C-GLYCOSIDE DERIVATIVES" and insert --C-GLYCOSIDE DERIVATIVE--

Signed and Sealed this  
Fourth Day of April, 2017

Michelle K. Lee  
*Director of the United States Patent and Trademark Office*